US011298453B2

(12) United States Patent
Blott et al.

(10) Patent No.: US 11,298,453 B2
(45) Date of Patent: *Apr. 12, 2022

(54) APPARATUS AND METHOD FOR WOUND CLEANSING WITH ACTIVES

(71) Applicant: Smith & Nephew PLC, Watford (GB)

(72) Inventors: Patrick Lewis Blott, Barmby Moor (GB); Clare Green, Crockey Hill (GB); Bryan Greener, York (GB); Edward Yerbury Hartwell, Hull (GB); Julian Lee-Webb, Copmanthorpe (GB); Robin Paul Martin, Selby (GB); Derek Nicolini, Hull (GB); Tina Michelle Walker, Shelton (GB)

(73) Assignee: Smith & Nephew PLC, Watford (GB)

(*) Notice: Subject to any disclaimer, the term of this patent is extended or adjusted under 35 U.S.C. 154(b) by 657 days.

This patent is subject to a terminal disclaimer.

(21) Appl. No.: 16/142,411

(22) Filed: Sep. 26, 2018

(65) Prior Publication Data

US 2019/0091385 A1 Mar. 28, 2019

Related U.S. Application Data

(63) Continuation of application No. 14/311,182, filed on Jun. 20, 2014, now abandoned, which is a
(Continued)

(30) Foreign Application Priority Data

Oct. 28, 2003 (GB) ...................................... 0325120
Apr. 28, 2004 (GB) ...................................... 0409443
(Continued)

(51) Int. Cl.
*A61M 1/00* (2006.01)
*A61M 35/00* (2006.01)

(52) U.S. Cl.
CPC ................ *A61M 1/85* (2021.05); *A61M 1/90* (2021.05); *A61M 35/30* (2019.05)

(58) Field of Classification Search
CPC ... A61M 1/0084; A61M 1/0088; A61M 35/00
(Continued)

(56) References Cited

U.S. PATENT DOCUMENTS 1,066,934 A 7/1913 Manney
2,280,915 A 4/1942 Johnson
(Continued)

FOREIGN PATENT DOCUMENTS

CA 2 349 638 5/2000
CA 2 369 024 10/2000
(Continued)

OTHER PUBLICATIONS

Thomas, S. et al., "Hydrocolloids: A guide to composition, properties and uses of hydrocolloid dressings and the commercial presentations available," J. of Wound Care, vol. 1, No. 2, Jul.-Aug. 1992, pp. 27-30, in 5 pages.
(Continued)

*Primary Examiner* — Andrew J Mensh
(74) *Attorney, Agent, or Firm* — Knobbe, Martens, Olson & Bear, LLP

(57) ABSTRACT

An apparatus and method for cleansing and applying therapy or prophylaxis to wounds, in which irrigant fluid, which may contain a physiologically active material, and wound exudate from the dressing are moved by a device for moving fluid through a flow path which passes through the dressing. A means for fluid cleansing may also be provided to recirculate fluid back to the dressing. The cleansing means removes materials deleterious to wound healing, and the cleansed fluid, still containing materials that are beneficial in promoting wound healing, is returned to the wound bed. The
(Continued)

apparatus may also provide means for distributing such materials in a precise and time-controlled manner over the wound bed. It may also contain a means for providing simultaneous aspiration and irrigation of the wound.

13 Claims, 38 Drawing Sheets

Related U.S. Application Data continuation of application No. 12/976,935, filed on Dec. 22, 2010, now Pat. No. 8,758,313, which is a continuation-in-part of application No. 10/576,263, filed as application No. PCT/GB2004/004566 on Oct. 28, 2004, now Pat. No. 8,257,327, said application No. 12/976,935 is a continuation-in-part of application No. 10/599,728, filed as application No. PCT/GB2005/001612 on Apr. 27, 2005, now abandoned, said application No. 12/976,935 is a continuation-in-part of application No. 12/066,578, filed as application No. PCT/GB2006/003421 on Sep. 15, 2006, now abandoned, said application No. 12/976,935 is a continuation-in-part of application No. 12/066,730, filed as application No. PCT/GB2006/003425 on Sep. 15, 2006, now abandoned, said application No. 12/976,935 is a continuation-in-part of application No. 12/066,585, filed as application No. PCT/GB2006/003416 on Sep. 15, 2006, now Pat. No. 8,162,909.

(30) Foreign Application Priority Data

Sep. 15, 2005 (GB) .................................... 0518804
Sep. 15, 2005 (GB) .................................... 0518825
Sep. 15, 2005 (GB) .................................... 0518826

(58) Field of Classification Search
USPC ........................................................ 604/349
See application file for complete search history.

(56) References Cited

U.S. PATENT DOCUMENTS

| | | |
|---|---|---|
| 3,171,410 A | 3/1965 | Towle et al. |
| 3,288,140 A | 11/1966 | McCarthy |
| 3,367,332 A | 2/1968 | Groves |
| 3,568,675 A | 3/1971 | Harvey |
| 3,624,821 A | 11/1971 | Henderson |
| 3,786,801 A | 1/1974 | Sartorius |
| 3,874,387 A | 4/1975 | Barbieri |
| 3,922,957 A | 12/1975 | Ogle et al. |
| 3,993,080 A | 11/1976 | Loseff |
| 4,112,947 A | 9/1978 | Nehring |
| 4,136,696 A | 1/1979 | Nehring |
| 4,178,938 A | 12/1979 | Au |
| 4,180,074 A | 12/1979 | Murry et al. |
| 4,184,510 A | 1/1980 | Murry et al. |
| 4,224,945 A | 9/1980 | Cohen |
| 4,252,119 A | 2/1981 | Coates |
| 4,316,466 A | 2/1982 | Babb |
| 4,341,207 A | 7/1982 | Steer et al. |
| 4,360,021 A | 11/1982 | Stima |
| 4,366,169 A | 12/1982 | White |
| 4,382,441 A | 5/1983 | Svedman |
| 4,465,485 A | 8/1984 | Kashmer et al. |
| 4,466,431 A | 8/1984 | Tharrat et al. |
| 4,499,896 A | 2/1985 | Heinecke |
| 4,529,402 A | 7/1985 | Weilbacher et al. |
| 4,530,360 A | 7/1985 | Duarte |
| 4,561,435 A | 12/1985 | McKnight et al. |
| 4,568,327 A | 2/1986 | Seufert |
| 4,573,965 A | 3/1986 | Russo |
| 4,587,101 A | 5/1986 | Marsoner et al. |
| 4,650,462 A | 3/1987 | DeSatnick et al. |
| 4,657,006 A | 4/1987 | Rawlings et al. |
| 4,664,662 A | 5/1987 | Webster |
| 4,699,134 A | 10/1987 | Samuelsen |
| 4,710,165 A | 12/1987 | McNeil et al. |
| 4,759,354 A | 7/1988 | Quarfoot |
| 4,778,446 A | 10/1988 | Jensen |
| 4,787,888 A | 11/1988 | Fox |
| 4,792,328 A | 12/1988 | Beck et al. |
| 4,798,603 A | 1/1989 | Meyer et al. |
| 4,813,931 A | 3/1989 | Hauze |
| 4,817,594 A | 4/1989 | Juhasz |
| 4,836,192 A | 6/1989 | Abbate |
| 4,867,150 A | 9/1989 | Gilbert |
| 4,872,450 A | 10/1989 | Austad |
| 4,875,473 A | 10/1989 | Alvarez |
| 4,882,213 A | 11/1989 | Gaddis et al. |
| 4,921,488 A | 5/1990 | Maitz et al. |
| 4,930,997 A | 6/1990 | Bennett |
| 4,936,834 A | 6/1990 | Beck et al. |
| 4,969,880 A | 11/1990 | Zamierowski |
| 4,979,944 A | 12/1990 | Luzsicza |
| 4,997,425 A | 3/1991 | Shioya et al. |
| 5,009,635 A | 4/1991 | Scarberry |
| 5,010,883 A | 4/1991 | Rawlings et al. |
| 5,030,202 A | 7/1991 | Harris |
| 5,055,195 A | 10/1991 | Trasch et al. |
| 5,055,198 A | 10/1991 | Shettigar |
| 5,073,172 A | 12/1991 | Fell |
| 5,080,661 A | 1/1992 | Lavender et al. |
| 5,100,396 A | 3/1992 | Zamierowski |
| 5,112,323 A | 5/1992 | Winkler et al. |
| 5,149,331 A | 9/1992 | Ferdman et al. |
| 5,152,757 A * | 10/1992 | Eriksson ................ A61K 48/00 604/305 |
| 5,176,663 A | 1/1993 | Svedman et al. |
| 5,215,539 A | 6/1993 | Schoolman |
| 5,218,973 A | 6/1993 | Weaver et al. |
| 5,261,893 A | 11/1993 | Zamierowski |
| 5,264,218 A | 11/1993 | Rogozinski |
| 5,322,695 A | 6/1994 | Shah et al. |
| 5,328,614 A | 7/1994 | Matsumura |
| 5,336,209 A | 8/1994 | Porzilli |
| 5,358,494 A | 10/1994 | Svedman |
| 5,360,398 A | 11/1994 | Grieshaber et al. |
| 5,380,280 A | 1/1995 | Peterson |
| 5,419,768 A | 5/1995 | Kayser |
| 5,419,772 A | 5/1995 | Teitz et al. |
| 5,460,490 A | 10/1995 | Carr et al. |
| 5,486,158 A | 1/1996 | Samuelson |
| 5,487,889 A | 1/1996 | Eckert et al. |
| 5,490,984 A | 2/1996 | Freed |
| 5,496,605 A | 3/1996 | Augst et al. |
| 5,498,338 A | 3/1996 | Kruger et al. |
| 5,527,293 A | 6/1996 | Zamierowski |
| 5,527,923 A | 6/1996 | Klingler et al. |
| 5,549,584 A | 8/1996 | Gross |
| 5,578,317 A | 11/1996 | Mulder |
| 5,593,395 A | 1/1997 | Martz |
| 5,599,289 A | 2/1997 | Castellana |
| 5,616,387 A | 4/1997 | Augst et al. |
| 5,633,007 A | 5/1997 | Webb et al. |
| 5,636,643 A | 6/1997 | Argenta et al. |
| 5,645,081 A | 7/1997 | Argenta et al. |
| 5,662,924 A | 9/1997 | Rhodes |
| 5,676,650 A | 10/1997 | Grieshaber et al. |
| 5,678,564 A | 10/1997 | Lawrence et al. |
| 5,681,579 A | 10/1997 | Freeman |
| 5,713,881 A | 2/1998 | Rezai et al. |
| 5,714,225 A | 2/1998 | Hansen et al. |
| 5,716,411 A | 2/1998 | Orgill et al. |
| 5,733,253 A | 3/1998 | Headley et al. |
| 5,733,305 A | 3/1998 | Fleischmann |
| 5,759,570 A * | 6/1998 | Arnold ................. A61L 15/325 424/443 |
| 5,778,890 A | 7/1998 | Lofgren et al. |

(56) References Cited

U.S. PATENT DOCUMENTS

| | | |
|---|---|---|
| 5,792,090 A | 8/1998 | Ladin |
| 5,810,755 A | 9/1998 | LeVeen et al. |
| 5,810,765 A | 9/1998 | Oda |
| 5,830,176 A | 11/1998 | Mackool |
| 5,885,237 A | 3/1999 | Kadash et al. |
| 5,893,862 A | 4/1999 | Pratt et al. |
| 5,899,893 A | 5/1999 | Dyer et al. |
| 5,904,659 A | 5/1999 | Duarte |
| 5,910,125 A | 6/1999 | Cummings et al. |
| 5,911,222 A | 6/1999 | Lawrence et al. |
| 5,941,859 A | 8/1999 | Lerman |
| 5,954,680 A | 9/1999 | Augustine |
| 5,958,420 A | 9/1999 | Jenson |
| 5,964,723 A | 10/1999 | Augustine |
| 5,976,117 A | 11/1999 | Dunshee et al. |
| 5,981,822 A | 11/1999 | Addison |
| 5,985,990 A | 11/1999 | Kantner et al. |
| 6,071,267 A * | 6/2000 | Zamierowski ...... A61F 13/0203 604/289 |
| 6,087,549 A | 7/2000 | Flick |
| 6,117,111 A | 9/2000 | Fleischmann |
| 6,142,982 A | 11/2000 | Hunt et al. |
| 6,156,334 A | 12/2000 | Meyer-Ingold et al. |
| 6,168,800 B1 | 1/2001 | Dobos et al. |
| 6,201,164 B1 | 3/2001 | Wulff et al. |
| 6,203,563 B1 | 3/2001 | Fernandez |
| 6,254,567 B1 | 7/2001 | Treu et al. |
| 6,261,283 B1 | 7/2001 | Morgan et al. |
| 6,293,281 B1 | 9/2001 | Shultz et al. |
| 6,345,623 B1 | 2/2002 | Heaton et al. |
| 6,350,339 B1 | 2/2002 | Sessions |
| 6,398,767 B1 * | 6/2002 | Fleischmann ....... A61M 1/0088 604/304 |
| 6,458,109 B1 | 10/2002 | Henley et al. |
| 6,465,708 B1 | 10/2002 | Augustine |
| 6,496,727 B1 | 12/2002 | Bernhard et al. |
| 6,520,982 B1 | 2/2003 | Boynton et al. |
| 6,527,745 B1 | 3/2003 | Kanda et al. |
| 6,553,998 B2 | 4/2003 | Heaton et al. |
| 6,626,827 B1 | 9/2003 | Felix et al. |
| 6,626,891 B2 | 9/2003 | Ohmstede |
| 6,673,982 B1 | 1/2004 | Chen et al. |
| 6,680,113 B1 | 1/2004 | Lucast et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,787,682 B2 | 9/2004 | Gilman |
| 6,794,554 B2 | 9/2004 | Sessions et al. |
| 6,797,855 B2 | 9/2004 | Worthley |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,974,428 B2 | 12/2005 | Knutson et al. |
| 6,977,323 B1 | 12/2005 | Swenson |
| 6,979,324 B2 | 12/2005 | Bybordi et al. |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,048,951 B1 | 5/2006 | Seitz et al. |
| 7,077,832 B2 | 7/2006 | Fleischmann |
| 7,087,807 B2 | 8/2006 | Stapf |
| 7,108,683 B2 | 9/2006 | Zamierowski |
| 7,137,968 B1 | 11/2006 | Burrell et al. |
| 7,195,624 B2 | 3/2007 | Lockwood |
| 7,211,060 B1 | 5/2007 | Talish et al. |
| 7,216,651 B2 | 5/2007 | Argenta et al. |
| 7,291,762 B2 | 11/2007 | Flick |
| 7,335,809 B2 | 2/2008 | Riesinger |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,518,031 B2 | 4/2009 | Liedtke et al. |
| 7,524,315 B2 | 4/2009 | Blott et al. |
| 7,532,953 B2 | 5/2009 | Vogel |
| 7,534,240 B1 | 5/2009 | Johnson |
| 7,534,927 B2 | 5/2009 | Lockwood |
| 7,553,306 B1 | 6/2009 | Hunt et al. |
| 7,611,500 B1 | 11/2009 | Lina et al. |
| 7,625,362 B2 | 12/2009 | Boehringer et al. |
| 7,628,764 B2 | 12/2009 | Duarte et al. |
| 7,629,384 B2 | 12/2009 | Fossel |
| 7,645,253 B2 | 1/2010 | Gura et al. |
| 7,645,269 B2 | 1/2010 | Zamierowski |
| 7,670,323 B2 | 3/2010 | Hunt et al. |
| 7,678,090 B2 | 3/2010 | Risk, Jr. |
| 7,678,102 B1 | 3/2010 | Heaton |
| 7,686,785 B2 | 3/2010 | Boehringer et al. |
| 7,699,830 B2 | 4/2010 | Martin |
| 7,722,582 B2 | 5/2010 | Lina et al. |
| 7,731,702 B2 | 6/2010 | Bybordi et al. |
| 7,753,894 B2 | 7/2010 | Blott et al. |
| 7,759,538 B2 | 7/2010 | Fleischmann |
| 7,767,936 B2 | 8/2010 | Ferguson |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,828,782 B2 | 11/2010 | Suzuki |
| 7,846,141 B2 | 12/2010 | Weston |
| 7,862,718 B2 | 1/2011 | Doyen et al. |
| 7,867,206 B2 | 1/2011 | Lockwood et al. |
| 7,879,605 B2 | 2/2011 | Holland et al. |
| 7,883,494 B2 | 2/2011 | Martin |
| 7,896,856 B2 | 3/2011 | Petrosenko et al. |
| 7,896,864 B2 | 3/2011 | Lockwood et al. |
| 7,910,791 B2 | 3/2011 | Coffey |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,981,668 B2 | 7/2011 | Wilkes et al. |
| 7,988,680 B2 | 8/2011 | Lockwood et al. |
| 8,062,272 B2 | 11/2011 | Weston |
| 8,062,331 B2 | 11/2011 | Zamierowski |
| 8,070,773 B2 | 12/2011 | Zamierowski |
| 8,075,503 B2 | 12/2011 | Jaeb |
| 8,080,702 B2 | 12/2011 | Blott et al. |
| 8,100,887 B2 | 1/2012 | Weston et al. |
| 8,105,295 B2 | 1/2012 | Blott et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,158,844 B2 | 4/2012 | McNeil |
| 8,162,909 B2 | 4/2012 | Blott et al. |
| 8,168,848 B2 | 5/2012 | Lockwood et al. |
| 8,187,237 B2 | 5/2012 | Seegert |
| 8,192,409 B2 | 6/2012 | Hardman et al. |
| 8,235,955 B2 | 8/2012 | Blott et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,308,714 B2 | 11/2012 | Weston et al. |
| 8,338,402 B2 | 12/2012 | Fry et al. |
| 8,348,910 B2 | 1/2013 | Blott et al. |
| 8,357,188 B2 | 1/2013 | Boynton et al. |
| 8,398,614 B2 | 3/2013 | Blott et al. |

(56) References Cited

U.S. PATENT DOCUMENTS

| | | |
|---|---|---|
| 8,529,548 B2 | 9/2013 | Blott et al. |
| 8,529,578 B2 | 9/2013 | Daniels et al. |
| 8,535,296 B2 | 9/2013 | Blott et al. |
| D692,565 S | 10/2013 | Lattimore et al. |
| 8,569,566 B2 | 10/2013 | Blott et al. |
| 8,632,512 B2 | 1/2014 | Zimnitsky et al. |
| 8,647,327 B2 | 2/2014 | Larsson et al. |
| 8,680,360 B2 | 3/2014 | Greener et al. |
| 8,747,887 B2 | 6/2014 | Coffey |
| 8,758,313 B2 * | 6/2014 | Blott .................... A61M 35/30 604/313 |
| 8,791,316 B2 | 7/2014 | Greener |
| 8,834,451 B2 | 9/2014 | Blott et al. |
| 8,845,619 B2 | 9/2014 | Blott et al. |
| 8,882,746 B2 | 11/2014 | Blott et al. |
| 8,915,896 B2 | 12/2014 | Sanders et al. |
| 8,926,592 B2 | 1/2015 | Blott et al. |
| 8,998,866 B2 | 4/2015 | Hicks |
| 9,044,569 B2 | 6/2015 | Blott et al. |
| 9,107,998 B2 | 8/2015 | Pratt et al. |
| 9,205,001 B2 | 12/2015 | Blott et al. |
| 9,226,737 B2 | 1/2016 | Dunn |
| 9,289,542 B2 | 3/2016 | Blott et al. |
| 9,408,956 B2 | 8/2016 | Zamierowski |
| 2001/0018072 A1 | 8/2001 | Unger |
| 2001/0020145 A1 | 9/2001 | Satterfield et al. |
| 2001/0027285 A1 | 10/2001 | Heinecke et al. |
| 2001/0029956 A1 | 10/2001 | Argenta |
| 2001/0034499 A1 | 10/2001 | Sessions et al. |
| 2001/0037810 A1 | 11/2001 | Fine et al. |
| 2001/0043943 A1 | 11/2001 | Coffey |
| 2002/0016570 A1 | 2/2002 | Cartledge |
| 2002/0068913 A1 | 6/2002 | Fleischmann |
| 2002/0082567 A1 | 6/2002 | Lockwood et al. |
| 2002/0114847 A1 | 8/2002 | Peshoff |
| 2002/0138036 A1 | 9/2002 | Babaev |
| 2002/0161346 A1 | 10/2002 | Lockwood et al. |
| 2002/0198504 A1 | 12/2002 | Risk et al. |
| 2003/0021775 A1 | 1/2003 | Freeman |
| 2003/0050594 A1 | 3/2003 | Zamierowski |
| 2003/0093041 A1 | 5/2003 | Risk, Jr. et al. |
| 2003/0109855 A1 | 6/2003 | Solem et al. |
| 2003/0134332 A1 | 7/2003 | Boykin, Jr. |
| 2003/0144619 A1 | 7/2003 | Augustine |
| 2003/0148959 A1 | 8/2003 | Quirk et al. |
| 2003/0171675 A1 | 9/2003 | Rosenberg |
| 2003/0175798 A1 | 9/2003 | Raees et al. |
| 2003/0208149 A1 * | 11/2003 | Coffey ................ A61L 15/325 602/48 |
| 2003/0211137 A1 | 11/2003 | Sierra |
| 2003/0212357 A1 * | 11/2003 | Pace .................... A61M 1/784 602/41 |
| 2003/0212431 A1 | 11/2003 | Brady et al. |
| 2003/0225347 A1 | 12/2003 | Argenta et al. |
| 2004/0001878 A1 | 1/2004 | DeBusk et al. |
| 2004/0019252 A1 | 1/2004 | Hirata |
| 2004/0054338 A1 | 3/2004 | Bybordi et al. |
| 2004/0064111 A1 | 4/2004 | Lockwood et al. |
| 2004/0077977 A1 | 4/2004 | Ella et al. |
| 2004/0127836 A1 | 7/2004 | Sigurjonsson et al. |
| 2004/0127845 A1 | 7/2004 | Renz et al. |
| 2004/0162512 A1 | 8/2004 | Liedtke et al. |
| 2004/0241214 A1 | 12/2004 | Kirkwood et al. |
| 2005/0090787 A1 | 4/2005 | Risk et al. |
| 2005/0107756 A1 | 5/2005 | McCraw |
| 2005/0113733 A1 | 5/2005 | Liedtke et al. |
| 2005/0130299 A1 | 6/2005 | Suzuki |
| 2005/0131327 A1 | 6/2005 | Lockwood et al. |
| 2005/0143697 A1 | 6/2005 | Riesinger |
| 2005/0181163 A1 | 8/2005 | Kose |
| 2006/0029675 A1 | 2/2006 | Ginther |
| 2006/0142687 A1 | 6/2006 | Liedtke et al. |
| 2006/0172000 A1 | 8/2006 | Cullen et al. |
| 2006/0178608 A1 | 8/2006 | Stapf |
| 2006/0241689 A1 | 10/2006 | Leiboff et al. |
| 2007/0014837 A1 | 1/2007 | Johnson et al. |
| 2007/0032763 A1 | 2/2007 | Vogel |
| 2007/0038172 A1 | 2/2007 | Zamierowski |
| 2007/0142761 A1 | 6/2007 | Aali |
| 2007/0219471 A1 | 9/2007 | Johnson et al. |
| 2007/0225663 A1 | 9/2007 | Watt et al. |
| 2007/0292397 A1 | 12/2007 | McNulty et al. |
| 2007/0292488 A1 | 12/2007 | Bassiri et al. |
| 2008/0033330 A1 | 2/2008 | Moore |
| 2008/0065001 A1 | 3/2008 | DiNucci et al. |
| 2008/0069855 A1 | 3/2008 | Bonutti |
| 2008/0091133 A1 | 4/2008 | Matter |
| 2008/0095979 A1 | 4/2008 | Hatanaka et al. |
| 2008/0125697 A1 | 5/2008 | Gao |
| 2008/0125698 A1 | 5/2008 | Gerg et al. |
| 2008/0199513 A1 | 8/2008 | Beretta et al. |
| 2008/0208147 A1 | 8/2008 | Argenta et al. |
| 2008/0213344 A1 | 9/2008 | McCarthy et al. |
| 2008/0226720 A1 | 9/2008 | Kemp et al. |
| 2008/0243044 A1 | 10/2008 | Hunt et al. |
| 2009/0054855 A1 | 2/2009 | Blott et al. |
| 2009/0099519 A1 | 4/2009 | Kaplan |
| 2009/0105671 A1 | 4/2009 | Daggar et al. |
| 2009/0130186 A1 | 5/2009 | McCarthy et al. |
| 2009/0157016 A1 | 6/2009 | Adahan |
| 2009/0163882 A1 | 6/2009 | Koch et al. |
| 2009/0177136 A1 | 7/2009 | Liedtke et al. |
| 2009/0221977 A1 | 9/2009 | Blott et al. |
| 2009/0227969 A1 | 9/2009 | Jaeb et al. |
| 2009/0240185 A1 | 9/2009 | Jaeb et al. |
| 2009/0306580 A1 | 12/2009 | Blott et al. |
| 2009/0312723 A1 | 12/2009 | Blott et al. |
| 2010/0069829 A1 | 3/2010 | Hutchinson et al. |
| 2010/0069850 A1 | 3/2010 | Fabo |
| 2010/0069858 A1 | 3/2010 | Olson |
| 2010/0069885 A1 | 3/2010 | Stevenson et al. |
| 2010/0094234 A1 | 4/2010 | Ramella et al. |
| 2010/0106117 A1 | 4/2010 | Lockwood et al. |
| 2010/0122417 A1 | 5/2010 | Vrzalik et al. |
| 2010/0249733 A9 | 9/2010 | Blott et al. |
| 2011/0004171 A1 | 1/2011 | Blott et al. |
| 2011/0004172 A1 | 1/2011 | Eckstein et al. |
| 2011/0028917 A1 | 2/2011 | Hall |
| 2011/0054423 A1 | 3/2011 | Blott et al. |
| 2011/0130712 A1 | 6/2011 | Topaz |
| 2011/0178451 A1 | 7/2011 | Robinson et al. |
| 2011/0257572 A1 | 10/2011 | Locke et al. |
| 2011/0257593 A1 | 10/2011 | Kalpin et al. |
| 2011/0313373 A1 | 12/2011 | Riesinger |
| 2011/0313374 A1 | 12/2011 | Lockwood et al. |
| 2012/0004628 A1 | 1/2012 | Blott et al. |
| 2012/0040013 A1 | 2/2012 | Owens et al. |
| 2012/0041399 A1 | 2/2012 | Blott et al. |
| 2012/0053538 A1 | 3/2012 | Blott et al. |
| 2012/0302976 A1 | 11/2012 | Locke et al. |
| 2013/0151223 A1 | 6/2013 | Zamierowski et al. |
| 2013/0165821 A1 | 6/2013 | Freedman et al. |
| 2013/0296818 A1 | 11/2013 | Bradford et al. |
| 2013/0310781 A1 | 11/2013 | Phillips et al. |
| 2014/0371691 A1 | 12/2014 | Blott et al. |
| 2015/0018786 A1 | 1/2015 | Locke et al. |
| 2015/0030663 A1 | 1/2015 | Clark et al. |
| 2015/0080788 A1 | 3/2015 | Blott et al. |
| 2015/0159066 A1 | 6/2015 | Hartwell et al. |
| 2015/0265754 A1 | 9/2015 | Blott et al. |
| 2016/0317356 A1 | 11/2016 | Corley |
| 2017/0252496 A1 | 9/2017 | Blott et al. |

FOREIGN PATENT DOCUMENTS

| | | |
|---|---|---|
| CN | 202069996 | 12/2011 |
| DE | 3 539 533 | 5/1987 |
| DE | 3 935 818 | 5/1991 |
| DE | 4 012 232 | 10/1991 |
| DE | 4 102 684 | 8/1992 |
| DE | 197 22 075 | 10/1998 |
| DE | 198 44 355 | 4/2000 |
| EP | 0 020 662 | 7/1984 |
| EP | 0 122 085 | 6/1987 |

(56) References Cited

FOREIGN PATENT DOCUMENTS

| | | |
|---|---|---|
| EP | 0 298 726 | 1/1989 |
| EP | 0 355 186 | 2/1990 |
| EP | 0 418 607 | 3/1991 |
| EP | 0 174 803 B1 | 8/1991 |
| EP | 0 485 657 | 5/1992 |
| EP | 0 325 771 | 9/1993 |
| EP | 0 617 938 | 10/1994 |
| EP | 0 638 301 | 2/1995 |
| EP | 0 670 705 | 9/1995 |
| EP | 0 465 601 | 1/1997 |
| EP | 0 762 860 | 3/1997 |
| EP | 0 620 720 | 3/1998 |
| EP | 0 853 950 | 7/1998 |
| EP | 0 651 983 | 9/1998 |
| EP | 0 777 504 | 10/1998 |
| EP | 0 688 189 | 9/2000 |
| EP | 0 865 304 | 7/2001 |
| EP | 1 088 569 | 8/2003 |
| EP | 0 880 953 | 10/2003 |
| EP | 1 219 311 | 7/2004 |
| EP | 1 018 967 | 8/2004 |
| EP | 1 488 816 | 12/2004 |
| EP | 1 513 478 | 3/2005 |
| EP | 1 440 667 | 3/2006 |
| EP | 1 284 777 | 4/2006 |
| EP | 1 772 160 | 4/2007 |
| EP | 2 366 721 | 9/2011 |
| EP | 2 650 028 | 10/2013 |
| EP | 1 742 683 | 2/2016 |
| FR | 1 163 907 | 10/1958 |
| GB | 114754 | 4/1918 |
| GB | 641061 | 8/1950 |
| GB | 1063066 | 3/1967 |
| GB | 1224009 | 3/1971 |
| GB | 1549756 | 8/1979 |
| GB | 2085305 | 1/1985 |
| GB | 2195255 | 4/1988 |
| GB | 2307180 | 5/1997 |
| GB | 2329127 | 3/1999 |
| GB | 2305610 | 7/1999 |
| GB | 2378392 | 2/2003 |
| GB | 2357286 | 11/2003 |
| GB | 2389794 | 12/2003 |
| GB | 2365350 | 8/2004 |
| GB | 2423019 | 8/2006 |
| JP | 59-502014 | 12/1984 |
| JP | S62-279885 | 12/1987 |
| JP | H10-277143 | 10/1998 |
| JP | 2001-314479 | 11/2001 |
| JP | 2001-525688 | 12/2001 |
| JP | 2003-154003 | 5/2003 |
| JP | 2004-121819 | 4/2004 |
| JP | 2012-200425 | 10/2012 |
| SU | 1251912 A1 | 4/1983 |
| WO | WO 1984/01904 | 5/1984 |
| WO | WO 1987/00759 | 2/1987 |
| WO | WO 1990/11795 | 10/1990 |
| WO | WO 1991/00718 | 1/1991 |
| WO | WO 1992/13713 | 8/1992 |
| WO | WO 1992/20299 | 11/1992 |
| WO | WO 1993/00056 | 1/1993 |
| WO | WO 1993/09727 | 5/1993 |
| WO | WO 1994/03214 | 2/1994 |
| WO | WO 1994/20041 | 9/1994 |
| WO | WO 1996/24316 | 8/1996 |
| WO | WO 1997/43991 | 11/1997 |
| WO | WO 1998/13000 | 4/1998 |
| WO | WO 1998/38955 | 9/1998 |
| WO | WO 1999/01173 | 1/1999 |
| WO | WO 2000/007653 | 2/2000 |
| WO | WO 2000/50143 | 8/2000 |
| WO | WO 2000/61206 | 10/2000 |
| WO | WO 2001/37773 | 5/2001 |
| WO | WO 2001/49233 | 7/2001 |
| WO | WO 2001/085248 | 11/2001 |
| WO | WO 2002/05737 | 1/2002 |
| WO | WO 2002/26180 | 4/2002 |
| WO | WO 2002/39940 | 5/2002 |
| WO | WO 2002/41878 | 5/2002 |
| WO | WO 2002/45761 | 6/2002 |
| WO | WO 2002/072113 | 9/2002 |
| WO | WO 2002/072800 | 9/2002 |
| WO | WO 2002/083046 | 10/2002 |
| WO | WO 2002/091965 | 11/2002 |
| WO | WO 2002/092783 | 11/2002 |
| WO | WO 2003/074100 | 9/2003 |
| WO | WO 2003/086232 | 10/2003 |
| WO | WO 2003/101385 | 11/2003 |
| WO | WO 2003/101508 | 12/2003 |
| WO | WO 2004/018020 | 3/2004 |
| WO | WO 2004/024300 | 3/2004 |
| WO | WO 2004/037334 | 5/2004 |
| WO | WO 2005/009488 | 2/2005 |
| WO | WO 2005/016179 | 2/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2006/014917 | 2/2006 |
| WO | WO 2006/028244 | 3/2006 |
| WO | WO 2006/052338 | 5/2006 |
| WO | WO 2006/052745 | 5/2006 |
| WO | WO 2006/054323 | 5/2006 |
| WO | WO 2006/114638 | 11/2006 |
| WO | WO 2006/130594 | 12/2006 |
| WO | WO 2007/006306 | 1/2007 |
| WO | WO 2007/013049 | 2/2007 |
| WO | WO 2007/013064 | 2/2007 |
| WO | WO 2007/016590 | 2/2007 |
| WO | WO 2007/019038 | 2/2007 |
| WO | WO 2007/075379 | 7/2007 |
| WO | WO 2007/092397 | 8/2007 |
| WO | WO 2007/095180 | 8/2007 |
| WO | WO 2007/106591 | 9/2007 |
| WO | WO 2007/120138 | 10/2007 |
| WO | WO 2007/123451 | 11/2007 |
| WO | WO 2008/005532 | 1/2008 |
| WO | WO 2008/005996 | 1/2008 |
| WO | WO 2008/008032 | 1/2008 |
| WO | WO 2008/010094 | 1/2008 |
| WO | WO 2008/027449 | 3/2008 |
| WO | WO 2008/028975 | 3/2008 |
| WO | WO 2008/030872 | 3/2008 |
| WO | WO 2008/036360 | 3/2008 |
| WO | WO 2008/039314 | 4/2008 |
| WO | WO 2008/039839 | 4/2008 |
| WO | WO 2008/040020 | 4/2008 |
| WO | WO 2008/040681 | 4/2008 |
| WO | WO 2008/041926 | 4/2008 |
| WO | WO 2008/042481 | 4/2008 |
| WO | WO 2008/048481 | 4/2008 |
| WO | WO 2008/064503 | 6/2008 |
| WO | WO 2008/100446 | 8/2008 |
| WO | WO 2008/104609 | 9/2008 |
| WO | WO 2008/131895 | 11/2008 |
| WO | WO 2008/140439 | 11/2008 |
| WO | WO 2009/002260 | 12/2008 |
| WO | WO 2009/011856 | 1/2009 |
| WO | WO 2009/021523 | 2/2009 |
| WO | WO 2009/070905 | 6/2009 |
| WO | WO 2009/111655 | 9/2009 |
| WO | WO 2009/126103 | 10/2009 |
| WO | WO 2009/140376 | 11/2009 |
| WO | WO 2009/146441 | 12/2009 |
| WO | WO 2009/158126 | 12/2009 |
| WO | WO 2009/158127 | 12/2009 |
| WO | WO 2010/006182 | 1/2010 |

(56) References Cited

FOREIGN PATENT DOCUMENTS

| WO | WO 2010/014177 | 2/2010 |
|---|---|---|
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/033769 | 3/2010 |
| WO | WO 2010/051068 | 5/2010 |
| WO | WO 2010/051073 | 5/2010 |
| WO | WO 2010/059712 | 5/2010 |
| WO | WO 2010/059730 | 5/2010 |
| WO | WO 2010/072309 | 7/2010 |
| WO | WO 2010/078166 | 7/2010 |
| WO | WO 2011/049562 | 4/2011 |
| WO | WO 2011/087871 | 7/2011 |
| WO | WO 2011/100851 | 8/2011 |
| WO | WO 2011/115908 | 9/2011 |
| WO | WO 2012/087376 | 6/2012 |
| WO | WO 2012/142002 | 10/2012 |
| WO | WO 2012/170744 | 12/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2014/184674 | 11/2014 |
| WO | WO 2015/026326 | 2/2015 |

OTHER PUBLICATIONS

"Magnitude," The American Heritage Dictionary of the English Language, Fifth Edition, 2011.
Achterberg, V. et al., "Hydroactive dressings and serum proteins: an in vitro study", Journal of Wound Care, February, vol. 5, No. 2, 1996, pp. 79-82, in 4 pages.
Aubrey, D.A., et al., "Treatment of the Perineal Wound after Proctectomy by Intermittent Irrigation", Arch. Surg., vol. 119, Oct. 1984, pp. 1141-1144, in 4 pages.
Bagautdinov, N.A., "Variant of External Vacuum Aspiration in the Treatment of Purulent Diseases of Soft Tissues", in Current Problems in Modern Clinical Surgery: Interdepartmental Collection, edited by V. Ye. Volkov et al. (Chuvash State University, Cheboksary, USSR 1986) pp. 94-96.
Barker et al., "Vacuum Pack Technique of Temporary Abdominal Closure"; J. of Traumatic Injury, Infection, and Critical Care, vol. 48, No. 2 (2000).
Bevan, D. et al., "Diverse and potent activities of HGF/SF in skin wound repair", Journal of Pathology, vol. 203, 2004, pp. 831-838, in 8 pages.
Brock, W.B. et al., "Temporary closure of open abdominal wounds: the vacuum pack", The American Surgeon, Jan. 1995, vol. 61(1), pp. 30-35, abstract, in 6 pages.
Chariker, M.E. et al., "Effective Management of Incisional and Cutaneous Fistulae with Closed Suction Wound Drainage", Contemporary Surgery, vol. 34, Jun. 1989, pp. 59-63, in 5 pages.
Columbia Electronic Encyclopedia, The: the effect of body temperature on wound healing, printed Jan. 16, 2009, in 3 pages. URL: http://encyclopedia2.thefreedictionary.com/body+temperature.
Dilmaghani, A. et al., "A Method for Closed Irrigation and Suction Therapy in Deep Wound Infections," Journal of Bone and Joint Surgery, 1969, vol. 51-A, No. 2, pp. 323-342, in 20 pages.
Fleischmann, W. et al. "Vacuum Sealing for Treatment of Soft Tissue Injury in Open Fractures," Emergency Surgery (1993), vol. 96, pp. 488-492, in 5 pages.
Garner, G. et al., "Vacuum-assisted wound closure provides early fascial reapproximation in trauma patients with open abdomens," Am. J. of Surgery, vol. 182 (2001), pp. 630-638, in 9 pages.
Harris, D., "A new technique of skin grafting using Stei-Greffe and a self-adhering foam pad," Brit. J. of Plastic Surg., vol. 34, No. 2, Apr. 1981, pp. 181-185, in 6 pages.
Hartz, R.S. et al., "Healing of the Perineal Wound", Arch. Surg., Apr. 1980, vol. 115, pp. 471-474, in 4 pages.

INSTECH Model P720 Peristaltic Pump Operation Manual, Dec. 1997, pp. 1-11, in 7 pages.
International Preliminary Report for International Application No. PCT/GB2004/004566, dated Feb. 12, 2005 in 7 pages.
International Preliminary Reporton Patentability, re PCT Application No. PCT/GB2004/004566, dated Dec. 13, 2005.
International Search Report, re PCT Application No. PCT/GB2004/004566, dated Feb. 23, 2005.
International Preliminary Reporton Patentability, re PCT Application No. PCT/GB2004/004567, dated Dec. 13, 2005.
International Search Report, re PCT Application No. PCT/GB2004/004567, dated Feb. 21, 2005.
International Preliminary Reporton Patentability, re PCT Application No. PCT/GB2005/001612, dated Nov. 1, 2006.
International Search Report, re PCT Application No. PCT/GB2005/001612, dated Jul. 27, 2005.
International Preliminary Report for International Application No. PCT/GB2005/004177 Date of Issuance of Report dated May 1, 2007 in 8 pages.
International Preliminary Report for International Application No. PCT/GB2006/03421, dated Mar. 18, 2008 in 7 pages.
International Search Report for International Application No. PCT/GB2006/03421, dated Feb. 20, 2007 in 3 pages.
International Preliminary Reporton Patentability, re PCT Application No. PCT/GB2006/003425, dated Mar. 18, 2008.
International Search Report, re PCT Application No. PCT/GB2006/003425, dated Dec. 11, 2006.
International Preliminary Reporton Patentability, re PCT Application No. PCT/GB2006/003416, dated Mar. 18, 2008.
International Search Report, re PCT Application No. PCT/GB2006/003416, dated Nov. 30, 2006.
Jeter, K. et al., "Managing Draining Wounds and Fistulae: New and Established Methods", Chronic Wound Care, 1990, pp. 240-246, in 7 pages.
KCI Licensing, "V.A.C. Abdominal Dressing System Advanced Management of the Open Abdomen," 2004, in 6 pages.
Kuznetsov, V.A. et al., "Vacuum and Vacuum-Sorption Treatment of Open Septic Wounds", in Second All-Union Conference "Wounds and Wound Infections" (Presentation Abstracts) (Moscow, USSR 1986) pp. 91-92, with English translation, in 5 pages.
Mitchell, R. et al., "Role of Stem Cells in Tissue Homeostasis", Pocket Companion to Robbins and Cotran Pathologic Basis of Disease, 7th Edition, 2006, in 3 pages.
Morykwas, M. J. et al., "Nonsurgical Modalities to Enhance Healing and Care of Soft Tissue Wounds", Journal of the Southern Orthopaedic Association, vol. 6, No. 4, Winter 1997, in 12 pages.
Navsaria, P.H. et al., "Temporary closure of open abdominal wounds by the modified sandwich-vacuum pack technique", British Journal of Surgery, 2003, vol. 90, pp. 718-722, in 8 pages.
Nicholas, J.M., "Options for Management of the Open Abdomen", Presentation from Emory University School of Medicine, Invited Speaker American College of Surgeons 32nd Annual Spring Meeting, General Session 12—Presentation and Panel Discussion on The Open Abdomen in General Surgery—How Do You Close the Abdomen When You Can't—Boston Marriott Copley Place Hotel, Boston, MA Apr. 26, 2004, in 66 pages.
Nursing75, "Wound Suction: Better Drainage with Fewer Problems", Nursing, vol. 5, No. 10, Oct. 1975, pp. 52-55, in 4 pages.
Orgill, D.P. et al., "Guidelines for Treatment of Complex Chest Wounds with Negative Pressure Wound Therapy", Wounds, A Compendium of Clinical Research and Practice, Suppl. B, Dec. 2004, pp. 1-23, in 26 pages.
Schein, M. et al., "The 'Sandwich Technique' in the Management of the Open Abdomen," British Journal of Surgery, 1986, vol. 73, May 1986, pp. 369-370, in 2 pages.
Smith, L. et al., "Vacuum Pack Technique of Temporary Abdominal Closure: A Four-Year Experience", The American Surgeon, Dec. 1997, pp. 1102-1108; vol. 63, No. 12.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

(56) References Cited

OTHER PUBLICATIONS

Solovev, V.A., "Treatment and Prevention of Suture Failures after Gastric Resection" (Dissertation Abstract) (S.M. Kirov Gorky State Medical Institute, Gorky USSR 1988).

Stewart, J., "World Wide Wounds—Next Generation of Products for Wound Management", 2002, in 13 pages.

Svedman, P., "Irrigation Treatment in Split-Thickness Skin Grafting of Intractable Leg Ulcers," Scand J. Plast. Reconstr. Surg., 19:211-213, 1985.

Svedman, P., "Irrigation Treatment of Leg Ulcers", The Lancet, Sep. 1983, pp. 532-534, in 3 pages.

Svedman, P., "A Dressing Allowing Continuous Treatment of a Biosurface", IRCS Med. Science: Biomed. Tech.; Clinic. Med.; Surg. and Transplantation, 1979, vol. 7, p. 221, in 1 page.

Svedman, P. et al., "A Dressing System Providing Fluid Supply and Suction Drainage Used for Continuous or Intermittent Irrigation", Annals of Plastic Surgery, vol. 17, No. 2, Aug. 1986, pp. 125-133, in 9 pages.

Swift, S. et al., "Quorum Sensing in Aeromonas hydrophila and Aeromonas salmonicida: Identification of LuxRI Homologs AhyRI and AsaRI and Their Cognate N-Acylhomoserine Lactone Signal Molecules," J. Bacteriol., 1997, vol. 179(17), pp. 5271-5281, in 12 pages.

Teder, H. et al., "Continuous Wound Irrigation in the Pig," Journal of Investigative Surgery, vol. 3, 1990, pp. 399-407, in 9 pages.

Tribble, D. E., "An Improved Sump Drain-Irrigation Device of Simple Construction", Archives of Surgery New York, vol. 105, Sep. 1972, in 4 pages.

Urschel, J.D. et al., "The Effect of Mechanical Stress on Soft and Hard Tissue Repair; A Review", *Br. Journ. Plast. Surg.*, 1988, 41, 182-186.

Vijanto, J. and J. Raekallio, Local Hyperalimentation of Open Wounds, Br. J. surg., 1976, 63, 427-430.

Westaby, S. et al., "A Wound Irrigation Device", The Lancet, Sep. 2, 1978, pp. 503-504, in 2 pages.

Wooding-Scott, M. et al., "No Wound is Too Big for Resourceful Nurses," RN, Dec. 1988, pp. 22-25, USA, in 4 pages.

International Preliminary Report on Patentability for International Application No. PCT/GB2004/004567, dated Apr. 28, 2006 in 8 pages.

\* cited by examiner

Section Through X-X

Section Through X-X

Section Through X-X

Section Through X-X

Section Through X-X

Section Through X-X

Schematic representation Exudialysis flow system

APPARATUS AND METHOD FOR WOUND CLEANSING WITH ACTIVES

CROSS-REFERENCE TO RELATED APPLICATIONS

This application is a continuation of U.S. application Ser. No. 14/311,182, filed Jun. 20, 2014, which is a continuation of U.S. application Ser. No. 12/976,935, filed Dec. 22, 2010, which is a continuation-in-part of U.S. application Ser. No. 10/576,263, filed Nov. 9, 2006, which is a U.S. National Phase of PCT International Application No. PCT/GB04/04566, filed on Oct. 28, 2004, designating the United States and published on May 26, 2005 as WO/2005/046761, which claims priority to Great Britain Patent Application No. 0325120.4, filed Oct. 28, 2003. U.S. application Ser. No. 12/976,935 is also a continuation-in-part of U.S. application Ser. No. 10/599,728 filed Nov. 3, 2008, which is a U.S. National Phase of PCT International Application No. PCT/GB2005/001612, filed on Apr. 27, 2005, designating the United States and published on Oct. 11, 2005 as WO/2005/105180, which claims priority to Great Britain Patent Application No. 0409443.9, filed Apr. 28, 2004. U.S. application Ser. No. 12/976,935 is also a continuation-in-part of U.S. application Ser. No. 12/066,578, filed Oct. 10, 2008, which is a U.S. National Phase of PCT International Application No. PCT/GB06/03421, filed on Sep. 15, 2006, designating the United States and published on Mar. 22, 2007 as WO/2007/031762, which claims priority to Great Britain Patent Application No. 0518825.5, filed Sep. 15, 2005. U.S. application Ser. No. 12/976,935 is also a continuation-in-part of U.S. application Ser. No. 12/066,730, filed Oct. 9, 2008, which is a U.S. National Phase of PCT International Application No. PCT/GB2006/003425, filed on Sep. 15, 2006, designating the United States and published on Mar. 22, 2007 as WO/2007/031765, which claims priority to Great Britain Patent Application No. 0518826.3, filed on Sep. 15, 2005. U.S. application Ser. No. 12/976,935 is also a continuation-in-part of U.S. application Ser. No. 12/066,585, filed Sep. 29, 2008, which is a U.S. National Phase of PCT International Application No. PCT/GB06/03416, filed on Sep. 15, 2006, designating the United States and published on Mar. 22, 2007 as WO/2007/031757, which claims priority to Great Britain Patent Application No. 0518804.4, filed Sep. 15, 2005. The disclosures of these prior applications are hereby incorporated by reference in their entireties and should be considered a part of this specification.

BACKGROUND OF THE INVENTION

Field of the Invention

The present invention relates to an apparatus and a medical wound dressing for aspirating, irrigating and/or cleansing wounds, and a method of treating wounds using such apparatus for aspirating, irrigating and/or cleansing wounds.

It relates in particular to such an apparatus, wound dressing and method that can be easily applied to a wide variety of, but in particular chronic, wounds, to cleanse them of materials that are deleterious to wound healing, whilst retaining, distributing, and/or adding materials that are beneficial in some therapeutic aspect, in particular to wound healing.

Description of the Related Art

Aspirating and/or irrigating apparatus therefor are known, and tend to be used to remove wound exudate during wound therapy. In known forms of such wound therapy, the offtake from the wound, especially when in a highly exuding state, is voided to waste, e.g. to a collection bag.

Materials deleterious to wound healing are removed in this way.

However, materials that are beneficial in promoting wound healing, such as growth factors, extracellular and cell matrix components and fragments thereof, and other physiologically active components of the exudate from a wound are lost to the site where they can be potentially of most benefit, i.e. the wound bed, when such therapy is applied.

Such known forms of wound dressing and aspiration and/or irrigation therapy systems often create a wound environment under the dressing that thus may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

SUMMARY OF THE INVENTION

Certain embodiments of the present invention are directed to aspirating and/or irrigating apparatus that may be used to remove wound exudate during wound therapy. In some embodiments of such wound therapy, aspiration and irrigation of the wound take place sequentially.

Each part of the therapy cycle is beneficial in promoting wound healing:

Aspiration applies a negative pressure to the wound, which is beneficial in itself in promoting wound healing by removing materials deleterious to wound healing with the wound exudate, reducing bacterial load, combating peri-wound oedema, increasing local blood flow to the wound and encouraging the formation of wound bed granulation tissue.

Irrigation cleanses wounds of materials that are deleterious to wound healing by diluting and moving wound exudate (which is typically relatively little fluid and may be of relatively high viscosity and particulate-filled).

Additionally, relatively little of beneficial materials involved in promoting wound healing (such as cytokines, enzymes, growth factors, cell matrix components, extracellular matrix components and fragments thereof, biological signalling molecules and other physiologically active components of the exudate) are present in a wound, and are not well distributed in the wound, i.e. they are not necessarily present in parts of the wound bed where they can be potentially of most benefit. These may be distributed by irrigation of the wound and thus aid in promoting wound healing.

The irrigant may additionally contain active materials or active amounts of material that are potentially or actually beneficial in respect of wound healing. These may be distributed by irrigation of the wound and thus aid in promoting wound healing. These benefits in promoting wound healing include the movement of materials that are beneficial in promoting wound healing, such as those mentioned above and the supply in the irrigant of active amounts of materials that are beneficial in promoting wound healing which pass into and/or through the wound in contact with the wound bed.

In embodiments where aspiration and irrigation therapy are applied sequentially to a wound, the two therapies, each of which is beneficial in promoting wound healing, can only be applied intermittently. Thus, the wound may lose the above mentioned known beneficial effects of aspiration therapy on wound healing, at least in part, while that aspiration is suspended during irrigation. Additionally, for a given aspirant flow, whilst materials that are potentially or actually deleterious in respect of wound healing are removed from wound exudate, the removal in a given time period of application of the total irrigate and/or aspirate therapy will normally be less effective and/or slower than with continuous application of aspiration.

Even less to be desired, is that while aspiration is not applied to the wound, wound exudate and materials deleterious to wound healing (such as bacteria and debris, and iron II and iron III and for chronic wounds proteases, such as serine proteases) may pool on the wound bed and hinder wound healing, especially in a highly exuding wound. The influx of local oedema will also add to the chronicity of the wound. This is especially the case in chronic wounds.

Depending on the relative volumes of irrigant and wound exudate, the mixed exudate-irrigant fluid and may be of relatively high viscosity and/or particulate-filled. Once it is present and has pooled, it may be more difficult to shift by the application of aspiration in a conventional sequential aspirate-irrigate-dwell cycle than with continuous simultaneous aspiration of the wound, owing to the viscosity and blockage in the system.

The wound may also lose the abovementioned beneficial effects of irrigation therapy on wound healing, at least in part, while that irrigation is suspended during aspiration. For a given irrigant flow, the cleansing of the wound and the distribution by irrigation of the wound of such beneficial materials and the supply in the irrigant of active amounts of materials that are beneficial in promoting wound healing in a given time period of application of the total irrigate and/or aspirate therapy when such therapy is in a conventional sequential aspirate-irrigate-dwell cycle will normally be less effective and/or slower than with continuous application of irrigation.

In certain embodiments of the present invention, simultaneous irrigation and aspiration is provided to overcome the aforementioned shortcomings of sequential aspiration and irrigation therapy. These embodiments of the present invention provide several advantages.

One is that application of an irrigant to a wound under simultaneous aspiration creates a wound environment that is exposed to the continuous beneficial effects of both aspects of the therapy for wound healing as opposed to the sequential intermittent application of irrigant flow and aspiration in known aspirating and/or irrigating apparatus.

The latter result in less than optimum performance of the body's own tissue healing processes, and slower healing and/or weaker tissue growth that does not have a strong three-dimensional structure adhering well to and growing from the wound bed. This is a significant disadvantage, in particular in chronic wounds. Thus, the use of certain embodiments of the apparatus aspirating, irrigating and/or cleansing wounds retains and enhances the beneficial effects of aspiration in respect of wound healing by continuous and preferably constant aspiration. These include removing materials deleterious to wound healing with the wound exudate, reducing bacterial load, combating peri-wound oedema and encouraging the formation of wound bed granulation tissue.

Preferred embodiments of the apparatus for aspirating, irrigating and/or cleansing chronic wounds apply a milder negative pressure than in conventional negative pressure therapy (which is too aggressive for the fragile tissues of many such wounds). This leads to increased patient comfort, and lessens the risk of inflammation of the wound. The removal of wound exudate in a given time period of application of the total irrigate and/or aspirate therapy will normally be more effective and/or faster than with a conventional sequential intermittent aspiration and/or irrigation therapy.

Even more desirably, since simultaneous aspiration and irrigation is applied to the wound, wound exudate and materials deleterious to wound healing (such as bacteria and debris, and iron II and iron III and for chronic wounds proteases) will not pool on the wound bed and hinder wound healing, especially in a highly exuding wound. This is especially important in chronic wounds. The resulting mixed exudate-irrigant fluid will usually be of relatively lower viscosity.

Because simultaneous aspiration and irrigation of the wound provides continuous removal at a constant relatively high speed, the fluid does not have to be accelerated cyclically from rest, and will be easier to shift than with known forms of aspiration and/or irrigation therapy systems with a conventional sequential aspirate-irrigate-dwell cycle. This will thus exert a greater net effect on the removal of adherent bacteria and debris. This is especially the case in those embodiments of the apparatus for aspirating, irrigating and/or cleansing wounds where there is an inlet manifold (as described in further detail hereinafter): (a) that covers and contacts most of the wound bed (b) with openings that deliver the fluid directly to the wound bed over an extended area.

In another embodiment, the apparatus for aspirating, irrigating and/or cleansing wounds is used for the delivery from cells or tissue of further materials that are beneficial in promoting wound healing, and not only for use to remove materials that are deleterious to healing from wound exudate during wound therapy. Examples of such materials include materials from cells or tissue, such as growth factors, extracellular matrix components and fragments thereof, selective proteases or fibrinolytic factors and combinations thereof.

In another embodiment, an apparatus for cleansing bodily fluids such as blood of deleterious materials, such as a dialysis unit or filtration device, is provided. Such an apparatus may comprise a means for fluid cleansing that is respectively a two- or single-phase system. In such apparatus the circulating fluid from the body passes through the means for fluid cleansing and materials deleterious to wound healing are removed.

It would be desirable to provide a system of therapy which can remove materials deleterious to wound healing from wound exudate, while being able to supply materials that are beneficial to wound healing.

Cells or tissue may be used to particular advantage for these purposes in the wound healing process. Means for fluid cleansing may use cells or tissue for cleansing exudate. Additionally, it may supply growth factors, cell matrix components, biological signalling molecules involved in wound healing and other physiologically active components to the wound, where they can be potentially of most benefit.

It thus would be desirable to provide a system of aspiration and irrigation therapy for a wound, which can remove wound exudate and materials deleterious to wound healing from contact with the wound bed, whilst simultaneously cleansing it and distributing materials that are beneficial in promoting wound healing across it, and supplying in the irrigant active amounts of materials that are beneficial in promoting wound healing which pass into and/or through the wound in contact with the wound bed, and further supplies fluids containing active amounts of materials that are beneficial in promoting wound healing from cells or tissue to pass into and/or through the wound in contact with the wound bed Dialysis is a known method of treating bodily fluids such as blood ex vivo, to cleanse them of materials that are deleterious to the body systemically. Removal of such materials by contact with the dialysate is the prime purpose of dialysis, whilst also retaining and/or adding materials such as blood, cells and proteins. Other materials that may have an additional positive therapeutic action are potentially lost to the system through the dialysis membrane, which is also permeable to them. The balance of such materials in the bodily fluid in recirculation may thus be further depleted.

It would be desirable to provide a system of therapy that can remove materials deleterious to wound healing from wound exudate, without substantially diluting materials that are beneficial in promoting wound healing, and whilst adding such materials to be in contact with the wound bed, and which can continuously supply and recirculate such materials to the wound simultaneously.

Dialysis for treating bodily fluids is also a systemic therapy, since the treated fluid is returned to within the body. This is in contrast to a topical therapy in which the treated fluid is recycled outside the body, e.g. to a wound. Most dialysis also requires large amounts either of bodily fluids, such as blood, or of dialysate, and consequently the relevant devices tend not to be portable.

In previous systems, vascular supply to, and aspiration or circulation in, tissue underlying and surrounding the wound is often compromised. Certain embodiments of the present invention provide a system of therapy that also promotes vascular supply to tissue underlying and surrounding a wound, and retains and supplies therapeutically active amounts of materials that are beneficial in reversing this effect and supplies such materials using cells or tissue whilst removing deleterious materials, thereby promoting wound healing.

According to one embodiment of the present invention, an apparatus for aspirating, irrigating and/or cleansing wounds is provided, comprising: (a) a fluid flow path, comprising a conformable wound dressing, having a backing layer which is capable of forming a relatively fluid-tight seal or closure over a wound and at least one inlet pipe for connection to a fluid supply tube, which passes through and/or under the wound-facing face, and (b) at least one outlet pipe for connection to a fluid offtake tube, which passes through and/or under the wound-facing face, the point at which the at least one inlet pipe and the at least one outlet pipe pass through and/or under the wound-facing face forming a relatively fluid-tight seal or closure over the wound; (c) a fluid reservoir connected by a fluid supply tube to an inlet pipe via optional means for supply flow regulation; (d) means for supplying physiologically active agents to the wound; and (e) at least one device for moving fluid through the wound dressing; characterized in that it comprises means for providing simultaneous aspiration and irrigation of the wound, such that fluid may be supplied to fill the flowpath from the fluid reservoir via the fluid supply tube (optionally via means for supply flow regulation) while fluid is aspirated by a device through the fluid offtake tube (optionally or as necessary via means for aspirate flow regulation).

According to another embodiment, the apparatus is characterized in that it permits recirculation of fluid, comprising (a) a fluid flow path, comprising (i) a conformable wound dressing, having a backing layer which is capable of forming a relatively fluid-tight seal or closure over a wound and (ii) at least one inlet pipe for connection to a fluid supply tube, which passes through and/or under the wound-facing face, and (b) at least one outlet pipe for connection to a fluid offtake tube, which passes through and/or under the wound-facing face, (i) the point at which the at least one inlet pipe and the at least one outlet pipe pass through and/or under the wound-facing face forming a relatively fluid-tight seal or closure over the wound, (ii) at least one inlet pipe being connected to a fluid recirculation tube, and at least one outlet pipe being connected to a fluid offtake tube; and (iii) a means for fluid cleansing having at least one inlet port connected to a fluid offtake tube and at least one outlet port connected to a fluid recirculation tube; (c) a fluid reservoir connected by a second fluid supply tube to an integer of the flow path (optionally or as necessary via means for flow switching between supply and recirculation); (d) a device for moving fluid through the wound dressing and means for fluid cleansing, and optionally or as necessary the fluid supply tube; (e) means for supplying physiologically active agents to the wound; and (f) optionally means for bleeding the flowpath such that fluid may be supplied to fill the flowpath from the fluid reservoir via the fluid supply tube (optionally or as necessary via the means for flow switching) and recirculated by the device through the flow path.

According to a still further embodiment, the physiologically active agents are from cells or tissue.

Where any pipe is described in connection with the apparatus as being connected or for connection to a (mating end of a) tube, e.g. a fluid supply tube, fluid recirculation tube or fluid offtake tube, the pipe and the tube may form a single integer in the flow path through which the circulating fluid from the wound passes.

Preferably any such apparatus is an automated, programmable system which can cleanse the wound irrigant and/or wound exudate with minimal supervision.

Described below are examples of components and characteristics that may be included in the apparatus.

Fluid Reservoir and Container(s)

In one embodiment, the apparatus for aspirating, irrigating and/or cleansing wounds may be provided with means for admitting fluids directly or indirectly to the wound under the wound dressing in the form of a fluid supply tube to a fluid reservoir. The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In embodiments of the apparatus, the type and material of the tubes throughout the apparatus for aspirating, irrigating and/or cleansing wounds and the container for cells or tissue and the fluid reservoir will be largely determined by their function. To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system dialysis (and/or aspiration and irrigation) unit, of the dialysate that moves into the circulating (and/or aspirating) fluid in the apparatus.

When in contact with irrigant fluid, it should not allow any significant amounts of extractables to diffuse freely out of it in use of the apparatus. It should be sterilizable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene. Suitable materials for the present purpose also include copolymers thereof, for example with vinyl acetate and mixtures thereof. Suitable materials for the present purpose further include medical grade poly(vinyl chloride). Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

In one embodiment, the means for supplying physiologically active agents from cells or tissue to the wound conveniently comprises (a) an irrigant reservoir connected to (b) a container that contains a cell or tissue component, in turn connected to (c) a supply tube into the flowpath. The supply of physiologically active agents from cells or tissue will often occur into the conformable wound dressing. In use, irrigant is passed from the reservoir through the container that contains the cells or tissue and exits from it containing one or more physiologically active component materials that are beneficial in promoting wound healing that are expressed by the cells or tissue. The modified irrigant (including such physiologically active agents as have been added from the cells or tissue) is moved by the device for moving fluid through the supply tube and dressing to the wound. Then in admixture with wound exudate it is moved along the flow path, through the offtake tube.

In another embodiment of the apparatus for irrigating, cleansing and/or aspirating wounds of the present invention, the means for supplying physiologically active agents from cells or tissue to the wound comprises (a) an irrigant reservoir, and (b) a container that contains a cell or tissue component, (c) both connected in parallel to a supply tube for supplying physiologically active agents from cells or tissue and irrigant to the wound under the action of at least one device for moving fluid through the wound. In this embodiment of the apparatus, the irrigant reservoir and the container that contains a cell or tissue component may be, e.g. connected to the supply tube by a Y-junction. In use, irrigant is passed from the reservoir to the supply tube, and a fluid (which may be a nutrient medium for the cells or tissue) containing one or more physiologically active component materials that are beneficial in promoting wound healing that are expressed by the cells or tissue is passed from the container that contains the cells or tissue to the supply tube. The irrigant in admixture with such physiologically active agents as have been added from the cells or tissue is moved by a device for moving fluid through the wound to and through the wound.

In yet another embodiment of the apparatus for irrigating, cleansing and/or aspirating wounds of the present invention, the means for supplying physiologically active agents from cells or tissue to the wound comprises (a) an irrigant reservoir, connected to (b) a first supply tube for supplying irrigant to the wound under the action of at least one device for moving fluid through the wound, and (c) a container that contains a cell or tissue component, connected to (d) a second supply tube for supplying physiologically active agents from the cells or tissue the wound dressing. In use, irrigant is passed from the reservoir to the first supply tube for supplying irrigant to the wound. The fluid containing one or more physiologically active component materials that are beneficial in promoting wound healing that are expressed by the cells or tissue is passed from the container that contains the cells or tissue to the second supply tube for supplying physiologically active agents from the cells or tissue to the wound dressing. Each is moved by a device for moving fluid through the wound to and through the wound. The irrigant is admixed in the wound space with the physiologically active agents that have been added from the cells or tissue.

In a further embodiment of the apparatus for irrigating, cleansing and/or aspirating wounds of the present invention, the means for supplying physiologically active agents from cells or tissue to the wound comprises (a) an irrigant reservoir connected to (b) a container that contains a cell or tissue component, under the backing layer, and which communicates with the wound via at least one channel or conduit for supplying physiologically active agents from cells or tissue and irrigant to the wound under the action of at least one device for moving fluid through the wound. The container that contains a cell or tissue component may be integral with the other components of the dressing, in particular the backing layer. Alternatively, it may be permanently or demountably attached to them/it, with an adhesive film, for example, or by heat-sealing. In use, irrigant is passed from the reservoir through the container that contains the cells or tissue and exits from it into the wound space under the backing layer proximal face containing one or more physiologically active component materials that are beneficial in promoting wound healing that are expressed by the cells or tissue.

In yet a further embodiment of the apparatus for irrigating, cleansing and/or aspirating wounds of the present invention, the means for supplying physiologically active agents from cells or tissue to the wound comprises (a) a first irrigant reservoir connected to (b) a supply tube for supplying irrigant to the wound under the action of at least one device for moving fluid through the wound, and (c) a second irrigant reservoir connected to (d) a container that contains a cell or tissue component, under the backing layer, and which communicates with the wound via at least one channel or conduit for supplying physiologically active agents from cells or tissue and irrigant to the wound under the action of at least one device for moving fluid through the wound. The container that contains a cell or tissue component may be integral with the other components of the dressing, in particular the backing layer. Alternatively, it may be permanently or demountably attached to them/it, with an adhesive film, for example, or by heat-sealing. In use, irrigant is passed from the first reservoir to the supply tube for supplying irrigant to the wound. Irrigant is also passed from the second reservoir to the container.

The fluid containing one or more physiologically active component materials that are beneficial in promoting wound healing that are expressed by the cells or tissue is passed from the container that contains the cells or tissue to the second supply tube for supplying physiologically active agents from the cells or tissue to the wound dressing. Each is moved by a device for moving fluid through the wound to and through the wound. The irrigant is admixed in the wound space with the modified irrigant containing physiologically active agents that have been added from the cells or tissue.

All of these embodiments of the means for supplying physiologically active agents from cells or tissue to the wound may use cells or tissues of two or more different types. In such systems, a first input cell or tissue type is often contained in a first container, and a second input cell or tissue type is often contained in a second container. The two input cell or tissue types and containers may feed physiologically active agents in parallel to the dressing and to the wound bed under the action of at least one device for moving fluid through the wound. In this embodiment of the apparatus, the containers that contain the cell or tissue components may be, e.g. connected to a single supply tube by a Y-junction, and thence to the wound dressing, or they may, e.g. be connected to it by separate supply tubes, the two flows of physiologically active agents from cells or tissue optionally with irrigant and/or nutrient medium for the cells being optionally mutually admixed in the wound space under the wound dressing.

In an alternative layout of this means for supplying physiologically active agents from cells or tissue to the wound, the first container, in which the first input cell or tissue type is contained, is in fluid communication in series with the second container, in which the second cell or tissue type is contained. Thus, they feed their physiologically active agents in series to the dressing and to the wound bed under the action of at least one device for moving fluid through the wound. In this layout of the means for supplying physiologically active agents from cells or tissue, the two containers effectively function as a single container.

As noted above, irrigant and/or nutrient medium for the cells or tissue is often fed through the containers of the cell or tissue components and thence to the wound dressing. In use, these layouts of the means for supplying physiologically active agents from cells or tissue to the wound will function in the apparatus exactly as for their analogs with a single cell or tissue type.

The container that contains a cell or tissue component is often in the form of a hollow body such as e.g. a canister, cartridge or cassette, with a chamber or compartment that contains a cell or tissue component, through which the irrigant and/or a nutrient medium for the cells or tissue is passed. Where the container that contains a cell or tissue component lies outside the backing layer, the structure will often be made of glass, and/or synthetic polymeric materials. For example, such a structure may be a glass cylinder defining a chamber with axial inlet and outlet ports for throughflow, which contains cells or tissue on a scaffold. Where the container that contains a cell or tissue component lies under the backing layer, the structure will often be made of a conformable synthetic polymeric material. Such a structure may still be a structure defining a chamber with an inlet port, which contains cells or tissue on a scaffold, and which communicates with the wound via at least one channel or conduit. The latter is/are for supplying physiologically active agents from cells or tissue and irrigant to the wound under the action of at least one device for moving fluid through the wound.

Where the container that contains a cell or tissue component is integral with the other components of the dressing, in particular the backing layer, it will usually be of the same polymeric material as the components. Where, alternatively, it is permanently or demountably attached to them/it, with an adhesive film, for example, or by heat-sealing, it may be of a different polymeric material. It may contain a cell or tissue component that is not bound to an insoluble and immobilised substrate over and/or through which the irrigant and/or wound exudate from the wound dressing passes.

Any such structure may contain a cell or tissue component that is not bound to an insoluble and immobilised substrate over and/or through which the irrigant and/or wound exudate from the wound dressing passes. It then also appropriately comprises two or more integers which are permeable to the wound exudate or a mixture with irrigant, but have apertures, holes, openings, orifices, slits or pores of sufficiently small cross-dimension to hold the cell or tissue component, and to retain particulates, e.g. cell debris, in the hollow body. Each of the integers may then effectively form a macroscopic and/or microscopic filter.

Alternatively, it may contain a cell or tissue component that is bound to an insoluble and immobilised substrate over and/or through which the irrigant and/or wound exudate from the wound dressing passes, e.g. a scaffold. This will often be of a material that is not (cyto)toxic and is biocompatible and inert to any components that are beneficial in promoting wound healing, including natural and synthetic polymeric materials. This may typically be in the form of a conformable film, sheet or membrane, often with apertures, holes, openings, orifices, slits or slots of small cross-dimension. It may then effectively form a structure which is a mesh, grid, lattice, net or web.

The container for cells or tissue need not comprise two or more integers which are permeable to the wound exudate or a mixture with irrigant to hold the cell or tissue component in the hollow body, but they may be desirable to retain particulates, e.g. cell debris.

The integer that contains the tissue or cell component will normally be mounted within a device constructed to maintain the viability and activity of the cells. This would include but not be limited to means for supplying nutrition and regulating the exchange of gases and maintaining an optimum temperature. The means for supplying nutrition may comprise a conventional nutrient medium for the cells or tissue containing one or more physiologically active component materials that are beneficial in promoting cell proliferation in the cells or tissue in the container that contains the cells or tissue and/or the expression by such cells or tissue of one or more physiologically active component materials that are beneficial in promoting wound healing.

To achieve therapeutically effective amounts of materials that are beneficial in promoting wound healing, a fluid flow though and/or over the cells or tissue may have to be maintained over multiple cycles, with significant dwell times and/or over significant periods of time.

Thus, in those embodiments of the means for supplying physiologically active agents from cells or tissue to the wound described above, the container that contains a cell or tissue component may be provided with (a) means for recycling nutrient medium for the cells or tissue from and back to a nutrient medium reservoir, e.g. a loop comprising the reservoir, connected to the container that contains the cells or tissue, with a pump, and in particular (b) means for switching fluid flow between recycling around the loop comprising the reservoir and the container and supply to the relevant supply tube.

Such means for switching fluid flow may comprise at least one one-way valve in the loop and in the fluid supply tube, or a two-way valve connecting the supply tube and the loop. In use, nutrient medium for the cells or tissue is recycled from and back to a nutrient medium reservoir in the loop comprising the reservoir and the container that contains the cells or tissue, with a pump, over multiple cycles, with significant dwell times and/or over significant periods of time until the cell proliferation in the cells or tissue in the container that contains the cells or tissue and/or the expression by such cells or tissue of one or more physiologically active component materials that are beneficial in promoting wound healing have achieved the desired levels.

Recycling nutrient medium for the cells or tissue from and back to the nutrient medium reservoir is then stopped, and supply to the relevant supply tube is started. This may be achieved by stopping the pump and/or closing a one-way valve in the loop and opening on in the supply tube, or by switching a two way valve connecting the supply tube and the loop. The necessary desired levels of physiologically active component materials, valves, pumps, number of cycles, dwell times and/or time periods will be apparent to the skilled person.

Physiologically Active Materials

In certain embodiments, the apparatus for irrigating, cleansing, and/or aspirating wounds includes a means for supplying physiologically active components to the wound to promote wound healing.

The present form of aspiration and/or irrigation therapy systems creates a wound environment for better distribution of materials that are beneficial in some therapeutic aspect, in particular to wound healing, that are present in a wound, but may not be well distributed in the wound, e.g. in a highly exuding wound. (These include cytokines, enzymes, growth factors, extracellular cell matrix components and fragments thereof, biological signalling molecules and other physiologically active components of the exudate.) and/or materials in the irrigant that are potentially or actually beneficial in respect of wound healing such as those noted below in this regard, e.g. growth factors and other physiologically active materials. These may aid wound cell proliferation and new tissue growth that has a strong three-dimensional structure adhering well to and growing from the wound bed. This is a significant advantage, in particular in chronic wounds. This is especially the case in those embodiments of the apparatus for aspirating, irrigating and/or cleansing wounds where there is an inlet manifold as described below. This covers and contacts most of the wound bed with openings that deliver the fluid directly to the wound bed over an extended area.

Simultaneous aspiration and irrigation of the wound provides advantages over topical bolus instillation, such as the pooled delivery of fluid to the wound bed by the application of a conventional sequential aspirate-irrigate-dwell cycle. These include (in addition to greater bioavailability to all areas of the wound surface as above), prolonged delivery between dressing changes and optimal dosing. In the latter case, sequentially irrigating and aspirating a wound means the need to flood the wound with one or more static fluid physiologically active component in higher dosage concentration than is necessary to achieve a therapeutically active level of such actives on the wound bed. This is just to maintain a desired average therapeutically active level of such actives on the wound bed during the dwell time period of sequentially irrigating and aspirating a wound, since these dosage concentrations levels tend to drop during this dwell time period in the cycle.

It will be seen that normally the level of such actives is effectively reduced to zero by the conventional sequential subsequent aspiration of the wound. Less desirably, it has been observed that some of such physiologically active components, for example factors such as TGFβ show different effects at high and low concentrations. An unnecessarily high dose to ensure activity during the residence between typical bolus instillations in conventional sequential irrigation-aspiration of the wound may result in less than optimum dosing and performance of the body's own tissue healing processes. Even less desirably, some of such physiologically active components may have adverse effects at higher concentrations. An unnecessarily high dose to ensure activity during the residence between typical bolus instillations in conventional sequential operation may result in undesirable effects on the wound bed. All of this may result in slow healing and/or slowing down of the healing and growth lacking a strong three-dimensional structure adhering well to and growing from the wound bed. This is a significant disadvantage, in particular in chronic wounds.

Application of a positive pressure to the wound under the backing layer may make it possible to flood the tissue underlying the wound with one or more physiologically active components in therapeutically active amounts. This may promote greater wound healing than by treatment with static fluid physiologically active component(s) alone or by sequential intermittent application of irrigant flow and aspiration. This may however provide an apparatus for wound therapy that is less convenient and flexible in assembly, handling and disassembly.

The prolonged delivery of such physiologically active components in therapeutically active amounts in a precise and time-controlled manner by simultaneous aspiration and irrigation, together with (a) the removal of materials deleterious to wound healing from wound exudate, (b) without substantially diluting materials, or the continuous supply of materials, that are beneficial in promoting wound healing (including such materials that have been added using cells or tissue) in contact with the wound bed, and (c) the continuously supply and recirculation of such materials to the wound, promotes greater wound healing than (i) by treatment with the fluid physiologically active component(s) alone, or (ii) by topical bolus delivery in known aspirating and irrigating apparatus. Advantages over topical bolus delivery include greater bioavailability to all areas of the wound surface, prolonged delivery between dressing changes and optimal dosing. For example, factors such as TGFβ show different effects at high and low concentrations. Consequently, undesirable effects may be the result of an unnecessarily high dose to ensure prolonged residence between topical applications. It is believed that by using the apparatus for irrigating and/or aspirating wounds cyclically and/or with reversal of flow, the effects may be further enhanced.

As described in further detail hereinafter, elements beneficial to wound healing may be biochemical, e.g. enzymatic or physical antagonists to elements detrimental to wound healing in the exudate and/or exudate and irrigant. The supply of such physiologically active materials may be effected at any appropriate point for this purpose along the apparatus flow path. It is often convenient to effect such supply to the wound via the fluid passing or in recirculation through the wound dressing from irrigant in the fluid reservoir that contains them.

Thus, one embodiment of the apparatus for irrigating, cleansing and/or aspirating wounds is characterized in that it comprises an irrigant fluid in the fluid reservoir which in turn comprises one or more physiologically active components in amounts to promote wound healing. Examples of such components (however supplied, and under a positive or negative pressure on the wound bed) include: (a) autologous, allogeneic or xenogeneic blood or blood products, such as platelet lysates, plasma or serum; (b) natural purified protein or recombinant-produced protein growth factors, such as platelet derived growth factor (PDGF), vascular endothelial growth factor (VEGF), transforming growth factor alpha (TGFα) or transforming growth factor beta (TGFβ-1, 2 or 3), basic-fibroblast growth factor (b-FGF also known as FGF2), epidermal growth factor (EGF), granulocyte-macrophage colony-stimulating factor (GM-CSF); insulin like growth factor-1 (IGF-1) and keratinocyte growth factor 2 KGF2 (also known as FGF7); (c) natural purified protein or recombinant produced protein cytokines such as the interleukin 1β (IL1β), or interleukin 8 (IL-8) and other physiologically active agents whether present normally in acute or chronic wounds, that can be augmented in the irrigant fluid to be of benefit to the wound bed, when such therapy is applied, and combinations thereof.

An additional embodiment of the apparatus for irrigating, cleansing and/or aspirating wounds is characterized in the physiologically active components in amounts to promote wound healing comprise materials that are beneficial in promoting wound healing by removing materials or by regulating, limiting or inhibiting processes deleterious to wound healing from wound exudate. This confers an advantage over the wound dressings in use before the present invention with means for supplying physiologically active agents under conventional sequential aspiration and irrigation of the wound. In these, the physiologically active agents are often supplied to the wound bed through a foam, which acts as a baffle to reduce the rate of diffusion, thus creating a concentration gradient of the physiologically active agents from a high concentration at the inlet point on the dressing to a low concentration at the wound bed. It is therefore difficult to predict the concentration of actives at the wound bed. This effect is exacerbated by a counter-flow of exudate from the wound bed.

Many such dressings with means for supplying physiologically active agents to the wound bed also have a concentration gradient of the physiologically active agents across the wound bed from a high concentration at the inlet point to a low concentration at the outlet point. It is therefore difficult to supply a uniform concentration of actives across the wound bed.

The inlet manifold in the wound dressings used in certain embodiments of the present invention covers and contacts most of the wound bed with openings that deliver the fluid directly to the wound bed over an extended area, and therefore reduces the concentration gradient. It is thus easy to predict the concentration of actives at the wound bed, and there tends to be no counter-flow of exudate from the wound bed. It is also easy to supply a uniform concentration of actives across the wound bed.

Moving wound fluid aids in movement of biological signalling molecules involved in wound healing (including such materials that have been added using cells or tissue) to locations in the wound bed that are favourable to wound healing and/or to cells that would otherwise not be exposed to them, e.g. in a highly exuding wound. This is especially the case in those embodiments of the apparatus for aspirating, irrigating and/or cleansing wounds where there is an inlet manifold that delivers the fluid directly to the wound bed over an extended area. Such materials include cytokines, enzymes, nutrients for wound cells to aid proliferation, oxygen, and other molecules that are beneficially involved in wound healing (including such materials that have been added using cells or tissue), such as growth factors, and others having beneficial effects (which may be further enhanced) in causing chemotaxis.

It is foreseen that the actives to be added to the wound bed may be the nutrient medium, that human or mammalian cells e.g. keratinocytes, fibroblast or a mixture of these cells, or others for instance, have grown in (conditioned media). The cells will release beneficial actives to the media e.g. TGFβ that would benefit the wound bed and aid healing of the wound.

In some embodiments of the present invention the actual cells themselves with or without the cells growth media, maybe used as an active to the wound bed to aid healing. In particular embodiments of the present invention different types of cells may be used as actives at different times of the healing process. For example, fibroblast type cells maybe used as an active to the wound bed to aid healing initially in order to help would remodelling and aid the wound to lay down structural fibres. Then keratinocytes or a larger proportion of keratinocytes than initially used before could be used as an active flowing along the wound bed to aid healing. Other cells could be used as well or combination thereof. It is foreseen that the cells (keratinocytes or fibroblasts) can aid healing of the wound by giving beneficial healing components or by sticking to the wound bed and aiding healing directly.

When conditioned media is used, (the media that has had cells grown in it) different conditioned media from different cell source may be used and it is envisaged that having a particular order to which conditioned media to use may be important and aid healing. For example, conditioned media from fibroblast type cells or a mixture of cells comprising a high proportion of fibroblast cells may be used initially followed by a conditioned media from keratinocyte type cells or a mixture of cells comprising a higher proportion of keratinocyte than used before. It is foreseen that this will aid healing of the wound.

The irrigant supplied to the wound dressing under a negative or positive pressure on the wound bed may alternatively or additionally, where appropriate, contain nutrients for wound cells to aid proliferation or migration or the synthesis of matrix components or factors beneficial to wound healing, such as sugars, amino acids, purines, pyrimidines, vitamins, metal ions or minerals, or any such ingredients that may be found in either serum containing or serum-free cell culture medium or might be used as nutritional supplements.

The irrigant supplied to the wound dressing under a negative or positive pressure on the wound bed may alternatively or additionally, where appropriate, contain medicaments, such as antimicrobials, examples of which include antibacterial agents, for example triclosan, iodine, metronidazole, cetrimide, chlorhexidine acetate; antifungal agents, for example sodium undecylenate, chlorhexidine, iodine or clotrimoxazole; antibiotics such as ciprofloxacin or clindamycin.

The irrigant supplied to the wound dressing under a negative or positive pressure on the wound bed may alternatively or additionally, where appropriate, include local analgesics/anaesthetics, such as lignocaine, bupivicaine, or diclofenac to reduce wound pain or pain associated with the dressing.

The irrigant supplied to the wound dressing under a negative or positive pressure on the wound bed may alternatively or additionally, where appropriate, supply materials to achieve the delivery of nucleic acid molecules as active genes or gene-containing vectors (DNA, RNA or modified versions thereof), as naked molecules, molecules complexed with nucleic acid binding carriers, molecules within liposomes or as virus vectors to give steady, measured delivery of gene therapeutic molecules to wound bed cells.

In the means for supplying physiologically active agents from cells or tissue to the wound, the irrigant from the reservoir that passes into and through the cell or tissue component often conveniently comprises cell culture medium species, e.g. trace elements and/or other nutrients such as amino acids, sugars, low molecular weight tissue building blocks, purines, pyrimidines, vitamins, metal ions or minerals, and/or gases, such as air, nitrogen, oxygen and/or nitric oxide, to aid proliferation of the cells or tissue in the means and/or steady, measured expression and supply of physiologically active agents.

In such case, materials that are listed above are also suitable therapeutic molecules to supply to wound bed cells to aid proliferation of the cells or tissue, and/or which are otherwise beneficial to wound healing. In such case, it may be desirable to provide a system in which the irrigant from the reservoir that passes into and through the cell or tissue component comprises cell culture medium species and thereafter is supplied to the wound bed via a supply tube into the flowpath wherever appropriate, so that such cell culture medium species pass with the irrigant to the wound bed.

The irrigant from the reservoir may be used to maintain an optimum temperature of the cells or tissue and/or for regulating the exchange of gases in a conventional manner apparent to the skilled person. It is necessary for such a system to also irrigate the wound at a practical rate with the physiologically active components in therapeutically active amounts. Automated, programmable systems which can regulate the wound irrigant parameters and functions listed above in a precise and time-controlled manner are amongst those that are particularly suitable for use.

The tissue component may be an ex vivo (autologous, allogeneic or xenogenic) uncultured tissue explant. Alternatively the tissue component may be formed from separated or partially separated cells which have either been used without a period of culture or they may have been cultured in vitro. The process of culture may involve growth and proliferation or just incubation in culture. The source tissues may be tissue from any organ such as skin, muscle, bone, neural, connective tissue, intestinal, liver or amniotic tissue and other organs or combinations thereof, whose cells and tissue retain the appropriate properties. The cells or tissue may be fully viable or viable, but rendered non-dividing through irradiation or chemical treatment, or rendered non-viable after an appropriate period of culture. Alternatively, the cells or tissue may be genetically modified to increase production of a particular material, e.g. a protein that is beneficial in promoting wound healing, such as a growth factor, an extracellular matrix component or fragments thereof, and other physiologically active components, or a biochemical, e.g. enzymatic or physical antagonists to elements detrimental to wound healing in the exudate and/or exudate and irrigant.

The tissue component that provides the active material that acts beneficially on the wound bed and/or cleanses the exudate and/or exudate and irrigant of materials detrimental to wound healing may consist of a co-culture. A co-culture encompasses the in vitro or ex vivo culture of two or more cell types or tissue explants. This might be with one or both input cells or tissues fully viable or viable, but rendered non-dividing, through irradiation or chemical treatment, or rendered non-viable after an appropriate period of culture. Exudate cleansing may be provided where the input cells or tissues are intimately mixed or intermingled, or they may be present as layers one on the other.

Alternatively, the cells or tissue may be genetically modified to increase production of a particular material, e.g. a protein that is beneficial in promoting wound healing, such as a growth factor, an extracellular matrix component or fragments thereof, and other physiologically active components, or a biochemical, e.g. enzymatic or physical antagonists to elements detrimental to wound healing in the exudate and/or irrigant. The input cells or tissues may be intimately mixed or intermingled, or they may be present as layers one on the other.

In some systems a semi permeable membrane or matrix between the component cells or tissues allows communication through biochemicals or proteins or other signals, but no cell apposition between the input cell types. In further systems modified irrigant or conditioned medium is collected from one input cell or tissue type and given to the second input cell or type and given back to the first input cell type (sequentially or continuously) to generate the optimal output or cleansing actions.

The cell or tissue component may be activated either singly or repeatedly through the delivery of biochemical, protein, enzymatic or physical means or through electromagnetic irradiation, ultrasonic or electrical stimulation.

The conduits through which respectively (a) the irrigant and/or wound exudate passes from the wound dressing and (b) the cleansed fluid, (c) still containing materials from the wound that are beneficial in promoting wound healing, (d) with added elements beneficial to wound healing to the exudate and irrigant (or modified irrigant), and/or (f) modified through biochemical, enzymatic or physical means to contain elements beneficial to wound healing, is returned to the recirculation tube, and (d) (in the case where the means is provided in the form of a two-phase system, such as an dialysis unit) through which the cleansing fluid enters and exits the means preferably have means for, on module disconnection and withdrawal, (i) switching off the flow and (ii) providing an immediate fluid-tight seal or closure over the ends of the conduits and the cooperating tubes in the rest of the apparatus so exposed, to prevent continuing passage of irrigant and/or exudate and cleansed fluid, and cleansing fluid.

Moving Fluid Through the Wound

The apparatus for aspirating, irrigating, and/or cleansing comprises a device for moving fluid through the wound. This device may be any appropriate for this purpose, and may act at any appropriate point for this purpose. It may apply a positive or negative pressure to the wound, although its prime purpose is to move fluid (irrigant from the fluid reservoir and/or wound exudate through the length of the apparatus flow path, rather than to apply a positive or negative pressure to the wound. If applied to the fluid in recirculation in the fluid recirculation tube upstream of and towards the wound dressing and/or the fluid in the fluid supply tube towards the wound dressing (optionally or as necessary via means for flow switching between supply and recirculation), it will usually apply positive pressure (i.e. above-atmospheric pressure) to the wound bed.

Often the means for fluid cleansing is (most appropriately for its purpose) downstream of the wound dressing, and provides the highest resistance in the flow path. This is especially the case where the means for fluid cleansing is a single-phase system, e.g. with ultrafiltration through microapertures or micropores, thus enhancing applied positive pressure to the wound. Where the device is applied to the fluid in recirculation in the fluid recirculation tube and/or the fluid in the fluid offtake tube downstream of and away from the wound dressing, it will usually apply negative pressure (i.e. below-atmospheric pressure or vacuum) to the wound bed.

The following types of pump may be used as desired: (a) reciprocating pumps, such as: (i) shuttle pumps—with an oscillating shuttle mechanism to move fluids at rates from 2 to 50 ml per minute; (ii) diaphragm pumps—where pulsations of one or two flexible diaphragms displace liquid while check valves control the direction of the fluid flow; (iii) piston pumps—where pistons pump fluids through check valves, in particular for positive and/or negative pressure on the wound bed; (b) rotary pumps, such as: (i) centrifugal pumps; (ii) flexible impeller pumps—where elastomeric impeller traps fluid between impeller blades and a moulded housing that sweeps fluid through the pump housing; (iii) progressing cavity pumps—with a cooperating screw rotor and stator, in particular for higher-viscosity and particulate-filled exudate; (iv) rotary vane pumps—with rotating vaned disk attached to a drive shaft moving fluid without pulsation as it spins. The outlet can be restricted without damaging the pump; (v) peristaltic pumps—with peripheral rollers on rotor arms acting on a flexible fluid circulation tube to urge fluid current flow in the tube in the direction of the rotor; (c) vacuum pumps—with pressure regulators.

The type and/or capacity of the device will be largely determined by (a) the appropriate or desired fluid volume flow rate of irrigant and/or wound exudate from the wound, and (b) whether it is appropriate or desired to apply a positive or negative pressure to the wound bed, and the level of such pressure to the wound bed for optimum performance of the wound healing process, and by factors such as portability, power consumption and isolation from contamination. Such a device may also suitably be one that is capable of pulsed, continuous, variable, reversible and/or automated and/or programmable fluid movement. It may in particular be a pump of any of these types.

In practice, even from a wound in a highly exuding state, such a rate of exudate flow is only of the order of up to 75 microlitres/cm$^2$/hr (where cm$^2$ refers to the wound area), and the fluid can be highly mobile (owing to the proteases present). Exudate levels drop and consistency changes as the wound heals, e.g. to a level for the same wound that equates to 12.5-25 microlitres/cm$^2$/hr.

Where materials deleterious to wound healing are removed by a two-phase system (see below.), such as a dialysis unit, fluid is also potentially lost to the system through the means for fluid cleansing. This may occur, e.g. through a dialysis polymer film, sheet or membrane which is also permeable to water, in addition to materials deleterious to wound healing. The balance of fluid in recirculation may thus further decrease, but may be adjusted to minimise this undesired loss in a routine manner as described hereinbefore. Hence, it will be seen that the circulating fluid from the wound will typically contain a preponderance of irrigant over wound exudate in recirculation from the fluid reservoir.

The type and/or capacity of the device will thus be largely determined in this respect by the appropriate or desired fluid volume flow rate of irrigant, rather than that of exudate, from the wound. In practice, such a rate of flow of total irrigant and/or wound exudate will be of the order of 1 to 1000, e.g. 3 to 300, and less preferably 1 to 10 ml/cm$^2$/24 hour, where the cm$^2$ refers to the wound area. The volume of irrigant and/or wound exudate in recirculation may vary over a wide range, but will typically be e.g. 1 to 8 1. (for example for large torso wounds), 200 to 1500 ml (for example for axillary and inguinal wounds), and 0.3 to 300 ml for limb wounds when the therapy is applied in this way.

In practice, suitable pressures are of the order of up to 25% atm such as up to 10% atm. positive or negative pressure on the wound bed, the apparatus being operated as a closed recirculating system. The higher end of these ranges are potentially more suitable for hospital use, where relatively high % pressures and/or vacua may be used safely under professional supervision. The lower end is potentially more suitable for home use, where relatively high % pressures and/or vacua cannot be used safely without professional supervision, or for field hospital use.

The device may be a peristaltic pump or diaphragm pump, e.g. preferably a small portable diaphragm or peristaltic pump. These are preferred types of pump, in order in particular to reduce or eliminate contact of internal surfaces and moving parts of the pump with (chronic) wound exudate, and for ease of cleaning. It may suitably be one that applies positive pressure to the wound and/or the means for fluid cleansing. A preferred pump when the applied pressure is positive is a peristaltic pump, e.g. a small, portable peristaltic pump, mounted upstream of the means for fluid cleansing.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

The pump may suitably be one that applies negative pressure to the wound and/or the means for fluid cleansing. A preferred pump when the applied pressure is negative is a diaphragm pump, e.g. a small, portable diaphragm pump, mounted downstream of the dressing or the means for fluid cleansing.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

The outlet from the dressing passes to the means for fluid cleansing for removal of materials deleterious to wound healing from wound exudate, and in turn to the fluid recirculation tube(s).

The means for providing simultaneous aspiration and irrigation of the wound often comprises a (first) device for moving fluid through the wound applied to fluid downstream of and away from the wound dressing, in combination with at least one of a second device for moving fluid through the wound applied to the irrigant in the fluid supply tube upstream of and towards the wound dressing; means for aspirate flow regulation, connected to a fluid offtake tube, and means for supply flow regulation, connected to a fluid supply tube. The (first) device will apply negative pressure (i.e. below-atmospheric pressure or vacuum) to the wound bed. It may be applied to the aspirate in the fluid offtake tube downstream of and away from the wound dressing.

Alternatively or additionally, where appropriate, the aspirate in the fluid offtake tube downstream of the wound dressing may be aspirated into a collection vessel, and the first device may act on fluid such as air from the collection vessel. The (first) device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve.

Alternatively, where appropriate the (first) device for moving fluid through the wound may be a variable-throughput device, such as a variable-speed pump, downstream of the wound dressing, thus effectively forming a combination of a (first) device for moving fluid through the wound with means for aspirate flow regulation and/or means for supply flow regulation in a single integer. The (first) device for moving fluid through the wound will often be a pump of any of the following types, or a piped supply of vacuum, applied to fluid downstream of and away from the wound dressing. In the case of any pump it may be a fixed-speed pump, with (as above) a discrete means for aspirate flow regulation, connected to a fluid offtake tube, and/or means for supply flow regulation, connected to a fluid supply tube, in each case, e.g. a regulator, such as a rotary valve. Alternatively, where appropriate the pump may be a variable-throughput or variable-speed pump.

The following types of pump may be used as the (first) device: (a) reciprocating pumps, such as (i) piston pumps—where pistons pump fluids through check valves, in particular for positive and/or negative pressure on the wound bed; and (ii) diaphragm pumps—where pulsations of one or two flexible diaphragms displace fluid with check valves; and (b) rotary pumps, such as: (i) progressing cavity pumps—with a cooperating screw rotor and stator, in particular for higher-viscosity and particulate-filled exudate; and (ii) vacuum pumps—with pressure regulators.

The (first) device may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning. Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

Where any second device is applied to the fluid in the fluid supply tube upstream of and towards the wound dressing, it will usually apply positive pressure (i.e. above-atmospheric pressure) to the wound bed. As with the (first) device, it may be a fixed-throughput device, such as a fixed-speed pump, which will usually require a discrete means for supply flow regulation, connected to a fluid supply tube, e.g. a regulator, such as a rotary valve.

Alternatively, where appropriate the second device for moving irrigant fluid to the wound may be a variable-throughput device, such as a variable-speed pump, upstream of the wound dressing, thus effectively forming a combination of a second device for moving fluid through the wound with means for supply flow regulation in a single integer.

The second device for moving fluid through the wound will often be a pump of any of the following types applied to the irrigant in the fluid supply tube upstream of and towards the wound dressing. It may be a fixed-speed pump, with (as above) a discrete means for supply flow regulation, connected to a fluid supply tube, e.g. a regulator, such as a rotary valve. Alternatively, where appropriate the pump may be a variable-throughput or variable-speed pump. The following types of pump may be used as the second device: (a) reciprocating pumps, such as (i) shuttle pumps—with an oscillating shuttle mechanism to move fluids at rates from 2 to 50 ml per minute; and (b) rotary pumps, such as: (i) centrifugal pumps, (ii) flexible impeller pumps—where elastomeric impeller traps fluid between impeller blades and a moulded housing that sweeps fluid through the pump housing; (iii) peristaltic pumps—with peripheral rollers on rotor arms acting on a flexible fluid aspiration tube to urge fluid current flow in the tube in the direction of the rotor; (iv) rotary vane pumps—with rotating vaned disk attached to a drive shaft moving fluid without pulsation as it spins. The outlet can be restricted without damaging the pump.

The second device may be a peristaltic pump, e.g. preferably a small portable peristaltic pump. This is a preferred type of pump, in order in particular to reduce or eliminate contact of internal surfaces and moving parts of the pump with irrigant, and for ease of cleaning. Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

Each such pump of any these types may also suitably be one that is capable of pulsed, continuous, variable and/or automated and/or programmable fluid movement. Less usually and less preferably, each such pump of any these types will be reversible. As above, the means for supply flow regulation may be a regulator, such as a rotary valve. This is connected between two parts of a fluid supply tube, such that the desired supply flow regulation is achieved.

If there are two or more inlet pipes, these may be connected to a single fluid supply tube with a single regulator, or to first, second, etc. fluid supply tubes, respectively having a first regulator, a second regulator, etc., e.g. a valve or other control device for admitting fluids into the wound. As above, the means for aspirate flow regulation may be similarly provided in a form in which concomitant aspirate flow regulation is possible. It may be a regulator, such as a valve or other control device, e.g. a rotary valve. Multiple offtake tubes may be similarly provided with single or multiple regulators, all for aspiration of fluids from the apparatus, e.g. to a aspirate collection vessel, such as a collection bag.

If there is no second device for moving fluid through the wound applied to the irrigant in the fluid supply tube upstream of and towards the wound dressing, it is only possible to apply a negative pressure to the wound, by means of the device for moving fluid through the wound applied to the aspirate in the fluid offtake tube downstream of and away from the wound dressing.

Operation may e.g. be carried out at a negative pressure of up to 50% atm., typically at a low negative pressure of up to 20% atm., more usually up to 10% atm. at the wound, as is described hereinafter. Examples of suitable and preferred (first) devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Alternatively, if it is desired to apply a net positive pressure to the wound, the means for providing simultaneous aspiration and irrigation of the wound must comprise not only a first device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Operation may then e.g. be carried out at a positive pressure of up to 50% atm., typically at a low positive pressure of up to 20% atm., more usually up to 10% atm. at the wound, as is described hereinafter. Examples of suitable and preferred first devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning. Examples of suitable and preferred second devices include those types of pump that are so described hereinbefore in relation to the second device. This may be a peristaltic pump, e.g. a miniature peristaltic pump. This is a preferred type of pump, in order to eliminate contact of internal surfaces and moving parts of the pump with irrigant in the fluid supply tube upstream of and towards the wound dressing, and for ease of cleaning.

It is of course equally possible to apply a negative pressure to the wound, by means of such a combination of a first device for moving fluid through the wound applied to the aspirate in the fluid offtake tube downstream of and away from the wound dressing, and a second device for moving fluid through the wound applied to the irrigant in the fluid supply tube upstream of and towards the wound dressing; optionally with means for supply flow regulation, connected to a fluid supply tube; means for aspirate flow regulation, connected to a fluid offtake tube.

Indeed, as noted below in this regard, preferred embodiments of the apparatus for aspirating, irrigating and/or cleansing chronic wounds that apply a negative pressure include such types of combination of a first device, e.g. a diaphragm pump, e.g. preferably a small portable diaphragm pump, and a second device, e.g. a peristaltic pump, preferably a miniature peristaltic pump, as described hereinbefore in relation to the device for moving fluid through the wound.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

The higher end of the ranges of % positive and negative pressure noted above are potentially more suitable for hospital use, where they may only be used safely under professional supervision. The lower end is potentially more suitable for home use, where relatively high % positive and negative pressures cannot be used safely without professional supervision, or for field hospital use. In each case, the pressure on the wound may be held constant throughout the desired length of therapy, or may be varied cyclically in a desired positive or negative pressure regime.

As noted above, when it is desired to apply a negative pressure to the wound, it is preferred that the means for providing simultaneous aspiration and irrigation of the wound comprise not only a (first) device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Accordingly, one embodiment of the apparatus for irrigating, cleansing and/or aspirating wounds of the present invention is characterized in the means for providing simultaneous aspiration and irrigation of the wound comprises a (first) device for moving fluid through the wound applied to fluid downstream of and away from the wound dressing, and a second device for moving fluid through the wound applied to the irrigant in the fluid supply tube upstream of and towards the wound dressing, and in combination with at least one of means for supply flow regulation, connected to a fluid supply tube, and means for aspirate flow regulation, connected to a fluid offtake tube.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

This combination of (a) a device for moving fluid through the wound applied to the aspirate in the fluid offtake tube downstream of and away from the wound dressing, and (b) a device for moving fluid through the wound applied to the fluid in the fluid supply tube upstream of and towards the wound dressing, (c) may be used to apply an overall positive or negative, or even zero pressure to the wound. At least one body in the flow path to, over and from the wound bed should have sufficient resilience against the pressure to allow any significant compression or decompression of the fluid occur.

Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials. It will be seen that the balance of fluid between aspirated fluid from the wound and irrigant supplied to the wound from the fluid means for supplying physiologically active agents from cells or tissue to the wound, e.g. the reservoir will thus be largely determined by a means for providing simultaneous aspiration and irrigation of the wound which is a system comprising: (a) means for aspirate flow regulation and/or a device for moving fluid through the wound applied to fluid downstream of and away from the wound dressing, and (b) means for supply flow regulation and/or a device for moving fluid through the wound applied to the fluid in the fluid supply tube upstream of and towards the wound dressing.

The appropriate flow rate through the supply tube will depend on a number of factors, such as the components of the irrigant and/or wound exudate, the relative volumes of irrigant and wound exudate (a) the viscosity and consistency of each of the irrigant, exudate and mixed exudate-irrigant fluid, and any changes as the wound heals; (b) the level of negative pressure on the wound bed, (c) whether the irrigant in the fluid supply tube upstream of and into the wound dressing is under positive pressure, and the level of such pressure; (d) the level of any pressure drop between the irrigant in the fluid supply tube upstream of the wound dressing and the wound bed, such as across a porous element, e.g. a membrane wound contact layer on the lower surface of an inlet manifold that delivers the fluid directly to the wound bed; means for supply flow regulation; and/or a second device for moving fluid through the wound applied to the fluid in the fluid supply tube upstream of and towards the wound dressing; (e) the depth and/or capacity of the wound and (f) the power consumption needed for a given desired fluid volume flow rate of irrigant and/or wound exudate through the wound.

It may also depend on the level of any pressure drop between the irrigant in the fluid supply tube upstream of the wound dressing and the wound bed, such as across a porous element, e.g. a membrane wound contact layer on the lower surface of an inlet manifold that delivers the fluid directly to the wound bed; means for supply flow regulation; and/or a second device for moving fluid through the wound applied to the fluid in the fluid supply tube upstream of and towards the wound dressing.

The dressing may comprise an inlet manifold (as described in further detail hereinafter) that covers and contacts most of the wound bed with openings that deliver the fluid directly to the wound bed over an extended area, in the form of one or more inflatable hollow bodies defined by a film sheet or membrane. The (usually small) positive pressure above atmospheric from the irrigation device when both devices are running together should be sufficient to inflate the manifold. The (usually small) positive pressure above atmospheric in the manifold from the irrigation device when both devices are running together should be sufficient to inflate the manifold.

The desired fluid volume flow rate of irrigant and/or wound exudate is preferably that for optimum performance of the wound healing process. The flow rate will usually be in the range of 1 to 1500 ml/hr, such as 5 to 1000 ml/hr, e.g. 15 to 300 ml/hr, such as 35 to 200 ml/hr through the supply tube. The flow rate through the wound may be held constant throughout the desired length of therapy, or may be varied cyclically in a desired flow rate regime.

In practice, the offtake rate of flow of total irrigant and/or wound exudate will be of the order of 1 to 2000, e.g. 35 to 300 ml/24 hr/cm$^2$, where the cm$^2$ refers to the wound area, depending on whether the wound is in a highly exuding state.

In practice, the rate of exudate flow is only of the order of up to 75 microlitres/cm$^2$/hr (where cm$^2$ refers to the wound area), and the fluid can be highly mobile or not, depending on the level of proteases present). Exudate levels drop and consistency changes as the wound heals, e.g. to a level for the same wound that equates to 12.5-25 microlitres/cm$^2$/hr.

It will be seen that the aspirated fluid from the wound will typically contain a preponderance of irrigant from the means for supplying physiologically active agents from cells or tissue, or the fluid reservoir, to the wound over wound exudate.

The necessary adjustments to maintain the desired balance of fluid by means of (a) the means for aspirate flow regulation and/or downstream device, and (b) the means for supply flow regulation and/or upstream device for moving fluid (c) will be apparent to the skilled person, bearing in mind that as noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

The type and/or capacity of (a) a suitable first device for moving fluid through the wound applied to the aspirate in the fluid offtake tube downstream of and away from the wound dressing and/or (b) a suitable second device for moving fluid through the wound applied to the irrigant in the fluid supply tube upstream of and towards the wound dressing and/or will be largely determined by (i) the appropriate or desired fluid volume flow rate of irrigant and/or wound exudate from the wound, and (ii) whether it is appropriate or desired to apply a positive or negative pressure to the wound bed, and the level of such pressure to the wound bed for optimum performance of the wound healing process, and by factors such as portability, power consumption and isolation from contamination.

As noted above, when it is desired to apply a negative pressure to the wound with the apparatus for aspirating, irrigating and/or cleansing wounds to provide simultaneous aspiration and irrigation of the wound, the means for providing simultaneous aspiration and irrigation of the wound may comprise a single device for moving fluid through the wound applied to the aspirate in the fluid offtake tube downstream of and away from the wound dressing or in combination with at least one of means for supply flow regulation, connected to a fluid supply tube, and means for aspirate flow regulation, connected to a fluid offtake tube.

As noted above, the device may be a fixed-throughput device, such as a fixed-speed pump, which will usually require a discrete means for aspirate flow regulation, connected to a fluid offtake tube, e.g. a regulator, such as a rotary valve, or a variable-throughput device, such as a variable-speed pump, downstream of the wound dressing, thus effectively forming a combination of a device for moving fluid through the wound with means for aspirate flow regulation in a single integer.

Conformable Dressing

In certain embodiments of the apparatus for aspirating, irrigating and/or cleansing wounds, a particular advantage is the tendency of the wound dressing to conform to the shape of the bodily part to which it is applied.

The wound dressing comprises (a) a backing layer with a wound-facing face which is capable of forming a relatively fluid-tight seal or closure over a wound; (b) at least one inlet pipe for connection to a fluid supply tube or recirculation tube, which passes through and/or under the wound-facing face; and (c) and at least one outlet pipe for connection to a fluid offtake tube, which passes through and/or under the wound-facing face; (d) the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 20% atm., e.g. up to 10 atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound. Examples of such include a substantially flat film, sheet or membrane, or a bag, chamber, pouch or other structure of the backing layer, e.g. of polymer film, which can contain the fluid. The backing layer may be a film, sheet or membrane, often with a (generally uniform) thickness of up to 100 micron, preferably up to 50 micron, more preferably up to 25 micron, and of 10 micron minimum thickness. Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound. Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes. They may be hydrophilic, and thus also include hydrophilic polyurethanes. They also include thermoplastic elastomers and elastomer blends, for example copolymers, such as ethyl vinyl acetate, optionally or as necessary blended with high-impact polystyrene. They further include elastomeric polyurethane, particularly polyurethane formed by solution casting. Preferred materials for the present wound dressing also include thermoplastic elastomers and curable systems.

The backing layer is capable of forming a relatively fluid-tight seal or closure over the wound and/or around the inlet and outlet pipe(s). However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound. This may, e.g. be a pressure-sensitive adhesive, if that is sufficient to hold the wound dressing in place in a fluid-tight seal around the periphery of the wound-facing face of the wound dressing. Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable). This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose. Examples of such means include light switchable adhesives, as above, to secure the dressing in place to prevent leakage. Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip. Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way. Such means may each be laid out over the wound dressing to extend beyond the periphery of the backing layer of the wound dressing.

The dressing will, as appropriate, be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound. Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined. The flange or lip is concave on its proximal face to define a peripheral channel or conduit. It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound. The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

It may however be beneficial for the backing layer of the wound dressing as hereinbefore defined to extend from the generally round periphery of the wound dressing to define an arm that extends radially from the wound center when the dressing is in use and covers the inlet and outlet pipes. This form of the dressing provides the opportunity for coupling and decoupling the irrigant supply remote from the dressing and the wound in use. An example is depicted in FIGS. 20 and 21.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

In an embodiment of the present invention there is provided a conformable wound dressing. In one embodiment, the conformable wound dressing is characterized in that it comprises a backing layer with a wound-facing face which is capable of forming a relatively fluid-tight seal or closure over a wound and has (a) at least one inlet pipe for connection to a fluid supply tube, which passes through and/or under the wound-facing face, and (b) at least one outlet pipe for connection to a fluid offtake tube, which passes through and/or under the wound-facing face, (c) the point at which the or each inlet pipe and the or each outlet pipe passes through and/or under the wound-facing face forming a relatively fluid-tight seal or closure over the wound.

The dressing is advantageously provided for use in a bacteria-proof pouch.

Embodiments of the present invention may also include: (a) a suction head having a first face; (b) a second face opposite said first face, wherein said second face is comprised of a plurality of projections, said projections defining a plurality of channels for facilitating flow of fluids to an opening in said second face and through said first face, wherein said opening is adapted for connection to a suction tube; and (c) a surgical drape having an aperture coincident said opening, said surgical drape extending over a region, and overlapping beyond the perimeter of said first face, and wherein said surgical drape comprises a flexible adhesive coated film adhered to said region of said first face and a release-coated backing extending over said second face and adhered to the overlapping portion of said surgical drape.

For distributing fluid across a wound surface, certain embodiments of the present invention may also include: (a) a suction head having a first face; (b) a second face opposite said first face; (c) a plurality of projections coincident from said second face, wherein said projections form a contact surface with the wound surface, and wherein a plurality of channels for facilitating flow of fluids are defined between said projections, said channels remaining out of contact with the wound surface; and (d) an aperture in fluid communication with said channels formed by said projections and formed through said first face and second face.

Embodiments of the present invention may also comprise: (a) a method of using a therapeutic apparatus for stimulating the healing of wounds in mammals comprising the steps of (i) inserting a porous pad into or on said wound such that said porous pad is in contact with said wound, wherein said porous pad has at least a partial outer surface and an inner body, said outer surface being adapted for contact with surface of said wound with small first pores no larger than about 100 microns in diameter to enhance biocompatibility; (ii) securing said porous paid within said wound with the dressing cover to maintain a negative pressure at the site of said wound; (iii) generating a negative pressure at said wound through said porous pad; and (iv) collecting fluids from said wound through said porous pad.

As noted above, in another embodiment of the apparatus for aspirating, irrigating and/or cleansing wounds, a particular advantage is that the means for supplying physiologically active agents from cells or tissue to the wound lies within the wound dressing. In use, irrigant is passed from the reservoir through the cells or tissue component for supplying physiologically active agents to the wound which lies within the wound dressing, and exits from it containing one or more physiologically active component materials that are beneficial in promoting wound healing that are expressed by the cells or tissue. The modified irrigant (including such physiologically active agents as have been added from the cells or tissue) in admixture with wound exudate is moved by the device for moving fluid through the offtake tube along the flow path.

The wound dressing backing layer, which is capable of forming a relatively fluid-tight seal or closure over a wound, and the wound bed define a wound space, which contains cells or tissue. As noted above for a separate container, the wound space may contain a cell or tissue component that is not bound to an insoluble and immobilised substrate over and/or through which the irrigant and/or wound exudate from the wound passes. It then also appropriately comprises two or more integers which are permeable to the wound exudate or a mixture with irrigant, but have apertures, holes, openings, orifices, slits or pores of sufficiently small cross-dimension to hold the cell or tissue component, and to retain particulates, e.g. cell debris, in the hollow body. Each of the integers may then effectively form a macroscopic and/or microscopic filter.

Alternatively, it may contain a cell or tissue component that is bound to an insoluble and immobilised substrate over and/or through which the irrigant and/or wound exudate from the wound passes, e.g. a scaffold. This will often be of a material, and may typically be in the form, noted above as amongst those that are suitable for such components of a separate container that contains a cell or tissue component.

The wound space may contain a cell or tissue component at any appropriate point in contact with the irrigant and/or wound exudate, and the component may be as appropriate, adhered or otherwise secured to any integer of the wound dressing, e.g. the dressing backing layer or a wound filler, or it may be a separate structure, permanently unattached.

It may often lie in contact with the wound bed. Where it does so, it may be advantageous if it is (a) bound to an insoluble and immobilised substrate over and/or through which the irrigant and/or wound exudate from the wound passes, or (b) not bound to an insoluble and immobilised substrate, but comprised in two or more integers which are permeable to the wound exudate or a mixture with irrigant, and (c) comprises a biodegradable mesh, grid, lattice, net or web, with apertures, holes, openings, orifices, slits or pores of small cross-dimension in contact with the wound bed.

The cell or tissue component in contact with continuously supplied and recirculated irrigant and/or wound exudate has the ability to add elements beneficial to wound healing to the irrigant, but the same elements also aid proliferation of wound bed cells into the apertures, holes, openings, orifices, slits or pores of small cross-dimension of the biodegradable mesh, grid, lattice, net or web, which is also beneficial to wound healing. The tissue component has the ability to elaborate or express materials beneficial to wound healing to the irrigant to modify the irrigant.

Wound Filler

As also mentioned herein, the backing layer that is applied may be any that is appropriate to the present system of therapy and permits a positive or negative pressure of up to 50% atm., more usually up to 25% atm. to be applied to the wound. It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss. Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer. This is favourably a resiliently flexible, e.g. elastomeric, and preferably soft, structure with good conformability to wound shape. It is urged by its own resilience against the backing layer to apply gentle pressure on the wound bed.

The wound filler may be integral with the other components of the dressing, in particular the backing layer. Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic. Preferred materials for the present wound dressing include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape. The film, sheet or membrane, often has a (generally uniform) thickness similar to that of films or sheets used in conventional wound dressing backing layers. That is, up to 100 micron, preferably up to 50 micron, more preferably up to 25 micron, and of 10 micron minimum thickness, and is often resiliently flexible, e.g. elastomeric, and preferably soft. Such a filler is often integral with the other components of the dressing, in particular the backing layer, or permanently attached to them/it, with an adhesive film, for example, or by heat-sealing, e.g. to a flange.

Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs.

Of course, if the backing layer is a sufficiently conformable and/or e.g. an upwardly dished sheet, the backing layer may lie under the wound filler, rather than vice versa. In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other. In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure, with apertures, holes, openings, orifices, slits or slots, or tubes, pipes, tubules or nozzles. It communicates with at least one inlet or outlet pipe through at least one aperture, hole, opening, orifice, slit or slot. The fluid contained in the hollow body may then be the circulating (and/or aspirating) fluid in the apparatus.

The hollow body or each of the hollow bodies then effectively forms an inlet pipe or outlet pipe manifold that delivers the circulating (and/or aspirating) fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound. Thus, for shallower wounds, examples of suitable wound fillers as a component of a wound dressing include ones that consist essentially of one or more conformable hollow bodies defining an inlet pipe and/or outlet pipe manifold that delivers the circulating (and/or aspirating) fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

Unless the wound filler under the backing layer effectively forms an inlet pipe or outlet pipe manifold with a direct connection between the inlet pipe(s) and outlet pipe(s) at the point at which they pass through and/or under the wound-facing face and the wound bed is present, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler is an open-cell foam with pores that may form such bores, channels, conduits, passages and/or spaces through the wound filler under the backing layer. Where the filler is or comprises one or more conformable hollow bodies defined by, for example a polymer film, sheet or membrane, it may be provided with means for admitting fluids to the wound bed under the wound dressing. These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that circulate (and/or aspirate) fluid in the wound when the dressing is in use, that are described hereinbefore, may be used under a wound filler under the backing layer.

In brief, suitable layouts include ones where one or both manifolds are (a) annular or toroidal (regular, e.g. elliptical or circular, or irregular), optionally with blind-bore, perforated radial tubes, pipes or nozzles, branching from the annulus or torus; and/or (b) in a meandering, tortuous, winding, zigzag, serpentine or boustrophedic (i.e. in the manner of a ploughed furrow) pattern, or (c) defined by slots in and apertures through layers attached to each other in a stack.

Inlet and Outlet Pipes

The apparatus for aspirating, irrigating, and/or cleansing comprises inlet and outlet pipes, or tubes, which carry the irrigating fluid to the wound and the aspirating fluid away from the wound.

The inlet and/or outlet tubes, the fluid recirculation tube and the fluid supply tube, etc. may be of conventional type, e.g. of elliptical or circular cross-section, and may suitably have a uniform cylindrical bore, channel, conduit or passage throughout their length. Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should be suitably thick enough to withstand any positive or negative pressure on them, in particular if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted below with regard to pumps, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension. They may then effectively form a macroscopic and/or microscopic filter for particulates including cell debris and micro-organisms, whilst allowing proteins and nutrients to pass through. Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s). The whole length of the apparatus for aspirating, irrigating and/or cleansing wounds should be microbe-impermeable once the wound dressing is over the wound in use.

The at least one inlet pipe or outlet pipe may be in the form of an aperture, such as a funnel, hole, opening, orifice, luer, slot or port for connection as a female member respectively to a mating end of (a) a fluid recirculation tube and/or fluid supply tube (optionally or as necessary via means for forming a tube, pipe or hose, or nozzle, hole, opening, orifice, luer, slot or port for connection as a male member respectively to a mating end of (b) a fluid recirculation tube and/or fluid supply tube (optionally or as necessary via means for flow switching between supply flow regulation and recirculation) or (c) a fluid offtake tube.

Where the components are integral they will usually be made of the same material (for which it will be understood that materials that are listed above are amongst those that are suitable). Where, alternatively, they are a push, snap or twist-lock fit, the may be of the same material or of different materials. In either case, materials that are listed above are amongst those that are suitable for all the components.

The at least one pipe will generally pass through, rather than under the backing layer. In such case, the backing layer may often have a rigid and/or resiliently inflexible or stiff area to resist any substantial play between the or each pipe and the or each mating tube, or deformation under pressure in any direction. It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid recirculation tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer. The wound dressing may not comprise any integer under the backing layer in the wound in use.

However, this may not provide a system to distribute irrigant over a sufficient functional surface area to irrigate the wound at a practical rate. To be suitable for use, in particular in chronic wound dialysis (and/or aspiration and irrigation), with relatively high concentrations of materials that are deleterious to wound healing, it may be advantageous to provide a system where wound irrigant and/or wound exudate may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the circulating (and/or aspirating) fluid directly to the wound bed via the apertures. Similarly, there is an outlet manifold from which tubules radiate and run to the wound bed to end in openings and collect the fluid directly from the wound bed. The pipes, etc. may radiate regularly or irregularly through the wound in use, respectively from the inlet or outlet manifold, although regularly may be preferred.

A more suitable layout for deeper wounds is one in which the pipes, etc. radiate hemispherically and concentrically, to the wound bed. For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the circulating (and/or aspirating) fluid directly to the wound bed or outlet pipe or collects the fluid directly from the wound respectively. It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound. Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix. Other suitable layouts for shallower wounds include one which have blind-bore, perforated inlet pipe or outlet pipe manifolds that circulate (and/or aspirate) fluid in the wound when the dressing is in use. One or both of these may be such a form, the other may be, e.g. one or more straight blind-bore, perforated radial tubes, pipes or nozzles.

A preferred form of inlet pipe or (less usually) outlet pipe manifold that delivers the aspirating fluid directly to the wound bed or collects the fluid directly from the wound respectively is one that comprise one or more conformable hollow bodies defined by a film, sheet or membrane, such as a bag, chamber, pouch or other structure, filled with the irrigant (or less usually) aspirate from the wound, passing through perforations, apertures, holes, openings, orifices, slits or slots in the film, sheet or membrane defining the hollow body or hollow bodies. These may be of small cross-dimension, so that they may then effectively form microperforations, microapertures or pores in a permeable integer, for example the polymer film, sheet or membrane.

This type of manifold for irrigation (more usually) provides the highest uniformity in the flow distribution of irrigant over the wound at a practical rate to be suitable for use, in particular in chronic wound aspiration and irrigation, and hence to provide a system where materials that are beneficial in promoting wound healing from cells or tissue, such as growth factors, extracellular cell matrix components and fragments thereof, and other physiologically active components of the exudate from a wound, are distributed more evenly under the dressing over the wound bed.

This type of manifold for irrigation (more usually) is noted below with regard to wound fillers under the backing layer, since it is a resiliently flexible, e.g. elastomeric, and soft, structure with good conformability to wound shape. It is urged by its own resilience against the backing layer to apply gentle pressure on the wound bed, and is therefore also capable of acting as a wound filler. The film, sheet or membrane, often has a (generally uniform) thickness similar to that of films or sheets used in conventional wound dressing backing layers.

Another suitable layout is one in which an inlet pipe and/or outlet pipe manifold that delivers the circulating (and/or aspirating) fluid directly to the wound bed or collects the fluid directly from the wound respectively via inlet and/or outlet tubes, pipes or tubules, and the inlet manifold and/or outlet manifold is formed by slots in layers permanently attached to each other in a stack, and the inlet and/or outlet tubes, pipes or tubules are formed by apertures through layers permanently attached to each other in a stack. (In FIG. 10a there is shown an exploded isometric view of such a stack, which is non-limiting.)

Sterilization, Buffering, and Anti-Deposition

It is desirable that the wound dressing and the interior of the apparatus for aspirating, irrigating and/or cleansing wounds is sterile. The fluid may be sterilized in the fluid reservoir and/or the rest of the system in which the fluid recirculates, or moves, including the means for fluid cleansing, by ultraviolet, gamma or electron beam irradiation (Excepted from this is the integer that contains the tissue or cell component, since this may adversely affect the viability and activity of the cells). This way, in particular reduces or eliminates contact of internal surfaces and the fluid with any sterilizing agent.

Examples of other methods of sterilization of the fluid also include e.g. the use of (a) ultrafiltration through microapertures or micropores, e.g. of 0.02 to 0.45 micron maximum cross-dimension, to be selectively impermeable to microbes; and (b) fluid antiseptics, such as solutions of chemicals, such as chlorhexidine and povidone iodine; metal ion sources, such as silver salts, e.g. silver nitrate; and hydrogen peroxide; although the latter involve contact of internal surfaces and the fluid with the sterilizing agent.

It may be desirable that the interior of the wound dressing, the rest of the system in which the fluid recirculates, or moves, and/or the wound bed, even for a wound in a highly exuding state, are kept sterile after the fluid is sterilized in the fluid reservoir, or that at least naturally occurring microbial growth is inhibited. Thus, materials that are potentially or actually beneficial in this respect may be added to the irrigant initially, and as desired the amount in recirculation increased by continuing addition. Examples of such materials include antibacterial agents (some of which are listed above), and antifungal agents. Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate. may be added to adjust the pH, as may local analgesics/anaesthetics, such as lidocaine/lignocaine hydrochloride, xylocaine (adrenoline, lidocaine) and/or anti-inflammatories, to reduce wound pain or inflammation or pain associated with the dressing.

It is also desirable to provide a system in which physiologically active components of the exudate that are beneficial to wound healing are not removed before or after the application of fluid cleansing, e.g. by the passive deposition of materials that are beneficial in promoting wound healing, such as proteins, e.g. growth factors. This may occur at any point in the flow path, e.g. in at least one inlet or outlet pipe through at least one aperture, hole, opening, orifice, slit or slot.

The deposition of materials that are beneficial in promoting wound healing may be combated as follows: (a) extra materials may be added to the irrigant initially, and as desired the amount in recirculation increased by continuing addition, or (b) a repellent coating may be used at any point or on any integer in the recirculation path in direct contact with the fluid, e.g. on the means for fluid cleansing or any desired tube or pipe. Examples of coating materials for surfaces over which the circulating (or aspirating) fluid passes include (a) anticoagulants, such as heparin, and (b) high surface tension materials, such as PTFE, and polyamides, (c) which are useful for growth factors, enzymes and other proteins and derivatives.

Recirculation and Fluid Bleeding

In certain embodiments the apparatus for aspirating, irrigating, and/or cleansing wounds further comprises means for recirculating fluid from the wound, in addition to means for directly supplying physiologically active materials to the wound. The means for flow switching between supply and recirculation may take any form that enables the wound simultaneously to be (a) put into communication with the fluid reservoir but (b) closed to the fluid recirculation tube, and (c) vice versa. Thus, if there is only one inlet pipe that passes through and/or under the wound-facing face of the wound dressing, the fluid reservoir or means for supplying physiologically active agents from cells or tissue to the wound is connected by the fluid supply tube to the flow path via means for flow switching as desired between a fluid recirculation tube or a fluid offtake or supply tube. In this case, the means for flow switching between supply and recirculation may be a regulator, such as a T-valve. This is connected in turn to two parts of a fluid recirculation tube or a fluid offtake tube and the fluid supply tube, such that the desired flow switching between supply and recirculation is achieved.

The means for supplying physiologically active agents from cells or tissue to the wound often comprises (a) an irrigant reservoir connected to (b) a container that contains a cell or tissue component, through which the irrigant is passed to form modified irrigant, in turn connected to a supply tube. If there are two or more inlet pipes, these may each be connected respectively to a fluid supply tube or fluid recirculation tube, respectively having a first regulator and a second regulator, such as a valve or other control device for admitting fluids into the wound.

Alternatively, if there are two or more inlet pipes, these may each be connected respectively to (a) a fluid supply tube, in turn connected to a means for supplying physiologically active agents from cells or tissue to the wound, and (b) a fluid recirculation tube, respectively having a first regulator and a second regulator, such as a valve or other control device for admitting fluids into the wound.

The desired flow switching between supply and recirculation is achieved by respectively having the first regulator open when the second regulator is shut, and vice versa.

The means for bleeding the flowpath may be situated in any appropriate part of the apparatus that is in contact with the irrigant and/or wound exudate, but is usually within the offtake and/or recirculation tubes. However, it is often as far downstream of and away from the reservoir and the fluid supply tube as possible, so that it may be used to prime the whole of the flowpath from the fluid reservoir via the fluid supply tube. It may be a regulator, such as a valve or other control device, e.g. a T-valve that is turned to switch between bleed and recirculation, for bleeding fluids from the apparatus, e.g. to a waste reservoir, such as a collection bag.

Alternatively, flow switching between supply and recirculation may not be desired, but rather concomitant bleeding and/or recirculation is desired. The latter may occur when the volume of irrigant and/or wound exudate in recirculation is increased by continuing addition to it of (a) wound exudate, and/or (b) fluid passing from a cleansing fluid through a selectively permeable integer, for example in a system such as a dialysis unit.

The means for bleeding the offtake and/or recirculation tubes may then be provided in the form of a regulator, such as a simple valve or other control device for admitting or blocking the passage of irrigant and/or exudate through a bleed line branching from the recirculation path. The means for fluid cleansing may as desired be a 'single-phase system'. In this, the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

Alternatively, where appropriate it may be provided in the form of a two-phase system, such as a dialysis unit, or a biphasic liquid extraction unit. In this, the circulating fluid from the wound and the fluid reservoir passes through a system in which the fluid recirculates in indirect or (less usually, direct) contact with a second fluid (dialysate) phase, more usually a liquid, in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

In use, typically, the means for flow switching between supply and recirculation tubes is set to admit fluid into the wound from the fluid reservoir but to close the wound to the fluid recirculation tube. Then, any means for bleeding the offtake and/or recirculation tubes are/is opened and the device for moving fluid through the wound and means for fluid cleansing is started.

The capacity of the apparatus flow path and the flow rate of irrigant and/or wound exudate from the wound will largely determine whether it is appropriate to run the device to prime the apparatus throughout the whole length of the apparatus flow path, i.e. to displace any existing fluid reservoir (often air) from the fluid recirculation path, and for how long it should be run. Typically, there is a preponderance of irrigant from the fluid reservoir over wound exudate in recirculation, so that use of the device for moving fluid through the wound is appropriate for this purpose. It is allowed to run until the apparatus is primed throughout the whole length of the apparatus flow path. Then, typically the means for bleeding the offtake and/or recirculation tubes is closed, and the means for flow switching between supply and recirculation tubes is set to close the wound to the fluid reservoir but to admit fluid into the wound from the fluid recirculation tube.

If the means for fluid cleansing is a two-phase system, such as a dialysis unit, or a biphasic extraction unit, the cleansing fluid is typically set in motion in contact with the surface of the selectively permeable integer, for example the polymer film, sheet or membrane. Of course, the cleansing fluid may less usually be static, and then this step is omitted.

As noted below in more detail, the volume of irrigant and/or wound exudate from the wound in recirculation may be increased by continuing addition to it of (a) wound exudate, and/or (b) fluid passing from a cleansing fluid through a selectively permeable integer, for example the polymer film, sheet or membrane of a two-phase system, such as an dialysis unit.

Additionally or alternatively, it may be desired to apply a negative pressure to the wound by means of a device for moving fluid through the wound and means for fluid cleansing applied to the fluid in recirculation in the fluid recirculation tube downstream of and away from the wound dressing. In such case, it may be desirable to provide a system in which concomitant bleeding and/or recirculation is possible, and to make the necessary adjustments to maintain the desired balance of fluid in recirculation by means of the means for bleeding the offtake and/or recirculation tubes. The volume of irrigant and/or wound exudate from the wound in recirculation may be decreased by continuing loss from it of fluid passing from a cleansing fluid through a selectively permeable integer, for example in a system such as a dialysis unit.

Additionally or alternatively, it may be desired to apply a positive pressure to the wound by means of a device for moving fluid through the wound and means for fluid cleansing applied to the fluid in recirculation in the fluid recirculation tube upstream of and towards the wound dressing. The means for flow switching between supply and recirculation may be similarly provided in a form in which concomitant supply and/or recirculation is possible, and to make the necessary adjustments to maintain the desired balance of fluid in recirculation by means of the means for flow switching.

It will be appreciated that where a positive or negative pressure is to be applied to the wound, at least one hollow body in the recirculation flow path to and from the wound bed should have sufficient resilience against the pressure to allow any significant compression or decompression of the irrigant fluid to occur.

In all embodiments of the apparatus, the type and material of such bodies (which are defined by a film, sheet or membrane) that are described by way of example herein to be suitable for use in certain embodiments of the present invention will be largely capable of this function.

Thus, examples of suitable materials for bodies defined by a film, sheet or membrane, such as inlet or offtake and/or recirculation tubes and structures such as bags, chambers and pouches, filled with irrigant fluid, e.g. the backing layer of the wound dressing are suitably elastically resilient thermoplastic materials that are potentially capable of this function when pressure is applied in this way.

It is believed that using the apparatus for aspirating, irrigating and/or cleansing wounds cyclically the effects may be further enhanced. Circulating wound fluid aids in movement of biological signalling molecules involved in wound healing (including such materials that have been added using cells or tissue) to locations in the wound bed that are favourable to the wound healing process and/or to cells that would otherwise not be exposed to them, e.g. in a highly exuding wound.

This is especially the case in those embodiments of the apparatus for aspirating, irrigating and/or cleansing wounds where there is an inlet or outlet manifold from which tubules radiate and run to the wound bed to end in openings that deliver and collect the fluid directly from the wound bed over an extended area. Such materials include cytokines, enzymes, nutrients for wound cells to aid proliferation, oxygen, and other molecules that are beneficially involved in wound healing (including such materials that have been added using cells or tissue), such as growth factors, and others having beneficial effects (which may be further enhanced) in causing chemotaxis.

Fluid Cleansing

In certain embodiments, the apparatus for aspirating, irrigating, and/or cleansing wounds may comprise a means for cleansing the fluid. The means for fluid cleansing may use cells or tissue for cleansing exudate. Often, it is in the form of a hollow body such as a container, e.g. a canister, cartridge or cassette, with a chamber or compartment that contains a cell or tissue component, through which the wound exudate or a mixture of wound exudate and irrigant (or modified irrigant) is passed and recirculated by the device through the flow path. The structures noted above will often be made of glass, and/or synthetic polymeric materials. For example, such a structure may be a glass cylinder defining a chamber with axial inlet and outlet ports for throughflow, which contains cells or tissue on a scaffold.

The circuit element that contains the tissue or cell component will normally be mounted within a device constructed to maintain the viability and activity of the cells. This would include but not be limited to the means for supplying nutrition and regulating the exchange of gases and maintaining an optimum temperature. As described in further detail hereinafter, the means for fluid cleansing may be a single or dual phase circuit element.

The tissue component has the ability to remove elements detrimental to wound healing or to modify the cellular elements of the wound bed through biochemical, enzymatic or physical means by the elaboration or the uptake of materials or the combination of both elaboration and uptake. It may also have the ability to add elements beneficial to wound healing to the exudate and irrigant (or modified irrigant) or to modify the exudate and irrigant through biochemical, enzymatic or physical means to contain elements beneficial to wound healing, as it is passed and recirculated by the device through the flow path.

The cells used in certain embodiments of the present invention may be hepatocytes, or any other suitable cell type known in the art.

Depending on the particular type of wound being treated and the particular cells or tissue used in the present apparatus for aspirating, irrigating and/or cleansing wounds, the deleterious materials to be removed may include (a) proteases, such as serine proteases, e.g. elastase and thrombin; cysteine proteases; matrix metalloproteases, e.g. collagenase; and carboxyl (acid) proteases; (b) inhibitors of angiogenesis such as thrombospondin-1 (TSP-1), Plasminogen activator inhibitor, or angiostatin (plasminogen fragment); (c) pro-inflammatory cytokines such as tumour necrosis factor alpha (TNFα) and interleukin 1 beta (IL-1β), and (d) inflammatories, such as lipopolysaccharides, and e.g. histamine.

Again, depending on the particular type of wound being treated and the particular cells or tissue used in the present apparatus for aspirating, irrigating and/or cleansing wounds, the beneficial materials to be added may include antagonists to the materials deleterious to wound healing in the wound exudate, such as, for example (a) enzymes or others, such as protease inhibitors, such as serine protease inhibitors, cysteine protease inhibitors; matrix metalloprotease inhibitors; and carboxyl (acid) protease inhibitors; (b) binders and/or degraders, such as anti-inflammatory materials to bind or destroy lipopolysaccharides, e.g. peptidomimetics. They further include peptides (including cytokines, e.g. bacterial cytokines, such as α-amino-γ-butyrolactone and L-homocarnosine); and other physiologically active components.

Examples of antagonists to such materials also include (a) natural purified protein, natural protein or recombinant-produced protein proteinase inhibitors, such as tissue inhibitors of metalloproteinases (TIMP 1 to 4) and alpha 1-antitrypsin (AAT), aprotinin, α-2-macroglogulin; (b) antibodies or chemically synthesised molecules at inappropriate levels that inhibit or inactivate processes or materials deleterious to wound healing from wound exudate, such as inhibitors of matrix metalloproteinases (MMPs), neutrophil elastase, inhibitors of inhibitors of new blood vessel formation (angiogenesis) such as thrombospondin or kallistatin; and combinations thereof.

The irrigant may alternatively or additionally, where appropriate, deliver a steady supply of natural purified protein, natural protein, or recombinant-produced protein debriding agents to remove and limit eschar, necrotic cells and tissues from the wound bed. Examples of such include stretoptokinase, plasmin, trypsin, collagenases, and other selective proteases or fibrinolytic factors and combinations thereof.

The irrigant supplied to the wound dressing, optionally under a positive pressure on the wound bed, may alternatively or additionally, where appropriate, contain materials added using cells or tissue, such as (a) antioxidants, such as ascorbic acid or stable derivatives thereof and (b) free radical scavengers, such as gutathione or natural purified proteins or recombinant-produced proteins such as superoxide dismutase (SOD) or (c) free radical generators (such as hydrogen peroxide) to balance the oxidative stress and oxidant potential of the wound bed in order to maximize the opportunity for wound healing.

The means for fluid cleansing may be (a) a single-phase system, such as an ultrafiltration unit, or a chemical absorption and/or adsorption unit; or (b) a two-phase system, such as a dialysis unit, or a biphasic extraction unit.

In the former, circulating fluid from the wound and the fluid reservoir passes through a self-contained system in which materials deleterious to wound healing are removed and the cleansed fluid, still containing materials that are beneficial in promoting wound healing are returned to the wound. No other fluid phase is supplied or passes into such means for fluid cleansing, and is recirculated by the device through the flow path back into the wound, with the possible exception of any fluid phase necessary to maintain the viability and activity of the cells, which could include but not be limited to means for supplying nutrition and regulating the exchange of gases and maintaining an optimum temperature, and/or to maintain the desired balance of fluid in recirculation.

Alternatively, where appropriate it may be provided in the form of a two-phase system. In this, the circulating fluid from the wound and the fluid reservoir passes through a system in which the fluid is not in contact with any cells that remove materials deleterious to wound healing, but recirculates in indirect or (less usually, direct) contact with a second fluid (dialysate) phase, more usually a liquid, which is in direct contact with the cell or tissue component that removes materials deleterious to wound healing.

The cleansed fluid, still containing materials from the wound that are beneficial in promoting wound healing, with added elements beneficial to wound healing to the exudate and irrigant (or modified irrigant), and/or modified through biochemical, enzymatic or physical means to contain elements beneficial to wound healing, is returned via the recirculation tube to the wound bed.

The first and second phases in such means for fluid cleansing are often separated by an integer which is permeable to materials deleterious to wound healing, such as a permeable or semi permeable membrane or matrix between the fluids that allows such materials to pass between the phases to and from the cell or tissue component. Such systems are described in further detail hereinafter.

In the two-phase system, the circulating fluid from the wound and the means for supplying physiologically active agents from cells or tissue to the wound passes through a system in which it is in indirect or (less usually, direct) contact with a second fluid (dialysate) phase.

Materials deleterious to wound healing are removed into the second phase, and the cleansed circulating fluid, still containing materials that are beneficial in promoting wound healing (including such materials that have been added using cells or tissue), is returned via the recirculation tube to the wound bed. Such systems are described in further detail hereinafter in connection with the means for fluid cleansing.

The means for fluid cleansing may as desired be a 'single-phase system'. The single-phase system may be of any conventional type.

Examples of the means for fluid cleansing in such a system include a macro- or microfiltration unit, which appropriately comprises one or more macroscopic and/or microscopic filters. These are to retain particulates, e.g. cell debris and micro-organisms, allowing proteins and nutrients to pass through.

Alternatively, they also include an ultrafiltration unit, such as a one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The membrane may preferably be of a hydrophilic polymeric material, such as a cellulose acetate-nitrate mixture, polyvinylidene chloride, and, for example hydrophilic polyurethane.

Examples of less preferred materials include hydrophobic materials also including polyesters, such as polycarbonates, PTFE, and polyamides, e.g. 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

The filter integer may be a flat sheet or a membrane of a polymeric material in a more convoluted form, e.g. in the form of elongate structure, such as pipes, tubules, etc.

The system may be a chemical adsorption unit, for example one in which a particulate, such as a zeolite, or a layer, e.g. of a functionalised polymer has sites on its surface that are capable of removing materials deleterious to wound healing on passing the circulating fluid from the wound and the fluid reservoir over them.

The materials may be removed, e.g. by destroying or binding the materials that are deleterious to wound healing, by, for example chelators and/or ion exchangers, degraders, which may be enzymes.

Examples of such also include less specific chemical adsorption units, for example one in which a physical absorbent, such as activated carbon or a zeolite, has non-specific sites on its surface that are capable of removing materials deleterious to wound healing on passing the circulating fluid from the wound and the fluid reservoir over them.

The cleansing integer, for example the polymer film, sheet or other chemical absorption and/or adsorption means, etc should of course be capable of removing materials deleterious to wound healing at a practical rate for a given capacity of the apparatus flow path and the flow rate of irrigant.

Alternatively, where appropriate the means for fluid cleansing may as desired be a 'two-phase system', such as a dialysis unit, or a biphasic liquid extraction unit. Where the apparatus for aspirating, irrigating and/or cleansing is provided with means for fluid cleansing is a single-phase system, it may be of any conventional type. In examples of the means for fluid cleansing that is a two-phase system, circulating fluid from the wound and the fluid reservoir in is indirect or (less usually, direct) contact with a second fluid (dialysate) phase, more usually a liquid, which is in direct contact with the cell or tissue component that removes materials deleterious to wound healing.

In the two-phase system, circulating fluid from the wound and the fluid reservoir in indirect or (less usually, direct) contact with a second fluid (dialysate) phase, more usually a liquid.

Thus, in one form, a biphasic liquid extraction unit, the second fluid phase is (usually) a liquid that is immiscible with the circulating fluid from the dressing, over a surface of which the circulating fluid passes in direct contact with the cleansing fluid. Materials deleterious to wound healing are removed into the dialysate, and the cleansed fluid, still containing materials that are beneficial in promoting wound healing, is returned via the recirculation tube to the wound bed.

Examples of such means for fluid cleansing include those wherein the second fluid (dialysate) phase is perfluorodecalin and like materials Alternatively, where appropriate it may be provided in a form in which the two fluids (recirculation fluid and dialysate) are separated by a significantly two-dimensional integer, for example a polymer film, sheet or membrane or hollow fibre or filament that is permeable to materials in the circulating fluid in the apparatus.

Again, materials deleterious to wound healing are removed into the dialysate, and the cleansed fluid, still containing materials that are beneficial in promoting wound healing is returned via the recirculation tube to the wound bed.

In either form in which the two-phase system, such as a dialysis unit, is provided, in use typically the dialysate moves past the circulating fluid in the apparatus in a co- or preferably counter-current direction. Pumps, such as peristaltic pumps, and/or valves control the direction of the two fluid flows. However, the cleansing fluid may less usually be static, although this may not provide a system with sufficient (dynamic) surface area to remove materials deleterious to wound healing from wound exudate at a practical rate.

Typical dialysate flow rates in a dialytic means for fluid cleansing in the present apparatus for aspirating, irrigating and/or cleansing wounds are those used in the conventional type of two-phase system, such as a dialysis unit for systemic therapy. The integer may be a film, sheet or membrane, often of the same type, and of the same (generally uniform) thickness, as those used in conventional two-phase system, such as a dialysis unit for systemic therapy. The film, sheet or membrane may be substantially flat, and depending on any pressure differential across it may require other materials on or in it to stiffen, reinforce or otherwise strengthen it.

However, this may not provide a system with sufficient functional surface area to remove materials deleterious to wound healing from wound exudate at a practical rate.

To be suitable for use, in particular in chronic wound dialysis, with relatively high concentrations of materials that are deleterious to wound healing, it may be advantageous to provide a system in which the film, sheet or membrane of a polymeric material is in a more convoluted form. This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid, still containing materials that are beneficial in promoting wound healing (including such materials that have been added using cells or tissue), is returned via the recirculation tube to the wound.

Where the means for fluid cleansing is a two-phase system, e.g. in the form of a dialysis unit, or a biphasic extraction unit, the circulating fluid from the wound and the container for cells or tissue and the fluid reservoir passes across one surfaces of a significantly two-dimensional integer, for example a polymer film, sheet or membrane which is selectively permeable to materials deleterious to wound healing.

These are removed by passing a cleansing fluid across the other surface of the integer. The integer may be a film, sheet or membrane that is selectively permeable to the foregoing materials deleterious to wound healing.

Examples of these as above include (a) oxidants, such as free radicals, e.g. peroxide and superoxide; (b) iron II and iron III; all involved in oxidative stress on the wound bed; (c) proteases, such as serine proteases, e.g. elastase and thrombin; cysteine proteases; matrix metalloproteases, e.g. collagenase; and carboxyl (acid) proteases; (d) endotoxins, such as lipopolysaccharides; (e) bacterial autoinducer signalling molecules, such as homoserine lactone derivatives, e.g. oxo-alkyl derivatives; (f) inhibitors of angiogenesis such as thrombospondin-1 (TSP-1), plasminogen activator inhibitor, or angiostatin (plasminogen fragment); (g) pro-inflammatory cytokines such as tumour necrosis factor alpha (TNF$\alpha$) and interleukin 1 beta (IL-1$\beta$); and (h) inflammatories, such as lipopolysaccharides, and e.g. histamine.

In this form in which the two-phase system, such as a dialysis unit, is provided, typically in use the dialysate moves past the circulating fluid in the apparatus in a co- or preferably counter-current direction. Pumps, such as peristaltic pumps, and/or valves control the direction of the two fluid flows. However, the cleansing fluid, which may be in direct contact with the cell or tissue component that removes materials deleterious to wound healing may less usually be static, although this may not provide a system with sufficient (dynamic) surface area to remove materials deleterious to wound healing from wound exudate at a practical rate. Typical dialysate flow rates in a dialytic means for fluid cleansing in the present apparatus for aspirating, irrigating and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy. The film, sheet or membrane may be substantially flat, and depending on any pressure differential across it may require other materials on or in it to stiffen, reinforce or otherwise strengthen it.

To be suitable for use, in particular in chronic wound dialysis, with relatively high concentrations of materials that are deleterious to wound healing, it may be advantageous to provide a system in which the film, sheet or membrane of a polymeric material is in a more convoluted form. This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid, still containing materials from the wound that are beneficial in promoting wound healing (including added elements beneficial to wound healing to the exudate and irrigant or modified irrigant), and/or modified through biochemical, enzymatic or physical means to contain elements beneficial to wound healing is returned via the recirculation tube to the wound.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly(methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO>25900 Dalton. The MWCO threshold can be varied to suit each application between 1 and 3000000 Dalton. Preferably, the MWCO should be as close as possible to this weight to exclude interference by larger competitor species.

For example, such a membrane with MWCO>25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate. The inhibitor, which is beneficial in promoting chronic wound healing, remains in contact with the wound bed, and can act beneficially on it, whilst the elastase that is deleterious to wound healing is removed.

Such use of the present apparatus is favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

Where it is desired to remove several different materials that are deleterious to wound healing, it may be advantageous to provide a system of modules in series, each of which removes a different material. This allows incompatible cleansing materials to be used on the same fluid and/or wound exudates.

Preferably any such system is a conventional automated, programmable system which can cleanse the wound irrigant and/or wound exudate with minimal supervision. As noted above in more detail, fluid passes from a cleansing fluid through a selectively permeable integer. This may be the typical permeable polymer film, sheet or membrane of a two-phase system, such as a dialysis unit. Additionally, solutes or disperse phase species will pass from the dialysate into the irrigant and/or wound exudate through the dialysis polymer film, sheet or membrane.

This property may be used to perfuse materials beneficial to wound healing into the irrigant and/or exudate from a dialysate. In this less conventional type of infusion feed, a broad spectrum of species will usually pass into the exudate and/or irrigant fluid from the dialysate.

It may be desired to provide a system of therapy which can remove materials deleterious to wound healing from wound exudate through cellular biochemical, enzymatic or physical means, while (a) retaining the relevant antagonists, for example degrading enzymes, or sequestrating agents, on the dialysate side of the membrane, (b) supplying such materials if they are beneficial to wound healing into the exudate and irrigant (or modified irrigant), and/or (c) supplying into the exudate and irrigant (or modified irrigant) other materials that are beneficial to wound healing and are expressed by the cell or tissue component that also removes materials deleterious to wound healing, or (d) are added elements beneficial to wound healing.

A particular advantage of option a) in the two-phase system, is where an antagonist that removes materials deleterious to wound healing from wound exudate is (cyto) toxic or bioincompatible, or not inert to any components that are beneficial in promoting wound healing.

The system does not allow any significant amounts of antagonist to diffuse freely out of the dialysate into the irrigant fluid. The active material can however act beneficially on the fluid.

As an example of option a), the antagonist to elastase, alpha-1-antitrypsin (AAT) (molecular weight 54000 Dalton) may occur in the dialysate or cell or tissue component and removes elastase (which is deleterious to wound healing). A membrane with MWCO>25900 Dalton does not allow any significant amounts of the inhibitor, which is beneficial in promoting chronic wound healing, to diffuse freely out of the dialysate and it remains there.

As an example of option b), a less conventional type of two-phase system may be used as the means for fluid cleansing. In this type, the polymer film, sheet or membrane is not an integer selectively permeable to materials deleterious to wound healing.

It will also permit a broad spectrum of components of the exudate from a wound and/or irrigant fluid that may be larger or smaller molecules, but are beneficially involved in wound healing to pass freely to and fro through it. Some species will pass from the dialysate to the irrigant and/or wound exudate and back.

The target materials deleterious to wound healing pass into the dialysate from the exudate through the non-selectively permeable polymer film, sheet or membrane. Unlike the other components of the exudate from a wound and/or irrigant fluid, the target materials deleterious to wound healing come into contact with the dialysate and/or antagonists, binders and/or degraders, and/or the cells or tissue optionally on an integer with at least one surface in the dialysate, and are removed by the appropriate antagonists, binders and/or degraders.

Thus, unlike the other components of the exudate from a wound and/or irrigant fluid the target materials are constantly removed from the dialysate, and very little of these species will pass from the dialysate into the irrigant and/or wound exudate. A steady state concentration equilibrium is not set up, even if the species are constantly 'topped up' from the wound dressing.

If (preferably) none of the dialysate is voided to waste, e.g. to a collection bag, a steady state concentration equilibrium of the untargeted species is eventually set up between the dialysate and the irrigant and/or wound exudate, which is 'topped up' from the wound dressing. Circulating wound fluid aids in removal from recirculation of the materials deleterious to wound healing from wound exudate, and in the quicker attainment of this equilibrium of these materials.

The cleansed fluid, still containing materials from the wound that are beneficial in promoting wound healing (including elements beneficial to wound healing added to the exudate and irrigant or modified irrigant), and/or modified through biochemical, enzymatic or physical means to contain elements beneficial to wound healing is returned to the recirculation tube and to the where materials beneficial in promoting wound healing can be potentially of most benefit, i.e. the wound bed.

Specifically, a membrane with MWCO>54000 Dalton will allow significant amounts of elastase that is deleterious to chronic wound healing to diffuse freely into the dialysate and eventually to be removed by alpha-1-antitrypsin (AAT) (molecular weight 54000 Dalton) that may occur in the dialysate and/or the cell or tissue component. This inhibitor/antagonist to elastase (which is beneficial to wound healing) can diffuse freely into the exudate and eventually pass to the wound bed, where it can act beneficially on it.

As an example of option c), a membrane with a suitable MWCO will allow significant amounts of solutes or disperse phase species to pass from the dialysate into the irrigant and/or wound exudate through the polymer film, sheet or membrane. This property may be used to perfuse materials beneficial to wound healing into the irrigant and/or exudate from a dialysate. In this less conventional type of infusion feed, a broad spectrum of species will usually pass into the exudate and/or irrigant fluid from the dialysate.

These include materials that are beneficial to wound healing and are expressed by the cell or tissue component. Such materials include cytokines, enzymes, growth factors, and others having beneficial effects in causing chemotaxis.

These include (a) ionic species, such as bicarbonate; (b) vitamins, such as ascorbic acid (vitamin C) and vitamin E, and stable derivatives thereof, and mixtures thereof; to relieve oxidative stress on the wound bed; (c) pH buffering agents, such as potassium dihydrogen phosphate/disodium hydrogen phosphate, (d) local analgesics/anaesthetics, such as lidocaine/lignocaine hydrochloride and xylocaine (adrenoline lidocaine) and/or anti-inflammatories, to reduce wound pain or inflammation or pain associated with the dressing; (e) nutrients to aid proliferation of wound cells, such as amino acids, sugars, low molecular weight tissue building blocks and trace elements; and other cell culture medium species; and (f) gases, such as air, nitrogen, oxygen and/or nitric oxide.

For the purposes of fluid cleansing in the apparatus, both the single-phase system, such as an ultrafiltration unit, and two-phase system, such as a dialysis unit, may have captive (non-labile, insoluble and/or immobilised) species such as the following.

They are bound to an insoluble and/or immobilised) substrate over and/or through which the irrigant and/or wound exudate from, the wound dressing passes in turn to the fluid recirculation tube(s): (a) antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed; (b) metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine); (c) iron III reductants; (d) protease inhibitors, such as TIMPs and alpha 1-antitrypsin (AAT); serine protease inhibitors, such as 4-(2-aminoethyl)-benzene sulphonyl fluoride (AEBSF, PefaBloc) and Nα-p-tosyl-L-lysine chloro-methyl ketone (TLCK) and ε-aminocaproyl-p-chlorobenzylamide; cysteine protease inhibitors; matrix metalloprotease inhibitors; and carboxyl (acid) protease inhibitors; (e) sacrificial redox materials that are potentially or actually beneficial in promoting wound healing, by the removal of materials that trigger the expression into wound exudate of redox-sensitive genes that are deleterious to wound healing; (f) autoinducer signalling molecule degraders, which may be enzymes; and (g) anti-inflammatory materials to bind or destroy lipopolysaccharides, e.g. peptidomimetics.

Other physiologically active components of the exudate that are deleterious to wound healing may be removed in this way. These may be removed with suitable chelators and/or ion exchangers, degraders, which may be enzymes, or other species.

The following types of functionalised substrate has sites on its surface that are capable of removing materials deleterious to wound healing on passing the circulating fluid from the wound and container for cells or tissue and the fluid reservoir over them: (a) heterogeneous resins, for example silica-supported reagents such as: (i) metal scavengers, (ii) 3-(diethylenetriamino)propyl-functionalised silica gel, (iii) 2-(4-(ethylenediamino)benzene)ethyl-functionalised silica gel, (iv) 3-(mercapto)propyl-functionalised silica gel, (v) 3-(1-thioureido)propyl-functionalised silica gel, (vi) triamine tetraacetate-functionalised silica gel; or (b) electrophilic scavengers, (i) 4-carboxybutyl-functionalised silica gel, (ii) 4-ethyl benzenesulfonyl chloride-functionalised silica gel, (iii) propionyl chloride-functionalised silica gel, (iv) 3-(isocyano)propyl-functionalised silica gel, (v) 3-(thiocyano)propyl-functionalised silica gel, (vi) 3-(2-succinic anhydride)propyl-functionalised silica gel, (vii) 3-(maleimido)propyl-functionalised silica gel, or (c) nucleophilic scavengers, (i) 3-aminopropyl-functionalised silica gel, (ii) 3-(ethylenediamino)-functionalised silica gel, (iii) 2-(4-(ethylenediamino)propyl-functionalised silica gel, (iv) 3-(diethylenetriamino)propyl-functionalised silica gel, (v) 4-ethyl-benzenesulfonamide-functionalised silica gel, (vi) 2-(4-toluenesulfonyl hydrazino)ethyl-functionalised silica gel, (vii) 3-(mercapto)propyl-functionalised silica gel, (viii) dimethylsiloxy-functionalised silica gel, or (d) base or acid scavengers, (i) 3-(dimethylamino)propyl-functionalised silica gel, (ii) 3-(1,3,4,6,7,8-hexahydro-2H-pyrimido-[1,2-a]pyrimidino)propyl-functionalised silica gel, (iii) 3-(1-imidazol-1-yl)propyl-functionalised silica gel, (iv) 3-(1-morpholino)propyl-functionalised silica gel, (v) 3-(1-piperazino)propyl-functionalised silica gel, (vi) 3-(1-piperidino)propyl-functionalised silica gel, (vii) 3-(4,4'-trimethyldipiperidino)propyl-functionalised silica gel, (viii) 2-(2-pyridyl)ethyl-functionalised silica gel, (ix) 3-(trimethylammonium)propyl-functionalised silica gel, or (e) the reagents: (i) 3-(1-cyclohexylcarbodiimido)propyl-functionalised silica gel, (ii) TEMPO-functionalised silica gel, (iii) 2-(diphenylphosphino)ethyl-functionalised silica gel, (iv) 2-(3,4-cyclohexyldiol)propyl-functionalised silica gel, (v) 3-(glycidoxy)propyl-functionalised silica gel, (vi) 2-(3,4-epoxycyclohexyl)propyl-functionalised silica gel, (vii) 1-(allyl)methyl-functionalised silica gel, (viii) 4-bromopropyl-functionalised silica gel, (ix) 4-bromophenyl-functionalised silica gel, (x) 3-chloropropyl-functionalised silica gel, (xi) 4-benzyl chloride-functionalised silica gel, (xii) 2-(carbomethoxy)propyl-functionalised silica gel, (xiii) 3-(4-nitrobenzamido)propyl-functionalised silica gel, (xiv) 3-(ureido)propyl-functionalised silica gel; or any combinations of the above.

The use of such captive (non-labile, insoluble and/or immobilised) species, such as the foregoing, bound to an insoluble and immobilised) substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

The means for fluid cleansing may additionally, where appropriate, comprise one or more macroscopic and/or microscopic filters. These are to retain particulates, e.g. cell debris and micro-organisms, allowing proteins and nutrients to pass through.

Alternatively, a less conventional type of two-phase system (see above), such as a dialysis unit, may be used as the means for fluid cleansing. In this type, the dialysis polymer film, sheet or membrane is not an integer selectively permeable to materials deleterious to wound healing, such as (a) proteases, such as serine proteases, e.g. elastase and thrombin; cysteine protease; matrix metalloproteases, e.g. collagenase; and carboxyl (acid) proteases; (b) endotoxins, such as lipopolysaccharides; and (c)oxidants, such as free radicals, e.g. peroxide and superoxide; and (d) metal ions, e.g. iron II and iron III; all involved in oxidative stress on the wound bed.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being (a) antagonists to such species, for example enzymes or others, such as protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors; (b) binders and/or degraders, such as anti-inflammatory materials to bind or destroy lipopolysaccharides, e.g. peptidomimetics; (c) anti-oxidants, such as 3-hydroxytyramine (dopamine), ascorbic acid (vitamin C), vitamin E and glutathione, and stable derivatives thereof, and mixtures thereof; to relieve oxidative stress on the wound bed; and (d) chelators and/or ion exchanges, such as desferrioxamine (DFO), 3-hydroxytyramine (dopamine).

They further include (a) peptides (including cytokines, e.g. bacterial cytokines, such as α-amino-γ-butyrolactone and L-homocarnosine); and (b) sacrificial redox materials that are potentially or actually beneficial in promoting wound healing, such as iron III reductants; and/or regeneratable materials of this type, such as glutathione redox systems; and (c) other physiologically active components.

In use of the two-phase system dialysis unit, of this less conventional type, a broad spectrum of species will usually pass into the dialysate from the exudate. Some (mainly ionic) species will pass from the dialysate into the irrigant and/or wound exudate through the dialysis polymer film, sheet or membrane that is not very selectively permeable to materials deleterious to wound healing. The components of the exudate from a wound and/or irrigant fluid will diffuse freely to and fro through it.

If (preferably) none of the dialysate is voided to waste, e.g. to a collection bag, a steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing (including such materials that have been added using cells or tissue). It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc. The cleansed fluid, still containing some materials that are beneficial in promoting wound healing, is returned to the recirculation tube.

Unlike the other components of the exudate from a wound and/or irrigant fluid the target materials are constantly removed from the dialysate, very little of these species will pass from the dialysate into the irrigant and/or wound exudate, and a steady state concentration equilibrium is not set up, even if the species are constantly 'topped up' from the wound dressing.

It is believed that circulating wound fluid aids in removal from recirculation of the materials deleterious to wound healing from wound exudate, whilst retaining materials that are beneficial in promoting wound healing (including such materials that have been added using cells or tissue) in contact with the wound.

A particular advantage of this form of the two-phase system, is that where a material that can remove materials deleterious to wound healing from wound exudate is (cyto) toxic or bioincompatible, or not inert to any components that are beneficial in promoting wound healing, the system does not allow any significant amounts of antagonist to diffuse freely out of the dialysate into the irrigant fluid. The active material can act beneficially on the fluid however.

The film sheet or membrane is preferably a dialysis membrane of molecular weight cut off (MWCO) (as conventionally defined) chosen to allow perfusion of species targeted for sequestration or destruction.

For example, sequestration of the serine protease elastase (molecular weight 25900 Dalton) would require a membrane with MWCO>25900 Dalton.

The MWCO threshold can be varied to suit each application between 1 and 3000000 Dalton. Preferably, the MWCO should be as close as possible to this weight to exclude sequestering interference by larger competitor species.

Where it is desired to remove several different materials that are deleterious to wound healing, it may be advantageous to provide a system of modules in series, each of which removes a different material. This allows incompatible cell or tissue materials to be used on the same fluid and/or wound exudates. Both the single-phase system, such as an ultrafiltration unit, and two-phase system, such as a dialysis unit, may be in modular form that is relatively easily demountable from the apparatus. The system may suitably comprise one or more such modules. Preferably any such system is a conventional automated, programmable system which can cleanse the wound irrigant and/or wound exudate with minimal supervision.

It is believed that aspirating wound fluid aids in removal from of the materials deleterious to wound healing from wound exudate and/or irrigant, whilst distributing materials that are beneficial in promoting wound healing in contact with the wound.

A steady state concentration equilibrium of materials beneficial in promoting wound healing may be set up between in the irrigant and/or wound exudate.

Aspirating wound fluid aids in the quicker attainment of this equilibrium

Materials beneficial to wound healing that are distributed include cytokines, enzymes, growth factors, cell matrix components, biological signalling molecules and other physiologically active components of the exudate and/or materials in the irrigant that are potentially or actually beneficial in respect of wound healing, such as nutrients for wound cells to aid proliferation, gases, such as oxygen.

The conduits through which respectively (a) the irrigant and/or wound exudate passes from the wound dressing and (b) the cleansed fluid, still containing materials that are beneficial in promoting wound healing, is returned to the recirculation tube, and (c) (in the case where the means is provided in the form of a two-phase system, such as an dialysis unit) through which the cleansing fluid enters and exits the means (d) preferably have means for, on module disconnection and withdrawal, (i) switching off the flow and (ii) providing an immediate fluid-tight seal or closure over the ends of the conduits and the cooperating tubes in the rest of the apparatus so exposed, to prevent continuing passage of irrigant and/or exudate and cleansed fluid, and cleansing fluid.

The apparatus for aspirating, irrigating and/or cleansing wounds is provided with means for bleeding the offtake and/or recirculation tubes, such as a regulator, such as a valve or other control device for bleeding fluids from the wound.

The device for moving fluid through the wound and means for fluid cleansing is used to move irrigant to the wound dressing and apply the desired positive or negative pressure on the wound bed.

The desired balance of fluid in recirculation tube will typically be regulated by means of (a) the means for bleeding the offtake and/or recirculation tubes, (b) the means for flow switching between supply and recirculation, and/or (c) the means for moving fluid over the wound bed and through the means for fluid cleansing, as appropriate.

Thus, e.g. if (a) the apparatus for aspirating, irrigating and/or cleansing wounds is a single-phase system, such as an ultrafiltration unit, (b) the wound is not in a highly exuding state and (c) it is not appropriate or desired to admit fluid into the wound from the fluid reservoir, there is no or negligible change in the balance of fluid in recirculation. Once it has been primed throughout, e.g. to the desired positive or negative pressure on the wound bed, the apparatus may be operated as a closed recirculating system.

The means for flow switching between supply and recirculation tubes is set to close the wound to the fluid reservoir via the fluid supply tube, and the means for bleeding the offtake and/or recirculation tubes are also closed.

If (a) the apparatus for aspirating, irrigating and/or cleansing wounds is a single-phase system, such as an ultrafiltration unit, (b) the wound is in a highly exuding state and/or (c) it is appropriate or desired to admit fluid into the wound from the fluid reservoir, there is a positive change in the balance of fluid in recirculation.

Once it has been primed throughout, e.g. to the desired positive or negative pressure on the wound bed, the apparatus cannot be operated as a closed recirculating system, without the pressure to the wound bed increasing, possibly undesirably.

The apparatus may have a two-phase system means for fluid cleansing in the form of a dialysis unit, or a biphasic extraction unit, container, e.g. a canister, cartridge or cassette, with one compartment through which the circulating fluid from the wound and the fluid reservoir passes and is separated by an integer that is permeable to materials in the circulating fluid in the apparatus, and a second compartment containing cells or tissue, through which passes a cleansing fluid.

The factors that determine the balance of fluid in recirculation in such an apparatus have been described hereinbefore in detail hereinbefore in connection with the operation of the apparatus. It is sufficient to note here that at some point after steady state recirculation established through the length of the apparatus flow path, it may be necessary that any bleed valve is opened, if overall the fluid level is increasing by transfer from the dialysate to an undesirable extent.

Other combinations, and the necessary adjustments to maintain the desired balance of fluid in recirculation tube by means of (a) the means for bleeding the offtake and/or recirculation tubes, (b) the means for flow switching between supply and recirculation, and/or (c) the means for moving fluid, (d) will be apparent to the skilled person.

The outlet from the means for bleeding the offtake and/or recirculation tubes may be collected and monitored and used to diagnose the status of the wound and/or its exudate. The waste reservoir (and/or aspirate collection vessel) may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the waste reservoir (and/or aspirate collection vessel) will be largely determined by its function. To be suitable for use, the material need only be fluid-impermeable once in use, and flexible. Examples of suitable materials for the fluid reservoir include synthetic polymeric materials, such as polyolefins, such as poly (vinylidene chloride). Suitable materials for the present purpose also include polyethylene, e.g. high-density polyethylene, polypropylene, copolymers thereof, for example with vinyl acetate and mixtures thereof.

Wound Contact Layer

In certain embodiments, the apparatus for aspirating, irrigating, and/or cleansing wounds further comprises a wound contact layer. The wound contact layer may be made from any suitable material known in the art which will allow nutrients to reach the wound bed. Having a wound contact layer may prevent overgrowth of the granulation material.

A significant advantage, in particular in chronic wounds, is that in use granulation tissue is encouraged to grow onto and/or into the wound contact layer that lies between the wound film dressing and the wound bed. The effect may be further enhanced by the circulation over the wound bed of irrigant from the fluid reservoir which contains nutrients for wound cells to aid proliferation, and other molecules that are beneficially involved in wound healing and/or that are favourable to the wound healing process.

A further particular advantage is that it is unnecessary to remove this granulation tissue in-growth on dressing change, as the wound contact layer may be left between the wound film dressing and the wound bed biodegrade. This minimises trauma and any need for debridement.

Another particular advantage of this wound contact layer is its use with pressure sores: the device can be placed in the depths of the wound and the patient can lie upon it without either affecting the utility of the device or further damaging the wound. This becomes critical if the patient cannot be moved from this posture for other medical reasons.

The wound contact layer is placed over substantially the expanse of the wound, and its size and configuration can be adjusted to fit the individual wound. It can be formed from a variety of apertured, semi-rigid materials. By 'apertured' herein is meant materials that are porous, apertured, holed, open-mesh, slit, incised and/or cut. The material must be sufficiently apertured to allow for invasion by all manner of cells involved in the process of tissue repair and wound healing, and/or for the inward growth of blood vessels, and sufficiently rigid to prevent overgrowth and collapse under suction.

Suitable biomaterials for a biodegradable wound contact layer include poly(hydroxy acids) and esters thereof, such as poly(glycolic acid), poly(L-lactic acid), poly(D-lactic acid) and esters thereof, and copolymers and blends of the aforementioned. Suitable biomaterials also include poly(acid anhydrides), such as poly(terephthalic acid), poly(adipic acid) and copolymers and blends of the aforementioned. Additionally, biologically sourced biodegradable polymeric materials may be used, such as substantially protein based polymers, for example collagens, fibronectins, or fibrins, either as whole molecules or those subjected to proteolytic or chemical treatments, in either degraded or native conformations, or modified protein based polymers produced by nucleic acids recombinant techniques, for example, collagens, fibronectins, or fibrins, or fragments thereof, produced through recombinant DNA techniques; or blends thereof. Further acceptable wound contact layers will be combinations of protein based scaffolds and carbohydrate based polymers such as glycosoaminoglycans, chitosans, cellulose or alginate molecules. Suitable materials also include human or animal derived tissues processed in means to make them acceptable in placement into the wound such as skin, alimentary tract or connective tissues.

The wound contact layer/material may be formed in a variety of apertured, semi-rigid forms. These forms may be essentially two-dimensional, such as sheets, layers, films, flexible panels, meshes, nets, webs or lattices. They may be placed in the wound as dry, hydrated or gel based formulations. One embodiment of apertured or holed scaffold comprises a section of honeycombed polymer sheet cut to the shape of the wound.

Where the wound contact layer is in an essentially two-dimensional apertured, semi-rigid form, such as a sheet, layer, film, flexible panel, mesh, net, web or lattice, it may be designed in a configuration that is able to conform well to the wound bed on insertion into the wound. This conforming to shape is then a particular advantage in those embodiments where the wound dressing is used on deeper wounds, especially where a wound filler is used to urge the wound dressing towards the wound contact layer and wound bed, as described hereinafter in connection with the wound dressing.

By way of example, such a wound contact layer may be in the form of a deeply indented circular disc much like a multiple Maltese cross or a stylised rose. This form is able to conform well to the wound bed on insertion into the wound, especially a deeper wound, by the arms closing in and possibly overlapping. The form of the wound contact layer may also be three-dimensional, such as sheets, layers, films, flexible panels, meshes, nets, webs and lattices, folded, creased, pleated, tucked, crinkled, crumpled, screwed up or twisted into a three-dimensional form. Alternatively, these forms may be inherently three-dimensional, such as multilayers of films, flexible panels, meshes, nets, webs and lattices, or three-dimensional meshes, nets, webs and lattices, and favourably foams. They may be placed in the wound as dry, hydrated or gel based formulations.

Operation of a Typical Apparatus

The operation of a typical apparatus of this type for simultaneous aspiration and irrigation of a wound at a low negative pressure of up to 20% atm., more usually up to 10% atm. at the wound, with one pump will now be described.

In one embodiment, there is provided an apparatus with (a) a single device for moving fluid through the wound applied to the aspirate in the fluid offtake tube downstream of and away from the wound dressing, in combination with (b) means for supply flow regulation, connected to a fluid supply tube, and (c) means for aspirate flow regulation, connected to a fluid offtake tube. Before starting the apparatus of this embodiment for aspirating, irrigating and/or cleansing wounds, the backing layer of the wound dressing is applied over the wound and conformed to the shape of the bodily part in which the wound is to form a relatively fluid-tight seal or closure. The means for supply flow regulation, connected to a fluid supply tube, such as a regulator, such as a rotary valve, is usually closed, and the means for aspirate flow regulation (if any), connected to a fluid offtake tube, is opened. The aspiration pump is started and run to give a negative pressure of up to 50% atm., more usually up to 20% atm., e.g. up to 10% atm. to be applied applies a vacuum to the interior of the dressing and the wound. The means for fluid supply regulation is opened and is then adjusted, and/or where the aspiration pump is a variable-speed pump, downstream of the wound dressing, that is adjusted, to maintain the desired balance of fluid at a controlled nominal flow rate and to maintain the desired negative pressure in the interior of the wound dressing. The apparatus is then run for the desired length of therapy and with the desired negative pressure regime. After this period, the aspiration pump is stopped.

The operation of a typical apparatus for simultaneous aspiration and irrigation of a wound at a low negative pressure of up to 20% atm., more usually up to 10% atm. at the wound, with two pumps will now be described.

The necessary changes where the mode of operation is at a net positive pressure of e.g. up to 15% atm., more usually up to 10% atm. at the wound will be apparent to the skilled person. Such a typical apparatus for simultaneous aspiration and irrigation of a wound at a low negative pressure of up to 20% atm., more usually up to 10% atm. at the wound comprises means for providing simultaneous aspiration and irrigation of the wound which is a combination of (a) a first device for moving fluid through the wound applied to the aspirate in the fluid offtake tube downstream of and away from the wound dressing, with optional means for aspirate flow regulation, connected to a fluid offtake tube: and (b) a second device for moving fluid through the wound applied to the irrigant in the fluid supply tube upstream of and towards the wound dressing, with optional means for supply flow regulation, connected to a fluid supply tube. As noted above, either device may be (a) a fixed-throughput device, such as a fixed-speed pump, which will usually require a discrete means for aspirate flow regulation, connected to a fluid offtake tube, e.g. a regulator, such as a rotary valve, or for irrigant flow regulation, connected to a fluid supply tube, either e.g. a regulator, such as a rotary valve, or (b) a variable-throughput device, such as a variable-speed pump, thus effectively forming a combination of a device for moving fluid through the wound with means for flow regulation in a single integer. Before starting the apparatus of this embodiment for aspirating, irrigating and/or cleansing wounds, the backing layer of the wound dressing is applied over the wound and conformed to the shape of the bodily part in which the wound is to form a relatively fluid-tight seal or closure. Any means for supply flow regulation, connected to a fluid supply tube, such as a regulator, such as a rotary valve, is usually closed, and any means for aspirate flow regulation, connected to a fluid offtake tube, is opened.

The aspiration pump is started and run to apply a negative pressure of up to 50% atm., more usually up to 20% atm., e.g. up to 10% atm., to the interior of the dressing and the wound. The irrigation pump is then started, so that both pumps are running together, and any means for supply flow regulation is opened. The irrigation pump flow rate and any means for fluid supply regulation are then adjusted and/or where the aspiration pump and/or the irrigation pump is a variable-speed pump, either or both is/are is adjusted, to maintain the desired balance of fluid at a controlled nominal flow rate and to maintain the desired negative pressure in the interior of the wound dressing. The apparatus is then run for the desired length of therapy and with the desired pressure regime. After this period, the irrigation pump is stopped, shortly followed by the aspiration pump.

BRIEF DESCRIPTION OF THE DRAWINGS

The present invention will now be described by way of example only with reference to the accompanying drawings in which:

FIG. 1b also has a single-phase system means for fluid cleansing in the form of an ultrafiltration unit. The apparatus may have a single-phase system means for fluid cleansing in the form of a container, e.g. a canister, cartridge or cassette, with a chamber or compartment that contains a cell or tissue component, through which the wound exudate or a mixture with irrigant passes in recirculation.

FIGS. 4a to 8b are cross-sectional views of conformable wound dressings. In these, FIG. 4a is a cross-sectional plan view of the wound dressing, while FIG. 5a is a cross-sectional plan view of the wound dressing, while FIG. 6a is a cross-sectional plan view of the wound dressing, while FIG. 7a is a cross-sectional plan view of the wound dressing, while FIG. 8a is a cross-sectional plan view of the wound dressing, while FIG. 8b is a cross-sectional side view of the wound dressing.

FIGS. 9a to 11c are various views of inlet and outlet manifold layouts for the wound dressings for respectively delivering fluid to, and collecting fluid from, the wound. FIGS. 9a-d are various views of inlet and outlet manifold layouts for the wound dressings for respectively delivering fluid to, and collecting fluid from, the wound. FIGS. 1a-c are various views of inlet and outlet manifold layouts for the wound dressings for respectively delivering fluid to, and collecting fluid from, the wound.

FIGS. 16a to 29 are cross-sectional views of conformable wound dressings. In these, FIGS. 16a-b are cross-sectional views of conformable wound dressings.

FIG. 17 is a cross-sectional view of a conformable wound dressing.

FIG. 18 is a cross-sectional view of a conformable wound dressing.

FIG. 20 is a cross-sectional view of a conformable wound dressing.

FIG. 22 is a cross-sectional view of a conformable wound dressing.

FIG. 23 is a cross-sectional view of a conformable wound dressing.

FIG. 24 is a cross-sectional view of a conformable wound dressing.

FIG. 25 is a cross-sectional view of a conformable wound dressing.

FIG. 26 is a cross-sectional view of a conformable wound dressing.

FIG. 27 is a cross-sectional view of a conformable wound dressing.

FIG. 28 is a cross-sectional view of a conformable wound dressing.

FIG. 29 is a cross-sectional view of a conformable wound dressing.

DETAILED DESCRIPTION OF THE EMBODIMENTS

In all of the pertinent Figures, the components (12A), the fluid reservoir, and (12B), a container that contains a cell or tissue component, may, in alternative embodiments, be replaced by a single fluid reservoir (12), and vice versa.

Figure 1A:
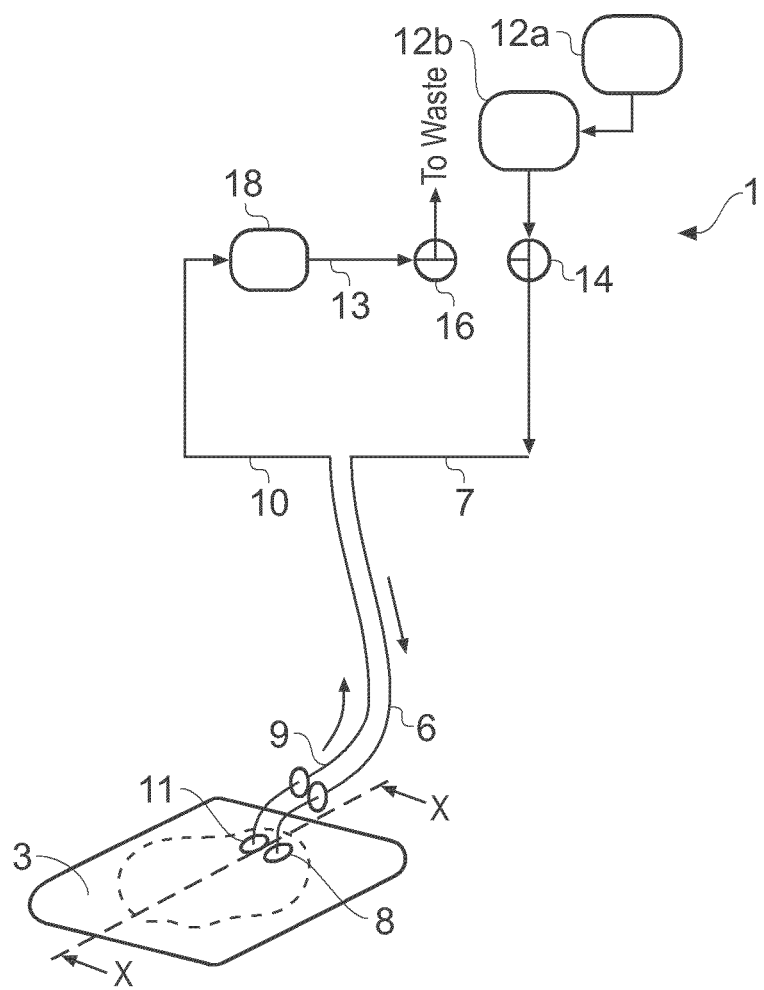
FIGS. 1a and 1b are schematic views of apparatuses for aspirating, irrigating, and/or cleansing a wound. The apparatuses have a single device for moving fluid through the wound applied to the aspirate in the fluid offtake tube downstream of and away from the wound dressing, in combination with means for supply flow regulation, connected to a fluid supply tube, and means for aspirate flow regulation, connected to a fluid offtake tube.
Figure 1A:
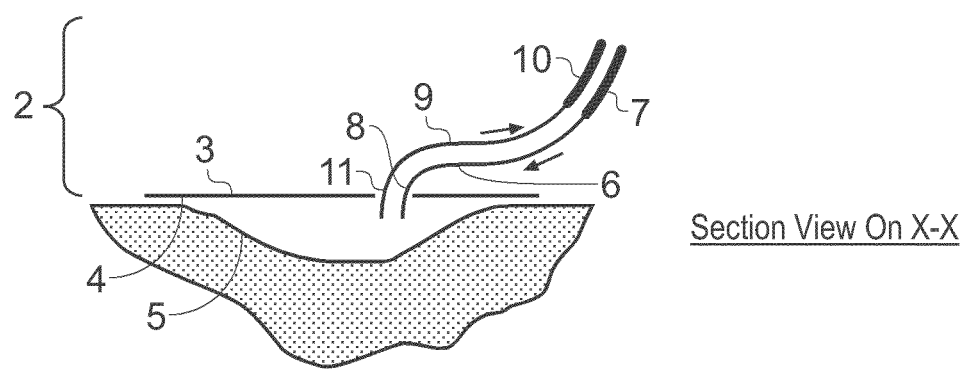

Referring to FIG. 1a, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (3) at (8), and one outlet pipe (9) for connection to a fluid offtake tube (10), which passes through the backing layer (3) at (11), the points (8), (11) at which the inlet pipe and the outlet pipe passes through and/or under the backing layer (3) forming a relatively fluid-tight seal or closure over the wound; the inlet pipe being connected via means for supply flow regulation, here a valve (14), by the fluid supply tube (7) to means for supplying physiologically active agents from cells or tissue to the wound, here a fluid reservoir (12A) and a container that contains a cell or tissue component (12B) connected to the supply tube (7), and the outlet pipe (9) being connected via means for aspirate flow regulation, here a valve (16) and a fluid offtake tube (10) to waste, e.g. to a collection bag (not shown); a device for moving fluid through the wound (5), here a diaphragm pump (18), e.g. preferably a small portable diaphragm pump, acting on the fluid offtake tube (10) to apply a low negative pressure on the wound; and the valve (14) in the fluid supply tube (7), the valve (16) in the fluid aspiration tube (13), and the diaphragm pump (18), providing means for providing simultaneous aspiration and irrigation of the wound (5), such that fluid may be supplied to fill the flowpath from the fluid reservoir via the container that contains the cell or tissue component, in turn connected to a supply tube, fluid supply tube (via the means for supply flow regulation) and moved by the device through the flow path.

The operation of the apparatus is as described hereinbefore. In use, the inlet pipe, means for supply flow regulation, here valve (14), the fluid supply tube (7) and the container for cells or tissue (12B) contain physiologically active components from the cells or tissue in therapeutically active amounts to promote wound healing, and adds such materials into the flowpath.

The supply of such physiologically active materials is here effected to the wound via the fluid passing through the wound dressing from irrigant in the container that contains the cells or tissue.

Figure 1B:
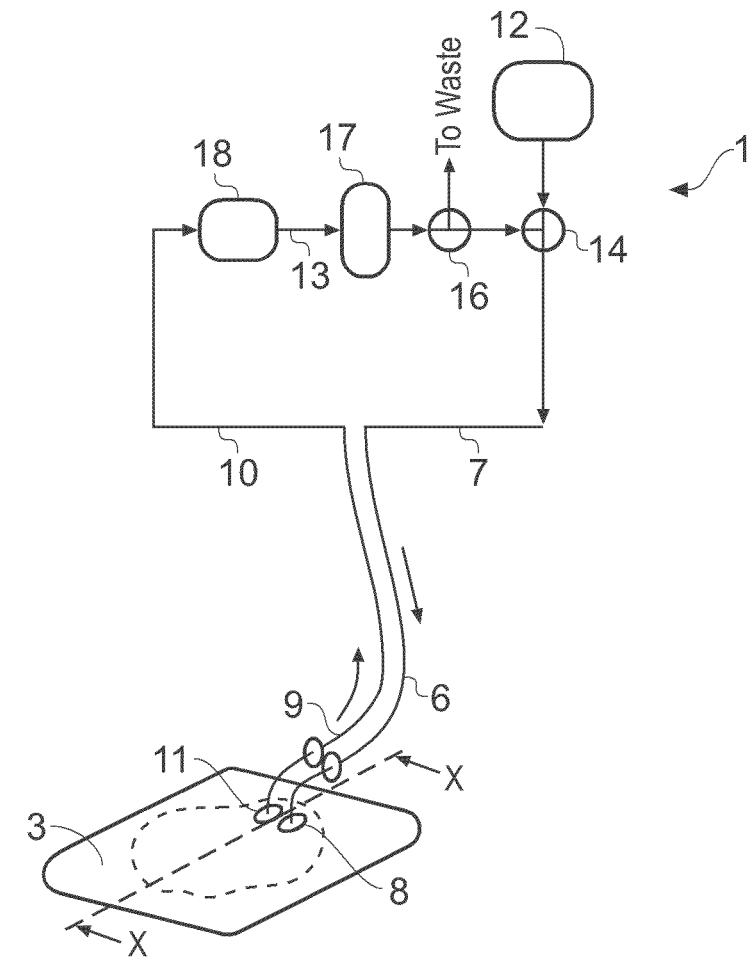
Figure 1B:
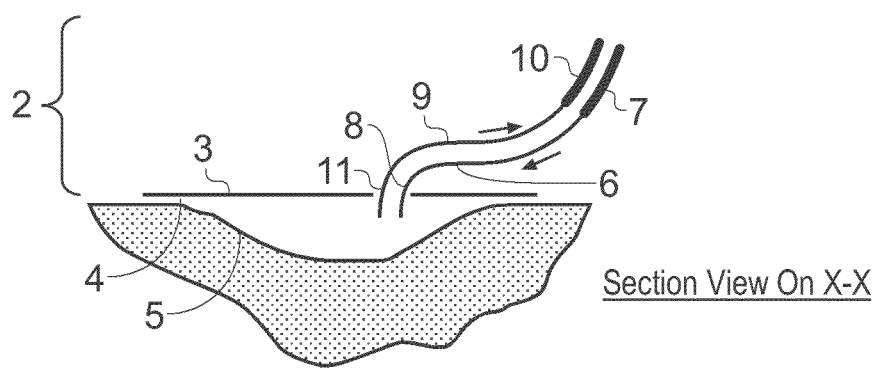

Referring to FIG. 1b, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (3) at (8), and one outlet pipe (9) for connection to a fluid offtake tube (10), which passes through backing layer (3) at (11), the points (8), (11) at which the inlet pipe and the outlet pipe passes through and/or under the backing layer (3) forming a relatively fluid-tight seal or closure over the wound, the inlet pipe being connected via means for supply flow regulation, here a valve (14), by the fluid supply tube (7) to a container for cells or tissue in series with a fluid reservoir (the container and reservoir being shown as a single integer (12)), containing physiologically active components in therapeutically active amounts to promote wound healing, e.g. agents from cells or tissue to the wound, and to a fluid recirculation tube (13) having a means for bleeding the tube, here a valve (16) to waste, e.g. to a collection bag (not shown), the outlet pipe (9) being connected via means for aspirate flow regulation, here a valve (16) and to a fluid offtake tube (10), connected in turn to means for fluid cleansing, in (17), here in the form of either a container, e.g. a canister, cartridge or cassette, with a chamber or compartment that contains a cell or tissue component, through which the wound exudate or a mixture with irrigant passes, or else alternatively an ultrafiltration unit, connected to the inlet pipe (6) via the fluid recirculation tube (13) and T-valve (14), and a device for moving fluid through the wound (5) and means for fluid cleansing (17), here a peristaltic or diaphragm pump (18), e.g. preferably a small portable peristaltic or diaphragm pump, acting on the fluid circulation or aspiration tube (13) with the peripheral rollers on its rotor (not shown) to apply a low negative pressure on the wound; and the valve (14) in the fluid supply tube (7), the valve (16) in the fluid aspiration tube (13), and the diaphragm pump (18), providing means for simultaneous aspiration and irrigation of the wound (5), such that fluid may be supplied to fill the flowpath from the fluid reservoir via the container that contains the cell or tissue component, in turn connected to a supply tube, fluid supply tube (via the means for supply flow regulations) and moved by the device through the flow path.

In one embodiment, in use, the inlet pipe, means for flow switching between supply and recirculation T-valve (14), the fluid supply tube (7), the valve (16) in the fluid offtake tube (10), and the diaphragm pump (18), providing means for providing simultaneous aspiration and irrigation of the wound (5) and the container for cells or tissue (part of the integer (12)) contain physiologically active components from the cells or tissue in therapeutically active amounts to promote wound healing, such that fluid may be supplied to fill the flowpath from the fluid reservoir via the fluid supply tube (via the means for supply flow regulation) and moved by the device through the flow path and adds such materials into the flowpath.

The operation of the apparatus is as described hereinbefore.

The supply of such physiologically active materials may be effected at any appropriate point for this purpose along the apparatus flow path, but it is (as here) often convenient to effect such supply to the wound via the fluid in recirculation through the wound dressing from irrigant in the container that contains the cells or tissue.

The ultrafiltration unit (17) is a single-phase system. In this the circulating fluid from the wound and the container for cells or tissue, and the fluid reservoir passes through a self-contained system in which materials deleterious to wound healing are removed and the cleansed fluid, still containing materials that are beneficial in promoting wound healing, with added elements beneficial to wound healing to the exudate and irrigant (or modified irrigant), modified through biochemical, enzymatic or physical means to contain elements beneficial to wound healing, is returned via the recirculation tube to the wound bed.

(In a variant of this apparatus, there are two inlet pipes (6), which are connected respectively to a fluid supply tube (7) and fluid recirculation tube (13), respectively having a first valve for admitting fluid into the wound from the container from cells or tissue and the fluid reservoir (together the integer 12) and a second valve for admitting fluid into the wound from the recirculation tube. Usually in use of the apparatus, when the first valve is open, the second valve is shut, and vice versa.)

In use of the apparatus (1), the valve (16) is opened to a collection bag (not shown), and the T-valve (14) is turned to admit fluid from the container for cells or tissue and fluid reservoir (together the integer (12)) to the wound dressing through the fluid supply tube (7) and inlet pipe (6).

(In the variant of this apparatus having two inlet pipes (6), which are connected respectively to a fluid supply tube (7) and fluid recirculation tube (13), the first valve for admitting fluid into the wound from the container for cells or tissue and fluid reservoir (together the integer (12)) is opened and the second valve is shut, and vice versa.)

The pump (18) is started to nip the fluid recirculation tube (13) with the peripheral rollers on its rotor (not shown) to apply a low positive pressure on the wound. It is allowed to run until the apparatus is primed throughout the whole length of the apparatus flow path and excess fluid is voided to waste via the bleed T-valve (16) into the collection bag (not shown).

The T-valve (14) is then turned to switch from supply and recirculation, i.e. is set to close the wound to the container from cells or tissue and the fluid reservoir (together the integer (12)) but to admit fluid into the wound from the fluid recirculation tube (13), and the bleed T-valve (16) is simultaneously closed.

(In the variant of this apparatus, there are two inlet pipes (6), which are connected respectively to a fluid supply tube (7) and fluid recirculation tube (13).

In operation, the first valve is closed and a recirculating system set up by opening the second valve for admitting fluid into the wound from the recirculation tube (13).

The circulating fluid from the wound and the container for cells or tissue and the fluid reservoir (together the integer (12)) passes through the ultrafiltration unit (17).

Materials deleterious to wound healing are removed and the cleansed fluid, still containing materials that are beneficial in promoting wound healing with added elements beneficial to wound healing to the exudate and irrigant (or modified irrigant), and/or modified through biochemical, enzymatic or physical means to contain elements beneficial to wound healing, is returned via the recirculation tube (13) to the wound bed. The recirculation of fluid may be continued as long as desired.

Switching between supply and recirculation is then reversed, by turning the T-valve (14) to admit fluid from the fluid reservoir and the container for cells or tissue to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the container for cells or tissue and fluid reservoir (together the integer (12)) is opened and the second valve (20) is shut, and vice versa.)

The bleed valve (16) is simultaneously opened, so that fresh fluid flushes the recirculating system.

The running of the pump (18) may be continued until the apparatus is flushed, when it and the fluid recirculation is stopped.

If, e.g. the wound is in a highly exuding state, there is a positive change in the balance of fluid in recirculation. It may be necessary to bleed fluid from recirculation, by opening the bleed T-valve (16) to bleed fluid from the recirculation tube (13).

Figure 2:
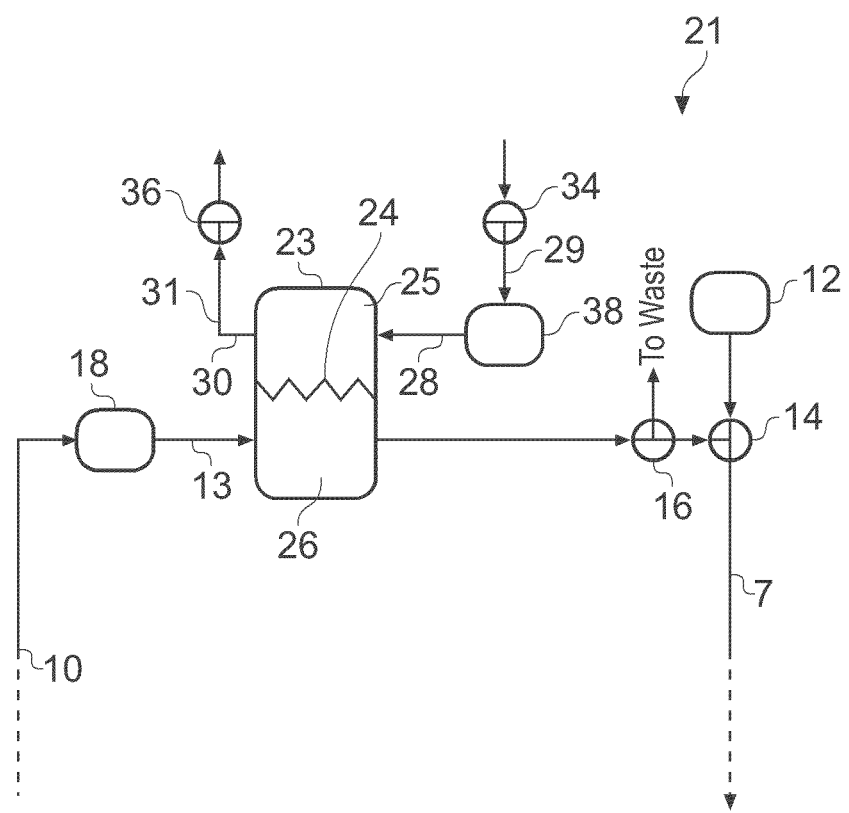
FIG. 2 is a schematic view of an apparatus for aspirating, irrigating and/or cleansing a wound according to an embodiment of the present invention. It has a two-phase system means for fluid cleansing in the form of a dialysis container, e.g. a canister, cartridge or cassette, with one compartment through which the circulating fluid from the wound and the fluid reservoir passes and is separated by an integer that is permeable to materials in the circulating fluid in the apparatus from a second compartment containing cells or tissue, through which passes a cleansing fluid.

Referring to FIG. 2, the apparatus (21) is a variant of that of FIG. 1*b*, with essentially identical, and identically numbered, components, except for the means for fluid cleansing which is in the form of a two-phase system, here a dialysis unit (23). Here a fluid reservoir and a container that contains a cell or tissue component (together the integer 12) connected to the supply tube (7)

In this, there is one system through which the circulating fluid from the wound and the container for cells or tissue and the fluid reservoir passes and from which deleterious materials are removed by selectively permeable contact with a second system, through which passes a cleansing fluid.

The dialysis unit (23) thus has an internal polymer film, sheet or membrane (24), selectively permeable to materials deleterious to wound healing, which divides it into (a) first chamber (25), through which passes a cleansing fluid across one surface of the polymer film, sheet or membrane, and (b) a second chamber (26), through which passes the circulating fluid from the wound and the fluid reservoir (12), and from which deleterious materials are removed The dialysis unit (23) thus has a dialysate inlet pipe (28) connecting to a dialysate supply tube (29) which passes to a peristaltic pump (38), e.g. preferably a small portable peristaltic pump, acting on the dialysate supply tube (29) with the peripheral rollers on its rotor (not shown) to supply cleansing fluid across the surface of the polymer film, sheet or membrane (28) in the first chamber (25) from a dialysate reservoir (not shown) via a valve (34).

The dialysis unit (23) also has a dialysate outlet pipe (30) connecting to a dialysate outlet tube (31) which passes to waste via a second bleed T-valve (36) into, e.g. a collection bag (not shown).

Operation of this apparatus is similar to that of FIGS. 1*a* and 1*b*, except for the dialysis unit (27), in that at some point after the irrigation system is primed and steady state recirculation established through the length of the apparatus flow path, the valve (34) and second bleed valve (36) are opened.

The pump (38) is started to nip fluid dialysate tube (29) with the peripheral rollers on its rotor (not shown) to pump cleansing fluid to the first chamber from a dialysate reservoir (not shown) and out to waste via the bleed valve (36) into the collection bag (not shown).

The dialysis unit (23) is a module (or scrubbing cartridge) with a substrate that changes colour to indicate the presence of detrimental factors in the cleansed fluid, and that the scrubbing cartridge is exhausted and should be renewed.

Figure 3:
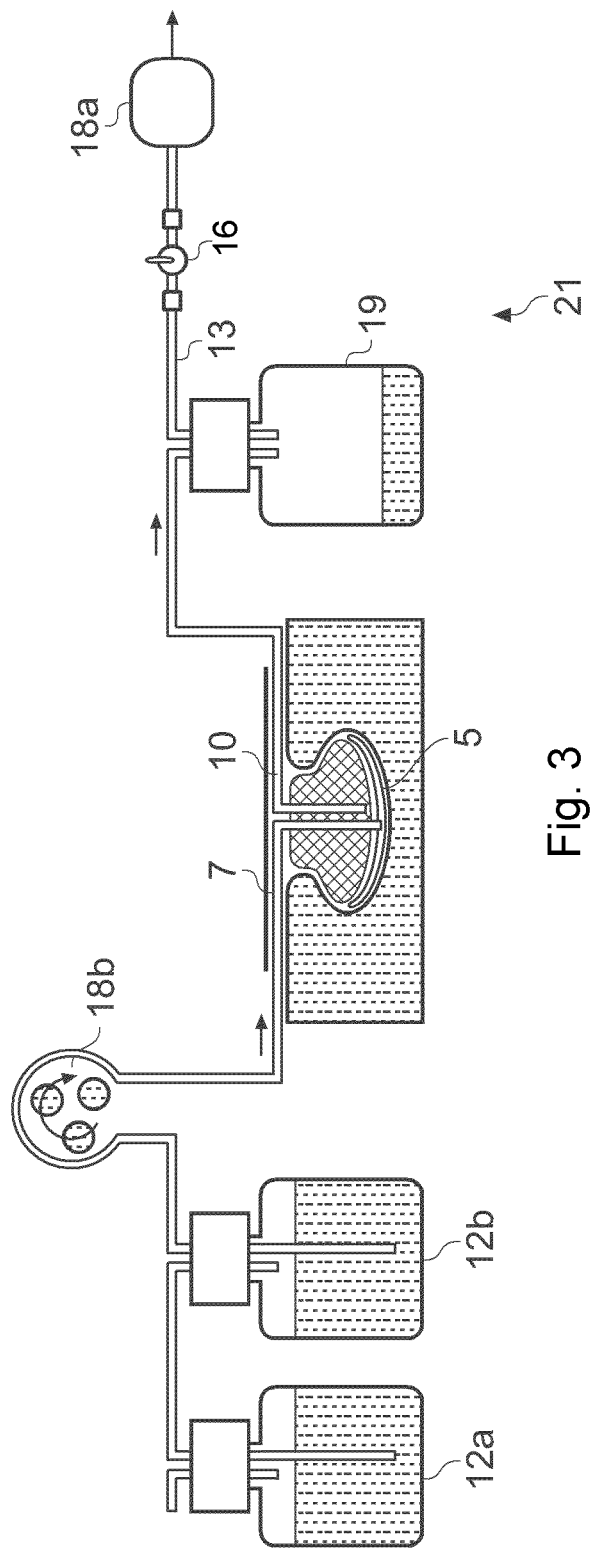
FIG. 3 is a schematic view of another apparatus for aspirating, irrigating and/or cleansing a wound according to an embodiment of the present invention that has a first device for moving fluid through the wound applied to the aspirate in the fluid offtake tube downstream of and away from the wound dressing, with means for aspirate flow regulation, connected to a fluid offtake tube; and a second device for moving fluid through the wound applied to the irrigant in the fluid supply tube upstream of and towards the wound dressing.

Referring to FIG. 3, the apparatus (21) is a variant two-pump system with essentially identical, and identically numbered, components as in FIGS. 1*a* and 1*b*, except that there is no means for supply flow regulation in the fluid supply tube (7) from the means for supplying physiologically active agents from cells or tissue to the wound, and there is a first device for moving fluid through the wound (5), here a diaphragm pump (18*a*), e.g. preferably a small portable diaphragm pump, acting on the fluid aspiration tube (13) downstream of and away from the wound dressing to apply a low negative pressure on the wound; with means for aspirate flow and/or negative pressure regulation, here a valve (16), connected to the fluid aspiration or vacuum tube (13) and a vacuum vessel (aspirate collection jar) (19); and a second device for moving fluid through the wound (5), here a peristaltic pump (18*b*), e.g. preferably a small portable diaphragm pump, applied to the irrigant in the fluid supply tube (7) upstream of and towards the wound dressing, the first device (18*a*) and second device (18*b*), and the valve (16) in the vacuum tube (13), and the diaphragm pump (18*b*), providing means for providing simultaneous (or sequential) aspiration and irrigation of the wound (5), such that fluid may be supplied to fill the flowpath from the fluid reservoir via the fluid supply tube (via the means for supply flow regulation) and moved by the devices through the flow path.

The operation of the apparatus is as described hereinbefore.

Referring to FIGS. 4*a* to 7, each dressing is in the form of a conformable body defined by a microbe-impermeable film backing layer (42) with a uniform thickness of 25 micron, with a wound-facing face which is capable of forming a relatively fluid-tight seal or closure over a wound.

The backing layer (42) extends in use on a wound over the skin around the wound. On the proximal face of the backing layer (42) on the overlap, it bears an adhesive film (not shown), to attach it to the skin sufficiently to hold the wound dressing in place in a fluid-tight seal around the periphery of the wound-facing face of the wound dressing.

Figure 4A:
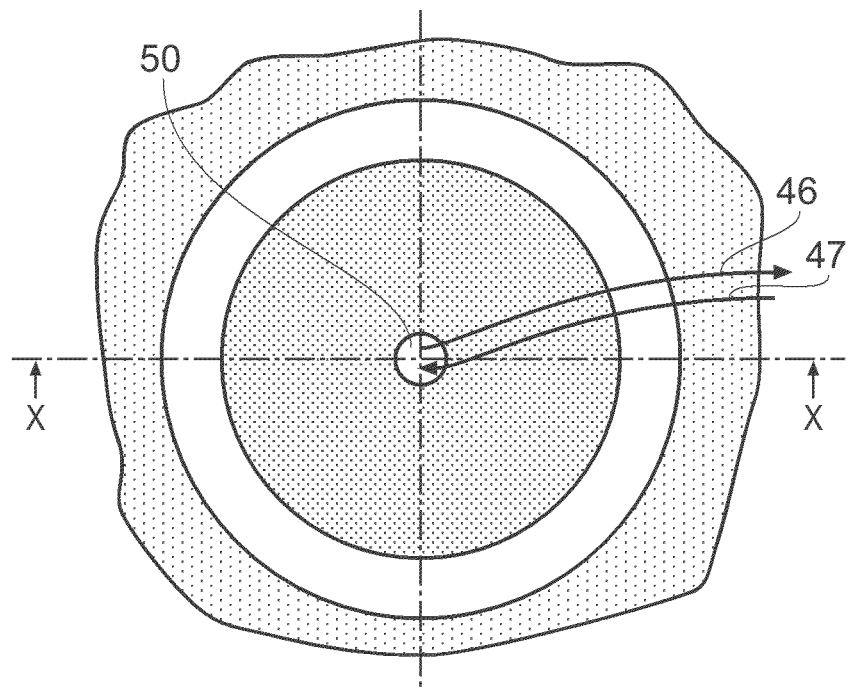
Figure 4B:
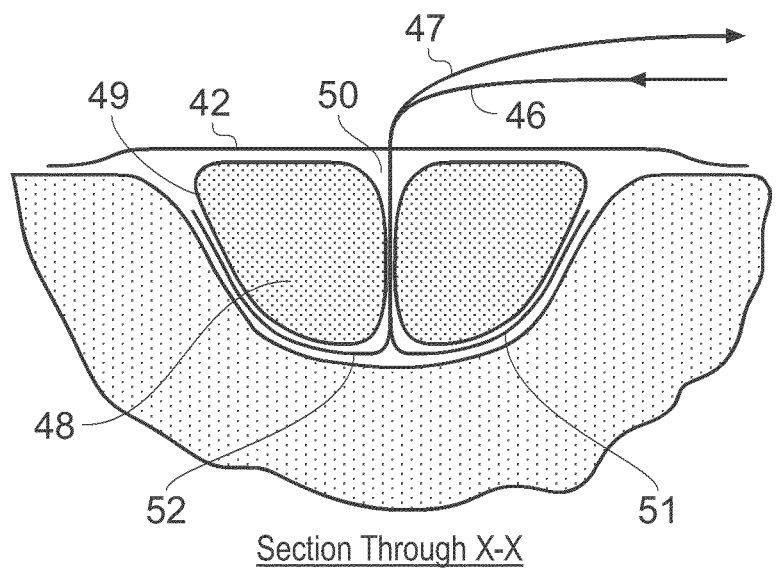
FIG. 4b is a cross-sectional side view of the wound dressing.

There is one inlet pipe (46) for connection to a fluid supply tube (not shown), which passes through and/or under the backing layer (42), and one outlet pipe (47) for connection to a fluid offtake tube (not shown), which passes through and/or under the backing layer (42), Referring to FIGS. 4a and 4b, one form of the dressing is provided with a wound filler (48) under a circular backing layer (42). This comprises a generally frustroconical, toroidal conformable hollow body, defined by a membrane (49) which is filled with a fluid, here air or nitrogen, that urges it to the wound shape. The filler (48) may be permanently attached to the backing layer with an adhesive film (not shown) or by heat-sealing.

The inlet pipe (46) and outlet pipe (47) are mounted centrally in the backing layer (42) above the central tunnel (50) of the toroidal hollow body (48) and each passes through the backing layer (42), and each extends in pipes (51) and (52) respectively through the tunnel (50) of the toroidal hollow body (48) and then radially in diametrically opposite directions under the body (48). In other embodiments the inlet (46) and outlet (47) pipes may pass under the backing layer (42).

This form of the dressing is a more suitable layout for deeper wounds.

Figure 5A:
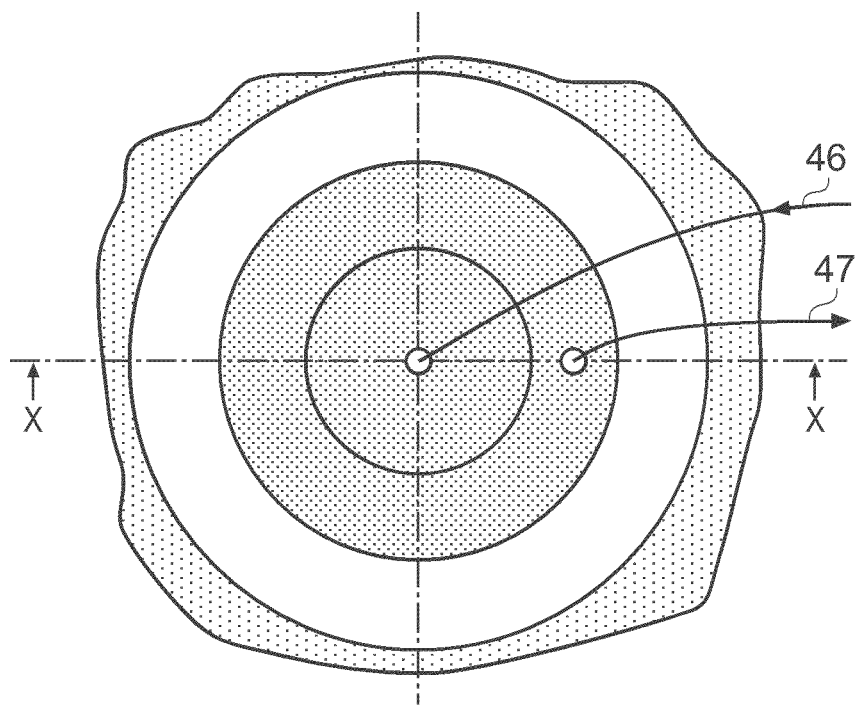
Figure 5B:
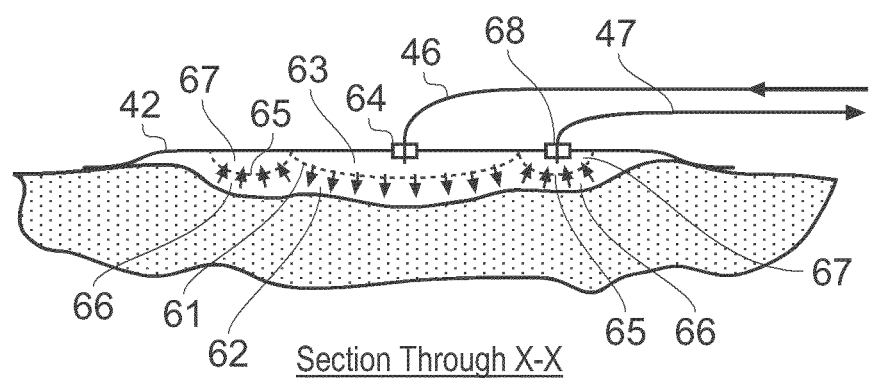
FIG. 5b is a cross-sectional side view of the wound dressing.

Referring to FIGS. 5a and 5b, a more suitable form for shallower wounds is shown. This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the aspirating or circulating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Figure 6A:
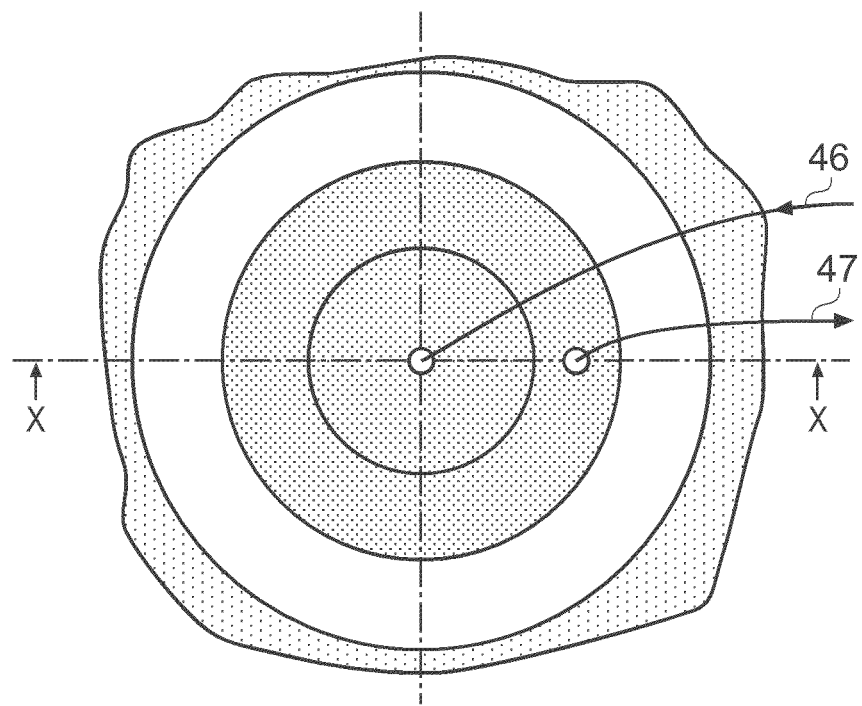
Figure 6B:
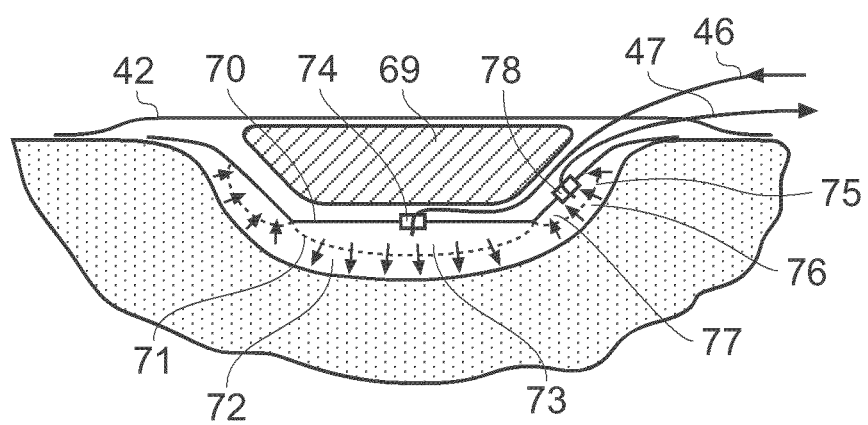
FIG. 6b is a cross-sectional side view of the wound dressing.

Referring to FIGS. 6a and 6b, a variant of the dressing of FIGS. 4a and 4b that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It is permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the aspirating circulating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (47) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape (not shown), instead of the backing layer (42).

Figure 7A:
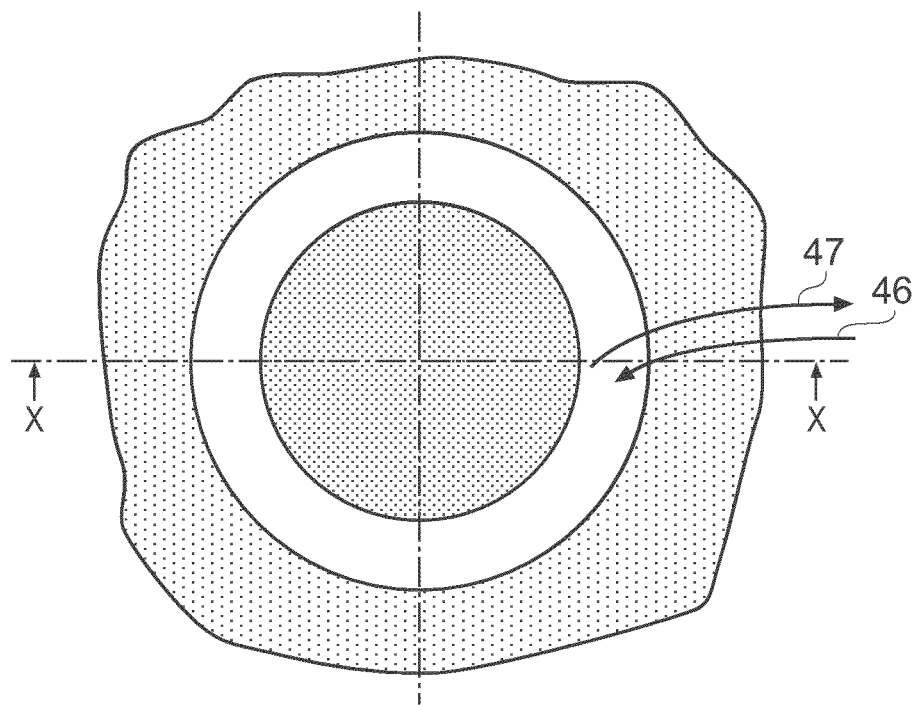
Figure 7B:
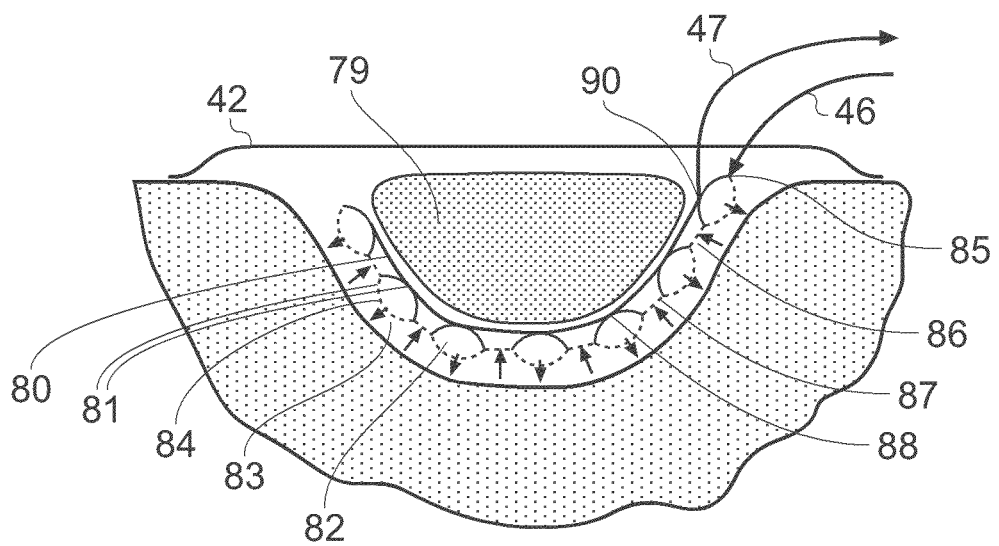
FIG. 7b is a cross-sectional side view of the wound dressing.

Referring to FIGS. 7a and 7b, a dressing that is a more suitable form for deeper wounds is shown.

This comprises a circular backing layer (42) and a filler (79), in the form of an inverted generally hemispherical integer, here a resilient elastomeric foam or a hollow body filled with a fluid, here a gel that urges it to the wound shape, and permanently attached to the backing layer with an adhesive film (not shown) or by heat-sealing.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with perforations (83) along its length on the outer surface (84) of the dish formed by the membrane (81) and an opening (85) at the outer end of its spiral helix, through which the channel (82) communicates with the inlet pipe (46), and thus effectively forms an inlet pipe manifold that delivers the aspirating or circulating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Figure 8A:
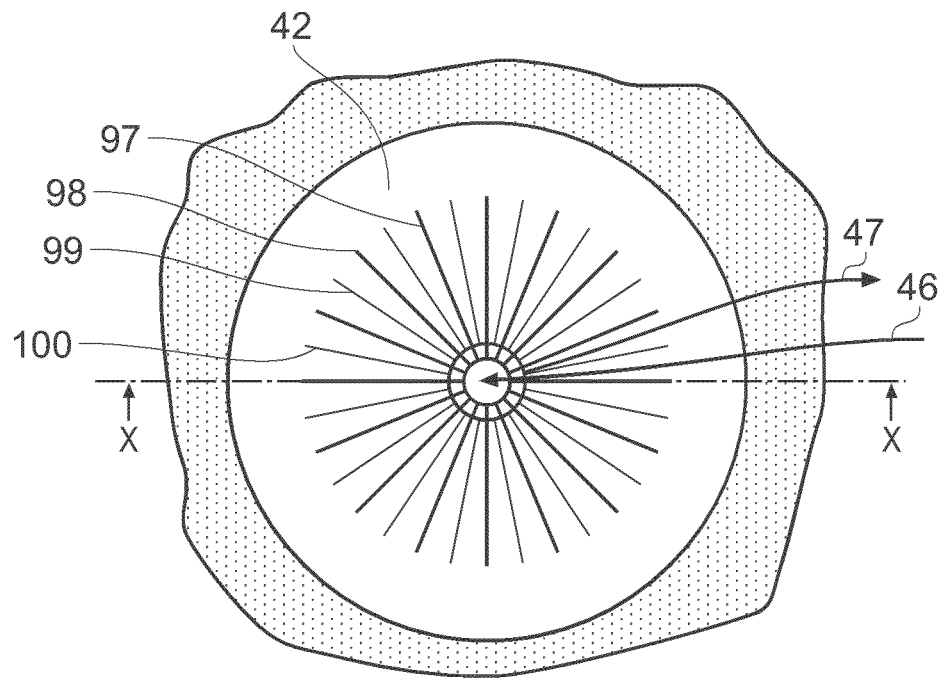
Figure 8B:
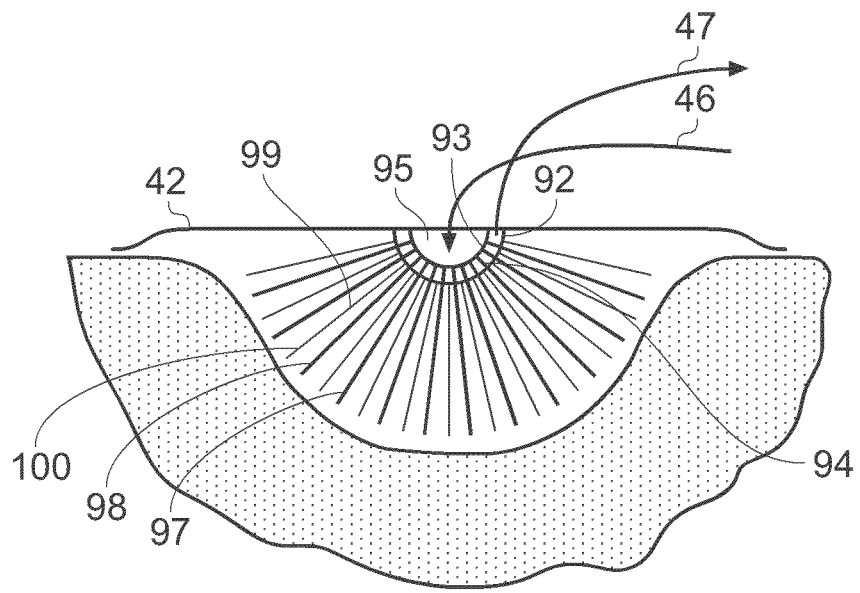

Referring to FIGS. 8a and 8b, one form of the dressing is provided with a circular backing layer (42). A first (larger) inverted hemispherical membrane (92) is permanently attached centrally to the layer (42) by heat-sealing to form a hemispherical chamber (94) with the layer (42). A second (smaller) concentric hemispherical membrane (93) within the first is permanently attached to the layer (42) by heat-sealing to form a hemispherical pouch (95).

The pouch (95) communicates with the inlet pipe (46) and is thus effectively an inlet manifold, from which pipes (97) radiate hemispherically and run to the wound bed to end in apertures (98).

The pipes (97) deliver the aspirating or circulating fluid directly to the wound bed via the apertures (98).

The chamber (94) communicates with the outlet pipe (47) and is thus effectively an outlet manifold from which tubules (99) radiate hemispherically and run to the wound bed to end in openings (100). The tubules (99) collect the fluid directly from the wound via the openings (100).

Referring to FIGS. 9a to 9d, one form of the dressing is provided with a square backing layer (42), and first tube (101) extending from the inlet pipe (46), and second tube (102) extending from the outlet pipe (47), at the points at which they pass through the backing layer, to run over the wound bed.

These pipes (101) and (102) have a blind bore with orifices (103) and (104) along the pipes (101) and (102). These pipes (101) and (102) respectively form an inlet pipe or outlet pipe manifold that delivers the aspirating or circulating fluid directly to the wound bed or collects the fluid directly from the wound respectively via the orifices.

Figure 9A:
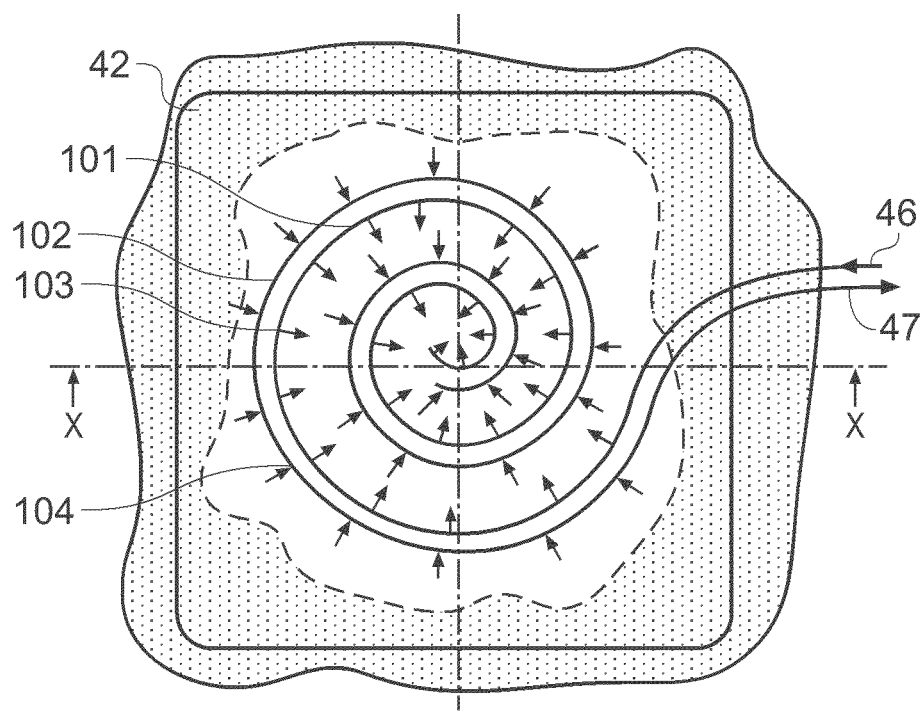
Figure 9B:
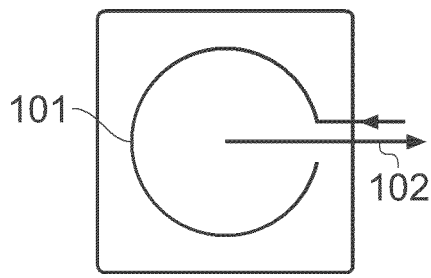
Figure 9C:
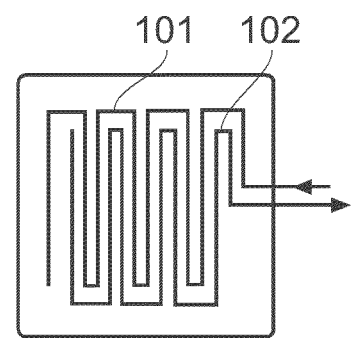
Figure 9D:
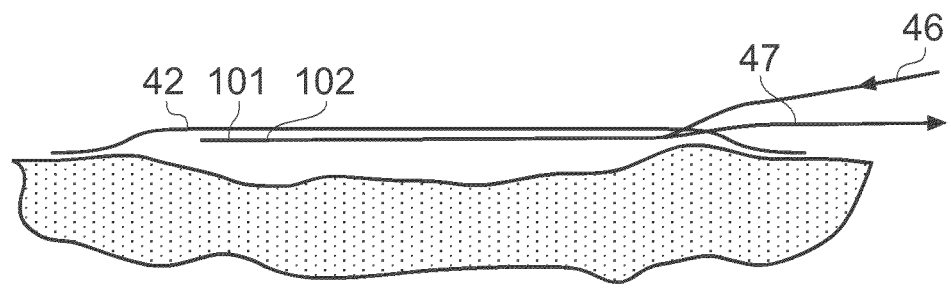
Figure 10A:
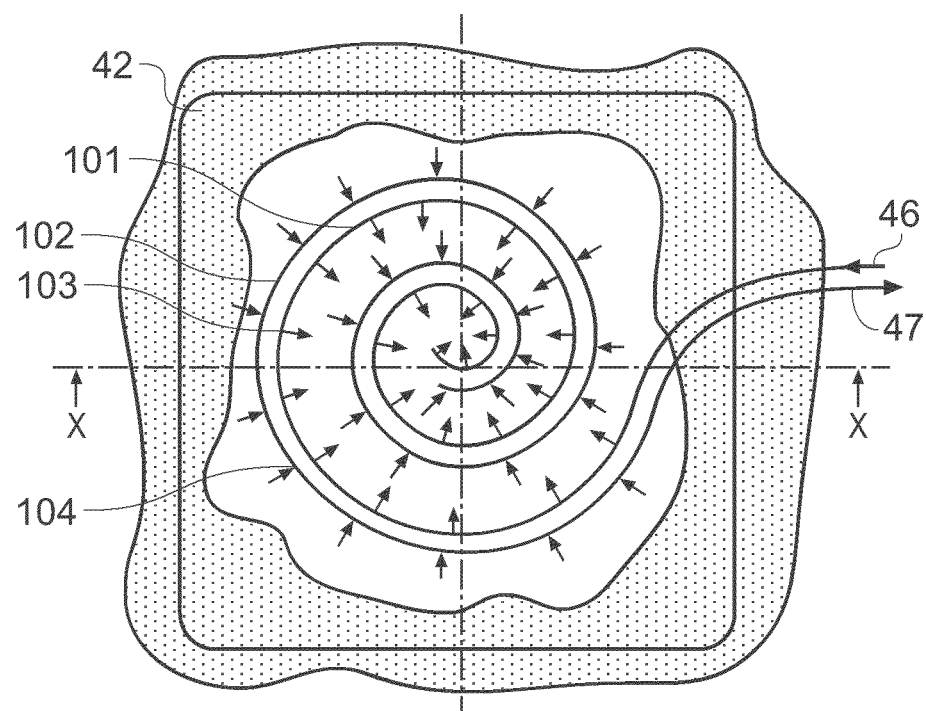
FIGS. 10a-b are various views of inlet and outlet manifold layouts for the wound dressings for respectively delivering fluid to, and collecting fluid from, the wound.
Figure 10B:
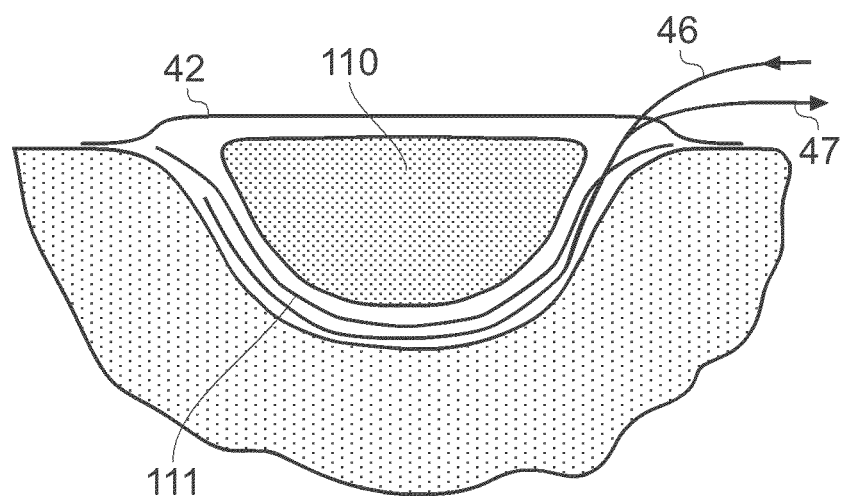

In FIGS. 9a and 9d, one layout of each of the pipes (101) and (102) as inlet pipe and outlet pipe manifolds is a spiral.

In FIG. 9b, the layout is a variant of that of FIGS. 9a and 9b, with the layout of the inlet manifold (101) being a full or partial torus, and the outlet manifold (102) being a radial pipe.

Referring to FIG. 9c, there is shown another suitable layout in which the inlet manifold (101) and the outlet manifold (102) run alongside each other over the wound bed in a boustrophedic pattern, i.e. in the manner of ploughed furrows.

Referring to FIGS. 10a to 10d, there are shown other suitable layouts for deeper wounds, which are the same as shown in FIGS. 9a to 9d. The square backing layer (42) however has a wound filler (110) under, and may be permanently attached to, the backing layer (42), with an adhesive film (not shown) or by heat-sealing, which is an inverted hemispherical solid integer, here a resilient elastomeric foam, formed of a thermoplastic, preferably a cross-linked plastics foam.

Under the latter is a circular upwardly dished sheet (111) which conforms to, but is a separate structure, permanently unattached to, the solid filler (110). Through the sheet (111) pass the inlet pipe (46) and the outlet pipe (47), to run over the wound bed. These pipes (101) and (102) again have a blind bore with orifices (103) and (104) along the pipes (101) and (102).

Alternatively (as in FIGS. 6a and 6b), where appropriate the dressing may be provided in a form in which the circular upwardly dished sheet (111) functions as the backing layer and the solid filler (110) sits on the sheet (42) as the backing layer, rather than under it. The filler (110) is held in place with an adhesive film or tape, instead of the backing layer (42).

Figures 11A, 11B, 11C:
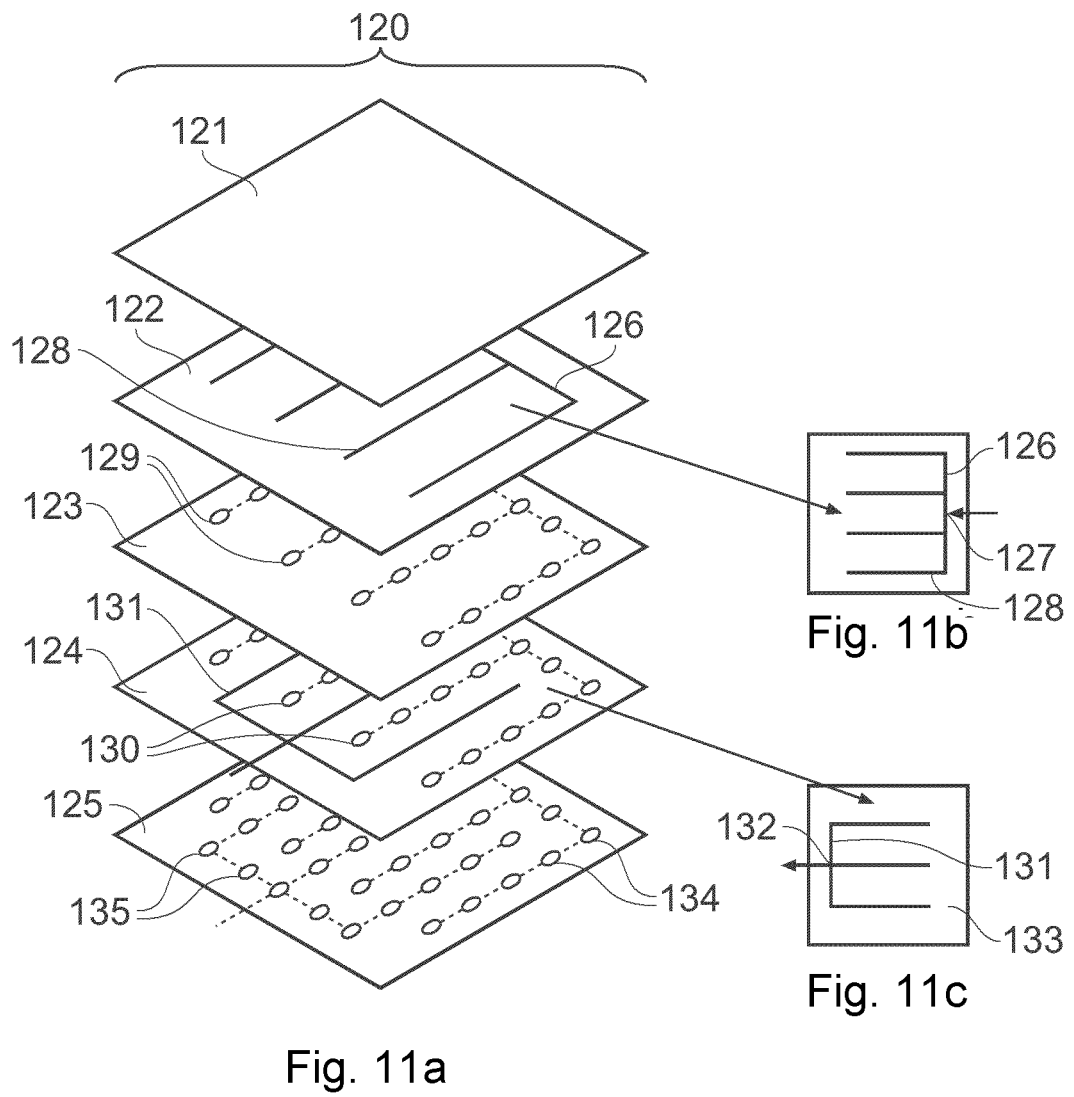

In FIGS. 11a to 11c, inlet and outlet manifolds for the wound dressings for respectively delivering fluid to, and collecting fluid from, the wound, are formed by slots in and apertures through layers permanently attached to each other in a stack.

Thus, in FIG. 11a there is shown an exploded isometric view of an inlet manifold and outlet manifold stack (120) of five square coterminous thermoplastic polymer layers, being first to fifth layers (121) to (125), each attached with an adhesive film (not shown) or by heat-sealing to the adjacent layer in the stack (120).

The topmost (first) layer (121) (which is the most distal in the dressing in use) is a blank square capping layer.

The next (second) layer (122), shown in FIG. 11b out of the manifold stack (120), is a square layer, with an inlet manifold slot (126) through it. The slot (126) runs to one edge (127) of the layer (122) for connection to a mating end of a fluid inlet tube ((not shown), and spreads into four adjacent branches (128) in a parallel array with spaces therebetween.

The next (third) layer (123) is another square layer, with inlet manifold apertures (129) through the layer (123) in an array such that the apertures (129) are in register with the inlet manifold slot (126) through the second layer (122) (shown in FIG. 11b).

The next (fourth) layer (124), shown in FIG. 11c out of the manifold stack (120), is another square layer, with inlet manifold apertures (130) through the layer (124) in an array such that the apertures (130) are in register with the apertures (129) through the third layer (123). It also has an outlet manifold slot (131) through it. The slot (131) runs to one edge (132) of the layer (124) on the opposite side of the manifold stack (120) from the edge (127) of the layer (122), for connection to a mating end of a fluid outlet tube (not shown). It spreads into three adjacent branches (133) in a parallel array in the spaces between the apertures (130) in the layer (124) and in register with the spaces between the apertures (129) in the layer (122).

The final (fifth) layer (125) is another square layer, with inlet manifold apertures (134) through the layer (125) in an array such that the apertures (134) are in register with the inlet manifold apertures (130) through the fourth layer (124) (in turn in register with the apertures (129) through the third layer (123)). It also has outlet manifold apertures (135) in the layer (125) in an array such that the apertures (135) are in register with the outlet manifold slot (131) in the fourth layer (124).

It will be seen that, when the layers (121) to (125) are attached together to form the stack (120), the topmost (first) layer (121), the inlet manifold slot (126) through the second layer (122), and the third layer (123) cooperate to form an inlet manifold in the second layer (122), which in use is connected to a mating end of a fluid inlet tube (not shown).

The inlet manifold slot (126) through the second layer (122), and the inlet manifold apertures (129), (130) and (134) through the layers (123), (124) and (125), all being mutually in register, cooperate to form inlet manifold conduits though the third to fifth layers (123), (124) and (125) between the inlet manifold in the second layer (122) and the proximal face (136) of the stack (120).

The third layer (121), the outlet manifold slot (131) through the fourth layer (124), and the fifth layer (125) cooperate to form an outlet manifold in the fourth layer (124), which is in use is connected to a mating end of a fluid outlet tube (not shown).

The outlet manifold slot (131) through the fourth layer (124), and the outlet manifold apertures (135) through the fifth layer (125), being mutually in register, cooperate to form outlet manifold conduits though the fifth layer (125) between the outlet manifold in the fourth layer (124) and the proximal face (136) of the stack (120).

Figure 12:
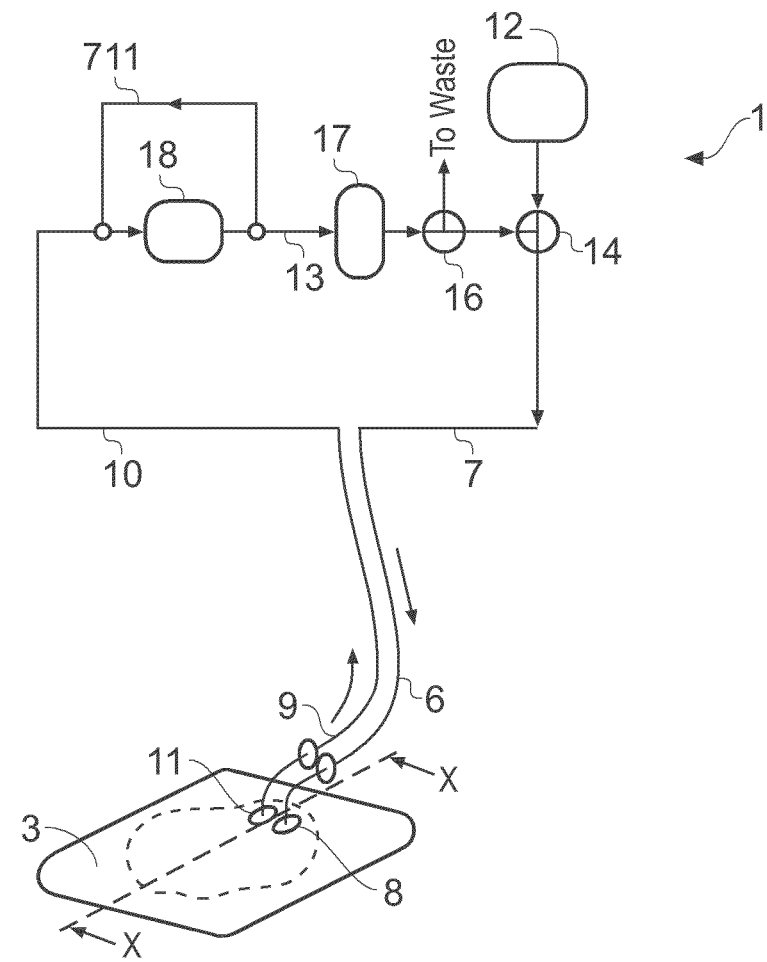
FIG. 12 is a schematic view of an apparatus for aspirating, irrigating and/or cleansing a wound. It has a single-phase system means for fluid cleansing in the form of an ultrafiltration unit. In one embodiment, it has a single-phase system means for fluid cleansing in the form of a container, e.g. a canister, cartridge or cassette, with a chamber or compartment that contains a cell or tissue component, through which the wound exudate or a mixture with irrigant passes.
Figure 12:
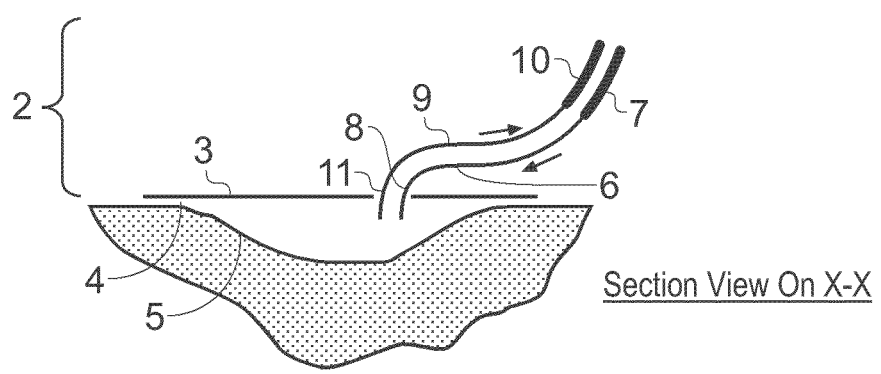

Referring to FIG. 12, the apparatus (1) for aspirating, irrigating and/or cleansing wounds is a variant of the apparatus (1) of FIG. 1b. It has bypass (711) around the pump (17), as a protection of the pump against any blockage in the system. It is activated automatically by appropriate means, e.g. it is normally blocked by a bursting disc (not shown), or a pressure-activated motorised valve. An alternative to the by-pass (711) is a pressure sensor in the system that will detect excessive load or pressure, and shut down the pump.

Figure 13:
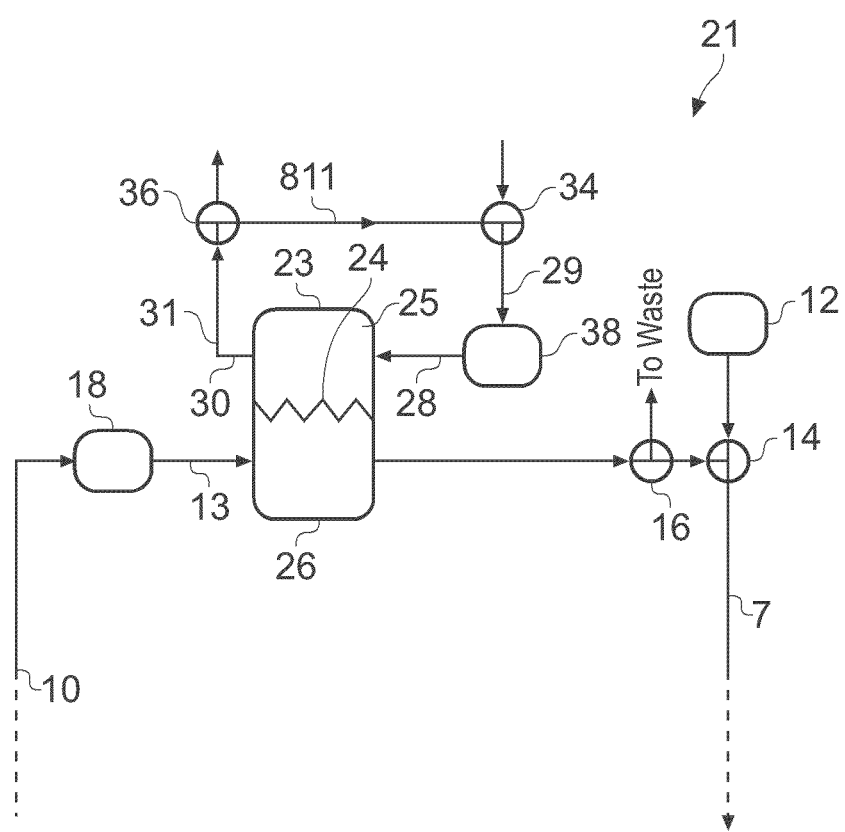
FIG. 13 is a schematic view of an apparatus for aspirating, irrigating and/or cleansing a wound. It has a two-phase system means for fluid cleansing in the form of a dialysis unit, or a biphasic extraction unit. In one embodiment, it has a two-phase system means for fluid cleansing in the form of a dialysis container, e.g. a canister, cartridge or cassette, with one compartment through which the circulating fluid from the wound and the fluid reservoir passes and is separated by an integer that is permeable to materials in the circulating fluid in the apparatus from a second compartment containing cells or tissue, through which passes a cleansing fluid.

Referring to FIG. 13, the apparatus (1) for aspirating, irrigating and/or cleansing wounds is a variant of the apparatus (1) of FIG. 2.

The latter is a two-phase system with a dialysis unit (23), but is one in which dialytic fluid passes only once across the surface of the dialytic membrane (24) in the first chamber (25) from a dialysate reservoir (not shown) to waste via a second bleed T-valve (36) into, e.g. a collection bag (not shown).

This variant has a dialysate recirculation tube (811) running between a first T-valve (34) on the inlet side of the dialysate pump (38) and a second T-valve (36) to permit the pump (23) to recirculate the dialysate once the circuit is primed in multiple passes through the dialysis unit (23).

The operation of the system will be apparent to the skilled person.

Figure 14A:
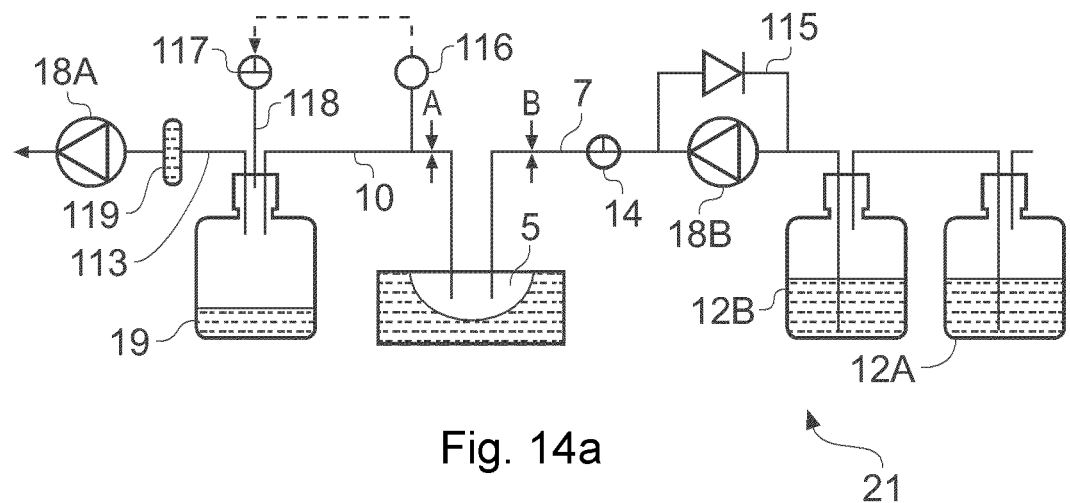
FIGS. 14a to d are variants of a two-pump system with essentially identical, and identically numbered, components as in FIG. 2, except that there is a pump bypass loop (in all except FIG. 14c), a filter downstream of the aspirate collection vessel, and a bleed regulator, such as a rotary valve, connected to the fluid offtake tube or to the wound space, for the regulation of the positive or negative pressure applied to the wound.

Referring to FIG. 14a, the apparatus (21) is a variant two-pump system with essentially identical, and identically numbered, components as in FIG. 3.

Thus, there is a means for supply flow regulation, here a valve (14) in the fluid supply tube (7) from the fluid reservoir (12A), and a first device for moving fluid through the wound (5), here a fixed-speed diaphragm pump (18A), e.g. preferably a small portable diaphragm pump, acting not on the fluid aspiration tube (13), but on an air aspiration tube (113) downstream of and away from an aspirate collection vessel (19) to apply a low negative pressure on the wound through the aspirate collection vessel (19); with a second device for moving fluid through the wound (5), here a fixed-speed peristaltic pump (18B), e.g. preferably a small portable peristaltic pump, applied to the irrigant in the fluid supply tube (7) upstream of and towards the wound dressing, the first device (18A) and second device (18B), and the valve (14) in the fluid supply tube (7), providing means for providing simultaneous aspiration and irrigation of the wound (5), such that fluid may be supplied to fill the flowpath from the fluid reservoir via the fluid supply tube (via the means for supply flow regulation) and moved by the devices through the flow path.

There is no means for aspirate flow regulation, e.g. a valve connected to the fluid offtake tube (10).

Since the first device (18A) and second device (18B) are fixed-speed, the valve (14) in the fluid supply tube (7) provides the sole means for varying the irrigant flow rate and the low negative pressure on the wound.

The following extra features are present:

The second device, the fixed-speed peristaltic pump (18B), is provided with means for avoiding over-pressure, in the form of a bypass loop with a non-return valve (115). The loop runs from the fluid supply tube (7) downstream of the pump (18B) to a point in the fluid supply tube (7) upstream of the pump (18B).

A pressure monitor (116) connected to the fluid offtake tube (10) has a feedback connection to a bleed regulator, here a motorised rotary valve (117) on a bleed tube (118) running to and centrally penetrating the top of the aspirate collection vessel (19). This provides means for holding the low negative pressure on the wound at a steady level.

A filter (119) downstream of the aspirate collection vessel (19) prevents passage of gas- (often air-) borne particulates, including liquids and micro-organisms, from the irrigant and/or exudate that passes into the aspirate collection vessel (19) into the first device (18A), whilst allowing the carrier gas to pass through the air aspiration tube (113) downstream of it to the first device (18A). The operation of the apparatus is as described hereinbefore Referring to FIG. 14b, this shows an alternative layout of the essentially identical, and identically numbered, components in FIG. 14a downstream of point A in FIG. 14a. The bleed tube (118) runs to the air aspiration tube (113) downstream of the filter (119), rather than into the aspirate collection vessel (19). This provides means for holding the low negative pressure on the wound at a steady level. The operation of the apparatus is as described hereinbefore Referring to FIG. 14c, this shows an alternative layout of the essentially identical, and identically numbered, components in FIG. 14a upstream of point B in FIG. 14a. The second device (18B) is a variable-speed pump, and the valve (14) in the fluid supply tube (7) is omitted. The second device (18B) is the sole means for varying the irrigant flow rate and the low negative pressure on the wound. The operation of the apparatus is as described hereinbefore Referring to FIG. 14d, this shows an alternative layout of the essentially identical, and identically numbered, components in FIG. 14a downstream of point B in FIG. 14a. The pressure monitor (116) is connected to a monitor offtake tube (120) and has a feedback connection to the bleed regulator, motorised rotary valve (117) on a bleed tube (118) running to the monitor offtake tube (120). This provides means for holding the low negative pressure on the wound at a steady level. The operation of the apparatus is as described hereinbefore Referring to FIG. 15a, this shows another alternative layout of the essentially identical, and identically numbered, components in FIG. 14a downstream of point B in FIG. 14a. The pressure monitor (116) is connected to a monitor offtake tube (120) and has a feedback connection to a means for aspirate flow regulation, here a motorised valve (16) in the air aspiration tube (113) downstream of the filter (119). This provides means for aspirate flow regulation and for holding the low negative pressure on the wound at a steady level. The operation of the apparatus is as described hereinbefore Referring to FIG. 15b, this shows another alternative layout of the essentially identical, and identically numbered, components in FIG. 14a downstream of point B in FIG. 14a. The pressure monitor (116) is connected to a monitor offtake tube (120) and has a feedback connection to a means for aspirate flow regulation, here a motorised valve (16), in the fluid offtake tube (10) upstream of the aspirate collection vessel (19). This provides means for aspirate flow regulation and for holding the low negative pressure on the wound at a steady level. The operation of the apparatus is as described hereinbefore Referring to FIG. 15c, this shows another alternative layout of the essentially identical, and identically numbered, components in FIG. 14a downstream of point B in FIG. 14a. The pressure monitor (116) is connected to a monitor offtake tube (120) and has a feedback connection to a variable-speed first device (18A), here a variable-speed pump, downstream of the filter (119), and the valve (16) in the fluid offtake tube (10) is omitted. This provides means for aspirate flow regulation and for holding the low negative pressure on the wound at a steady level. The operation of the apparatus is as described hereinbefore.

Figure 16A:
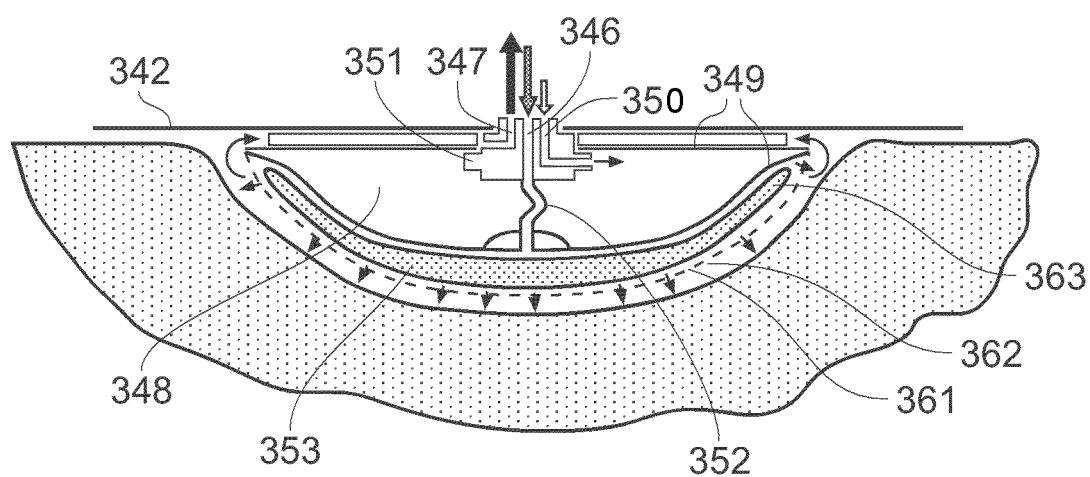
Figure 16B:
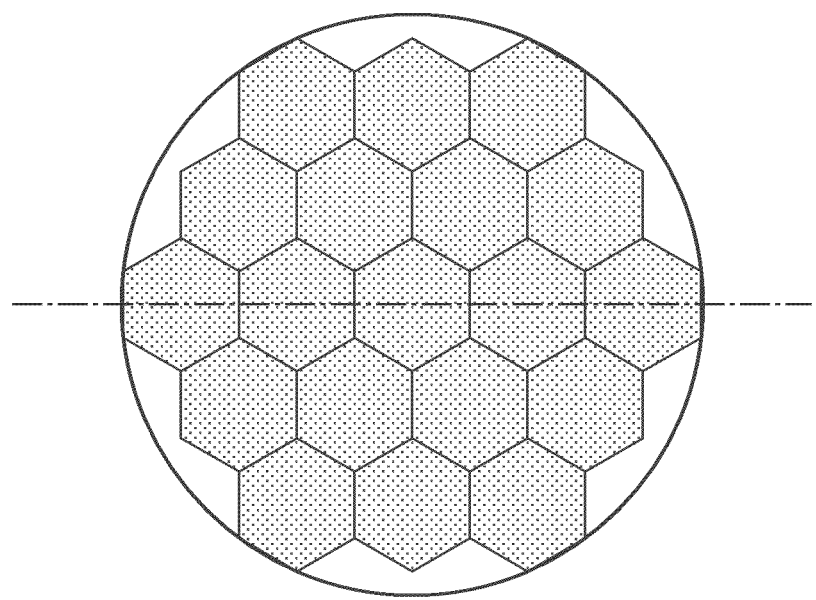
Figure 17:
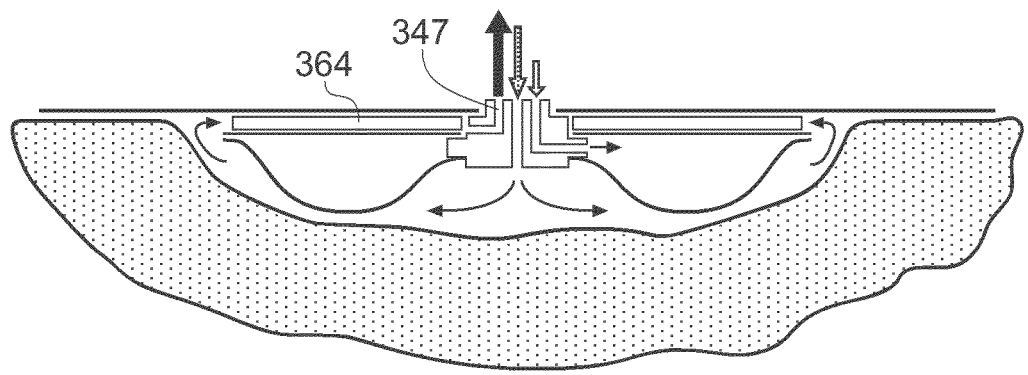
Figure 18:
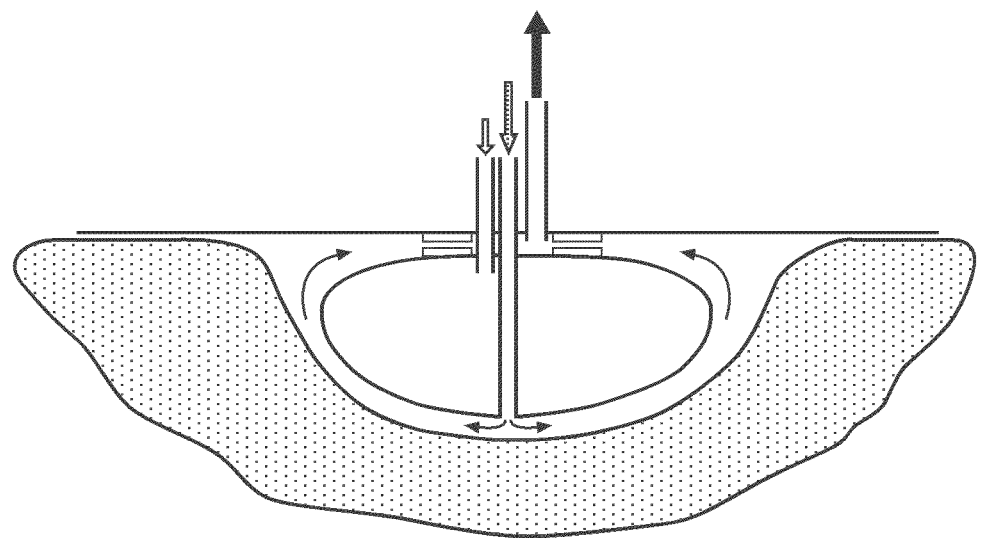

Referring to FIGS. 16 to 18, these forms of the dressing are provided with a wound filler (348) under a circular backing layer (342). This comprises respectively a generally downwardly domed or toroidal, or oblately spheroidal conformable hollow body, defined by a membrane (349) which is filled with a fluid, here air or nitrogen, that urges it to the wound shape. The filler (348) is permanently attached to the backing layer via a boss (351), which is e.g. heat-sealed to the backing layer (342). An inflation inlet pipe (350), inlet pipe (346) and outlet pipe (347) are mounted centrally in the boss (351) in the backing layer (342) above the hollow body (348). The inflation inlet pipe (350) communicates with the interior of the hollow body (348), to permit inflation of the body (348). The inlet pipe (346) extends in a pipe (352) effectively through the hollow body (348). The outlet pipe (347) extends radially immediately under the backing layer (342).

In FIG. 16, the pipe (352) communicates with an inlet manifold (353), formed by a membrane (361) with apertures (362) that is permanently attached to the filler (348) by heat-sealing. It is filled with foam (363) formed of a suitable material, e.g. a resilient thermoplastic. Preferred materials include reticulated filtration polyurethane foams with small apertures or pores.

In FIG. 17, the outlet pipe (347) communicates with a layer of foam (364) formed of a suitable material, e.g. a resilient thermoplastic. Again, preferred materials include reticulated filtration polyurethane foams with small apertures or pores.

In all of FIGS. 16, 17 and 18, in use, the pipe (346) ends in one or more openings that deliver the irrigant fluid directly from the wound bed over an extended area. Similarly, the outlet pipe (347) effectively collects the fluid radially from the wound periphery when the dressing is in use.

Figure 19A:
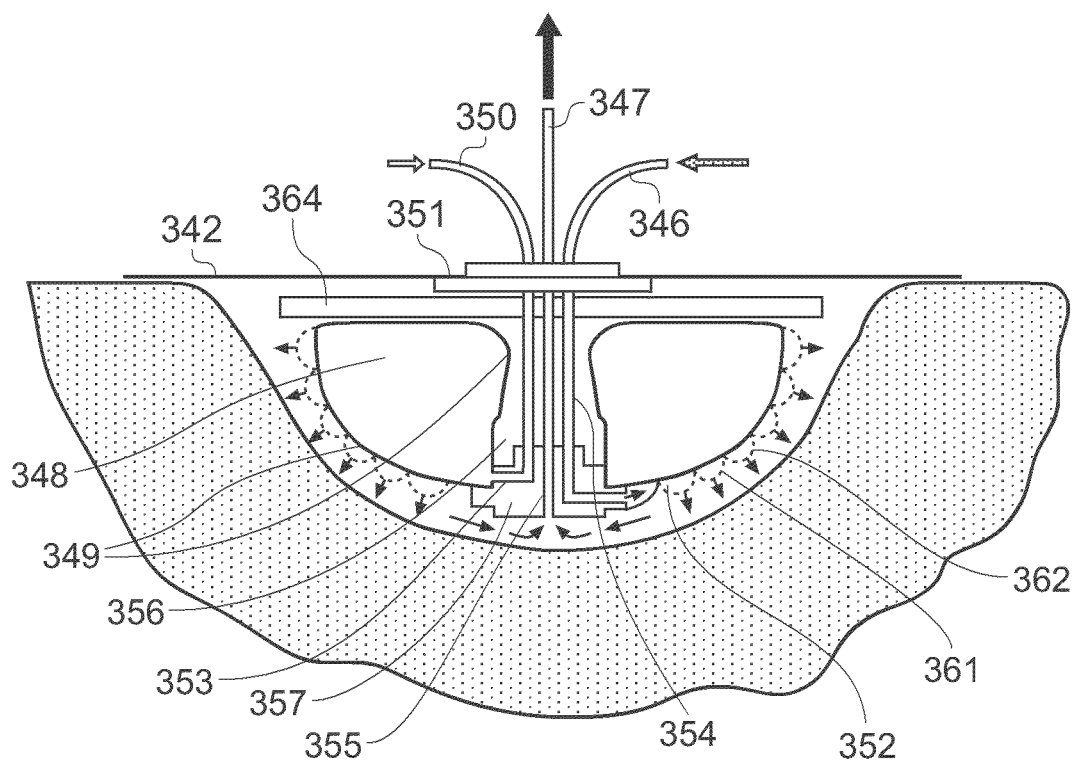
FIGS. 19a-b are cross-sectional views of conformable wound dressings.
Figure 19B:
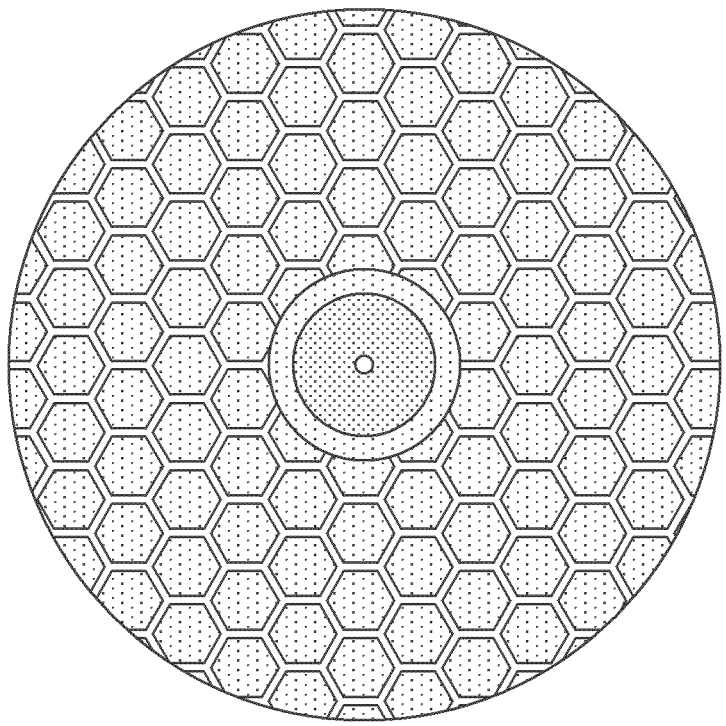

Referring to FIG. 19, the dressing is also provided with a wound filler (348) under a circular backing layer (342). This also comprises a generally toroidal conformable hollow body, defined by a membrane (349) which is filled with a fluid, here air or nitrogen, that urges it to the wound shape. The filler (348) may be permanently attached to the backing layer (342) via a first boss (351) and a layer of foam (364) formed of a suitable material, e.g. a resilient thermoplastic. Again, preferred materials include reticulated filtration polyurethane foams with small apertures or pores. The first boss (351) and foam layer (364) are respectively heat-sealed to the backing layer (342) and the boss (351). An inflation inlet pipe (350), inlet pipe (346) and outlet pipe (347) are mounted centrally in the first boss (351) in the backing layer (342) above the toroidal hollow body (348).

The inflation inlet pipe (350), inlet pipe (346) and outlet pipe (347) respectively each extend in a pipe (353), (354) and (355) through a central tunnel (356) in the hollow body (348) to a second boss (357) attached to the toroidal hollow body (348). The pipe (353) communicates with the interior of the hollow body (348), to permit inflation of the body (348). The pipe (354) extends radially through the second boss (357) to communicate with an inlet manifold (352), formed by a membrane (361) that is permanently attached to the filler (348) by heat-sealing in the form of a reticulated honeycomb with openings (362) that deliver the irrigant fluid directly to the wound bed over an extended area. The pipe (355) collects the fluid flowing radially from the wound center when the dressing is in use.

This form of the dressing is a more suitable layout for deeper wounds

Figure 20:
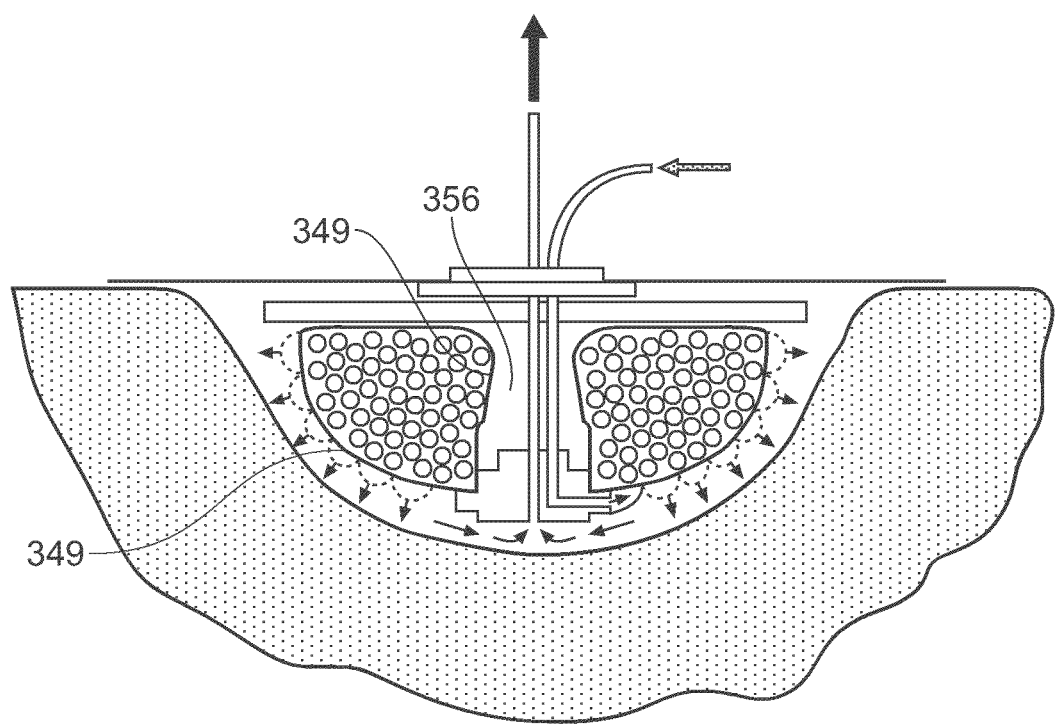

In FIG. 20, the dressing is similar to that of FIG. 19, except that the toroidal conformable hollow body, defined by a membrane (349), is filled with a fluid, here solid particulates, such as plastics crumbs or beads, rather than a gas, such as air or an inert gas, such as nitrogen or argon, and the inflation inlet pipe (350) and pipe (353) are omitted from the central tunnel (356). Examples of contents for the body (348) also include gels, such as silicone gels or preferably cellulosic gels, for example hydrophilic cross-linked cellulosic gels, such as Intrasite™ cross-linked materials. Examples also include aerosol foams, and set aerosol foams, e.g. CaviCare™ foam.

Figure 21A:
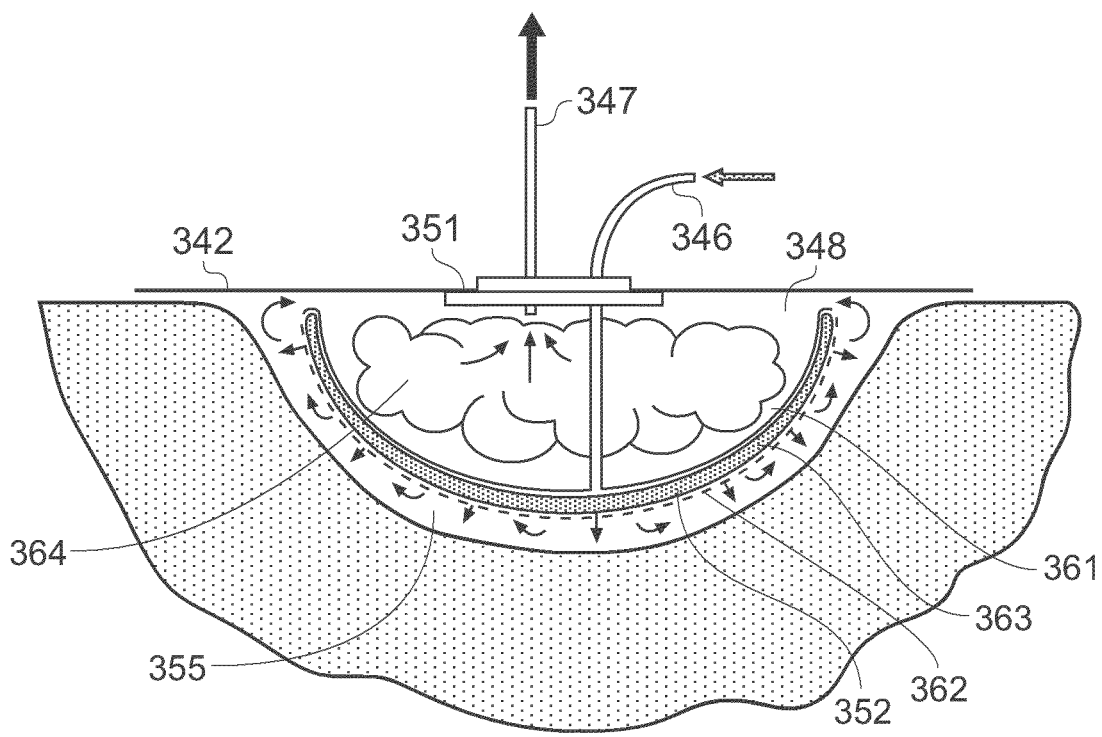
FIGS. 21a-b are cross-sectional views of conformable wound dressings.
Figure 21B:
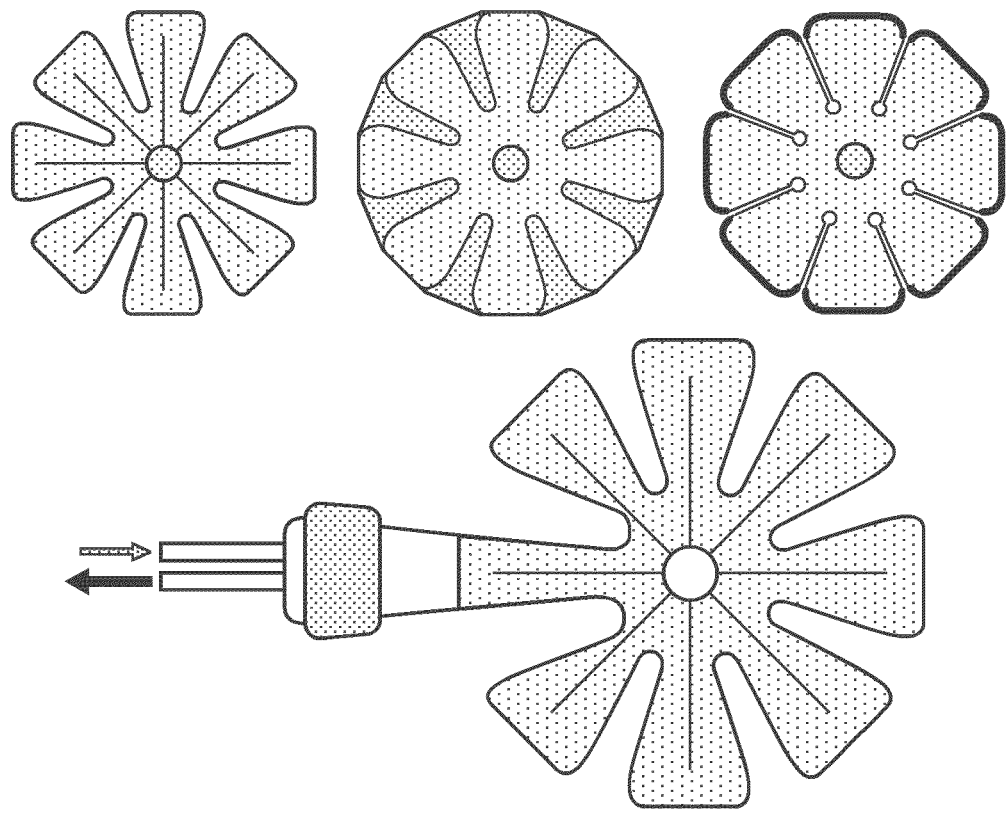
Figure 22:
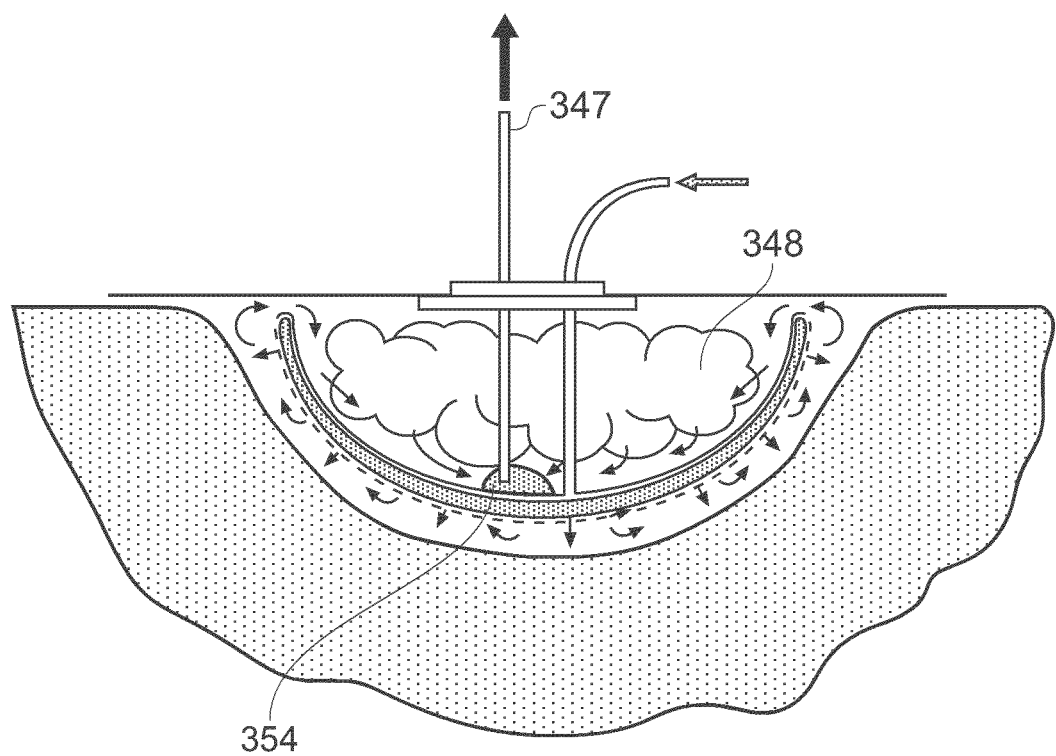

Referring to FIGS. 21 and 22, another form for deeper wounds is shown. This comprises a circular backing layer (342) and a chamber (363) in the form of a deeply indented disc much like a multiple Maltese cross or a stylised rose. This is defined by an upper impervious membrane (361) and a lower porous film (362) with apertures (352) that deliver the irrigant fluid directly from the wound bed over an extended area. A number of configurations of the chamber (363) are shown, all of which are able to conform well to the wound bed by the arms closing in and possibly overlapping in insertion into the wound. In a particular design of the chamber (363), shown lowermost, on of the arms extended and provided with an inlet port at the end of the extended arm. This provides the opportunity for coupling and decoupling the irrigant supply remote from the dressing and the wound in use. An inlet pipe (346) and outlet pipe (347) are mounted centrally in a boss (351) in the backing layer (342) above the chamber (363). The inlet pipe (346) is permanently attached to, and communicate with the interior of, the chamber (363), which thus effectively forms an inlet manifold. The space above the chamber (363) is filled with a loose gauze packing (364).

In FIG. 21, the outlet pipe (347) collects the fluid from the interior of the dressing from just under the wound-facing face of the backing layer (342).

A variant of the dressing of FIG. 21 is shown in FIG. 22. The outlet pipe (347) is mounted to open at the lowest point of the space above the chamber (363) into a piece of foam (354).

Figure 23:
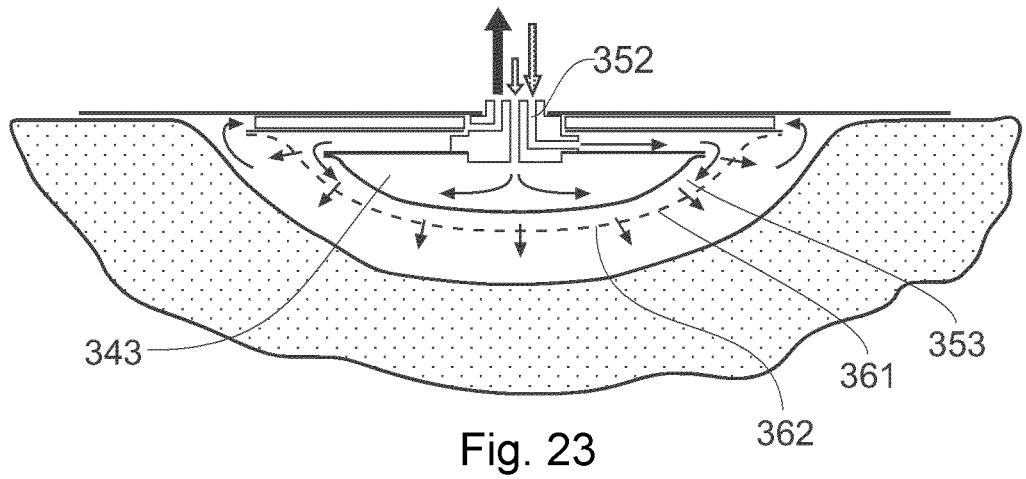

In FIG. 23, the dressing is similar to that of FIG. 16, except that the inlet pipe (352) communicates with an inlet manifold (353), formed by a membrane (361) with apertures (362), over the upper surface of the generally downwardly domed wound hollow filler, rather than through it.

Figure 24:
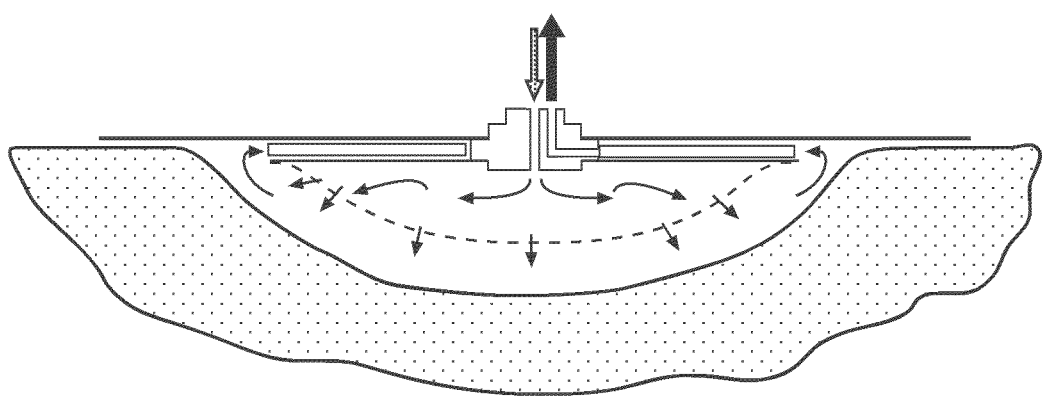

In FIG. 24, the generally downwardly domed annular wound hollow filler is omitted.

Figure 25:
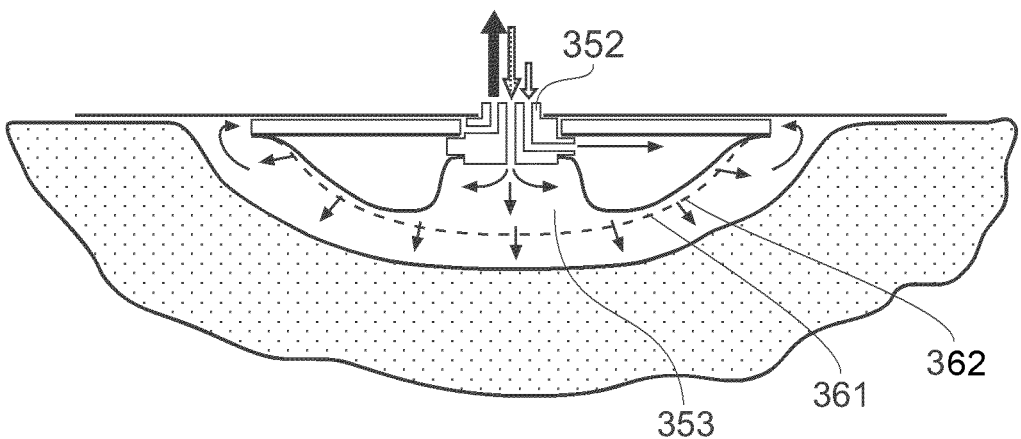

In FIG. 25, the dressing is similar to that of FIG. 17, with the addition of an inlet manifold (353), formed by a membrane (361) with apertures (362), over the lower surface of the generally downwardly domed annular wound hollow filler.

Figure 26:
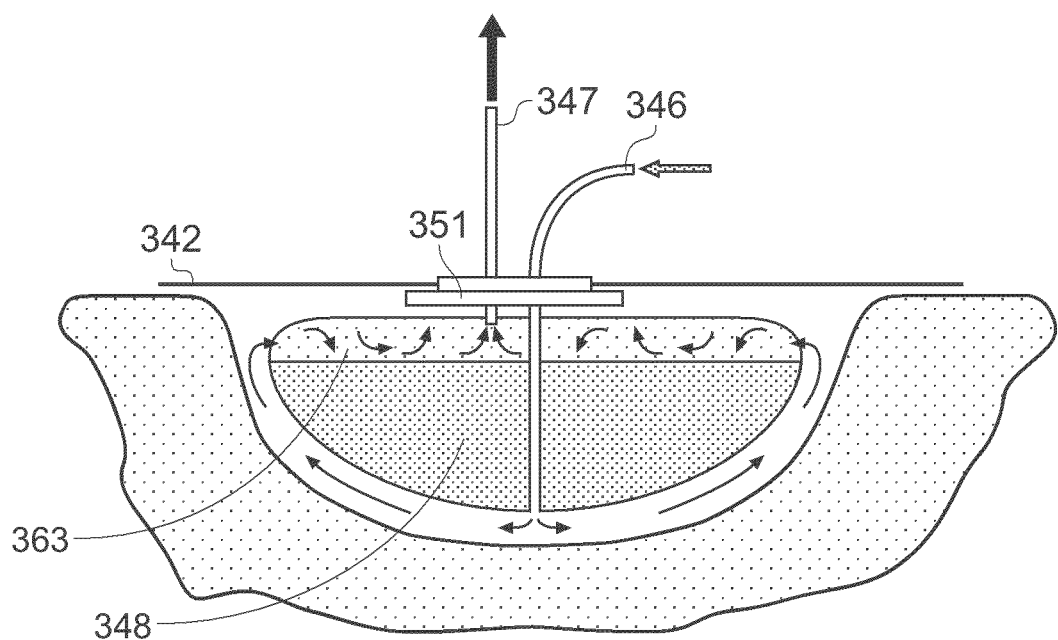

Referring to FIG. 26, another form for deeper wounds is shown. An inlet pipe (346) and outlet pipe (347) are mounted centrally in a boss (351) in the backing layer (342) above a sealed-off foam filler (348). The inlet pipe (346) is permanently attached to and passes through the filler (348) to the wound bed. The outlet pipe (347) is attached to and communicates with the interior of, a chamber (363) defined by a porous foam attached to the upper periphery of the filler (348). The chamber (363) thus effectively forms an outlet manifold.

Figure 27:
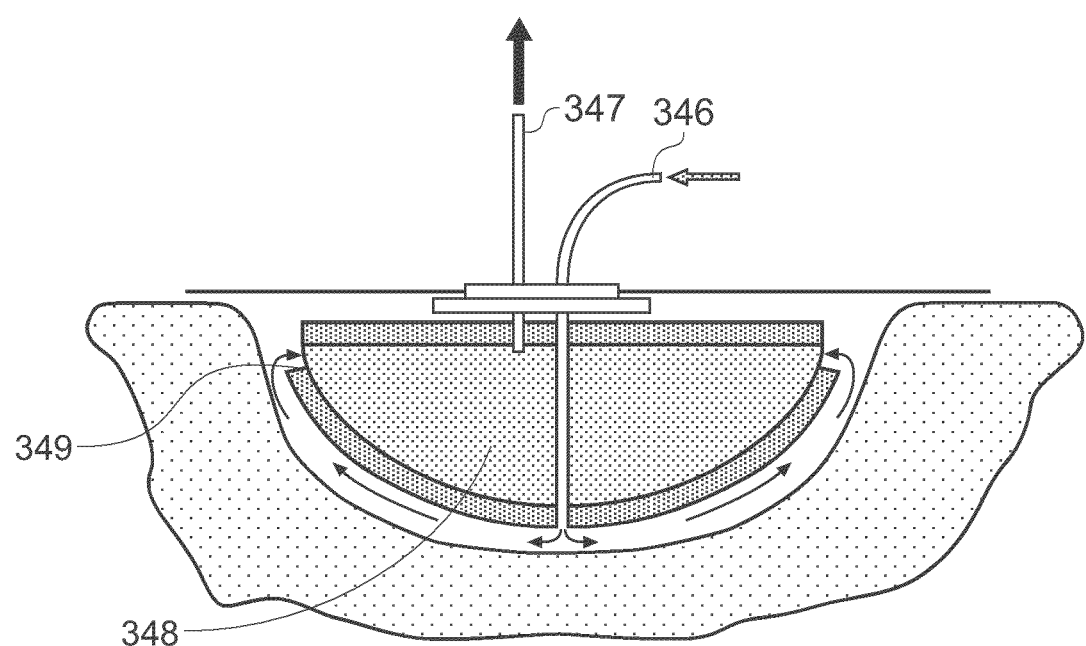

In FIG. 27, the foam filler (348) is only partially sealed-off. The inlet pipe (346) is permanently attached to and passes through the filler (348) to the wound bed. The outlet pipe (347) is attached to and communicates with the interior of the foam of the filler (348). Fluid passes into an annular gap (349) near the upper periphery of the filler (348) into the foam, which thus effectively forms an outlet manifold.

Figure 28:
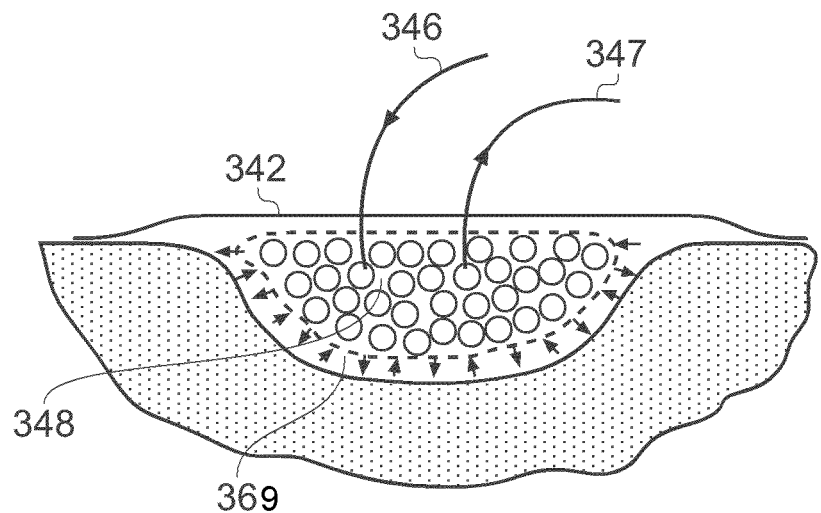
Figure 29:
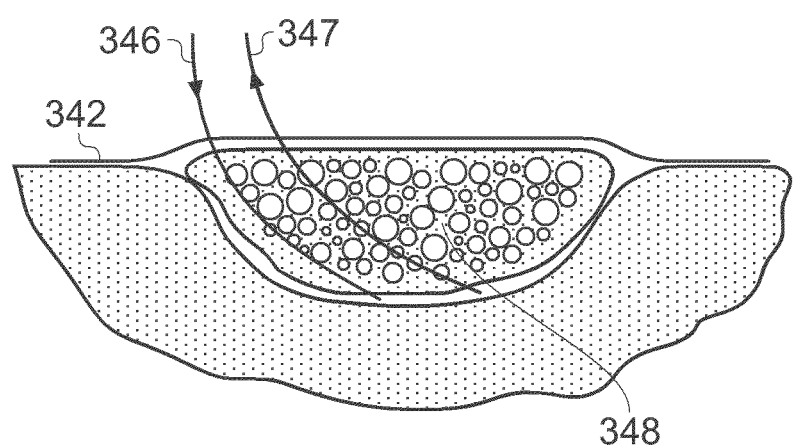

FIGS. 28 and 29 show dressings in which the inlet pipe (346) and outlet pipe (347) pass through the backing layer (342).

In FIG. 28, they communicate with the interior of a porous bag filler (348) defined by a porous film (369) and filled with elastically resilient plastics bead or crumb.

In FIG. 29, they communicate with the wound space just below a foam filler (348). The foam (348) may be Cavi-Care™ foam, injected and formed in situ around the pipes (346) and (347).

Figure 30A:
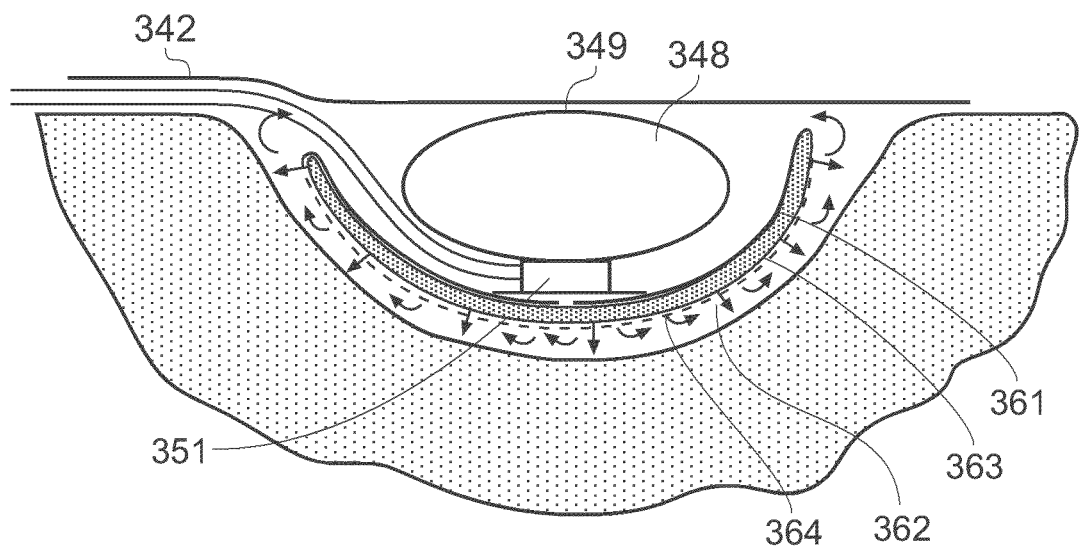
FIG. 30a is a plan view and FIG. 30b a cross-sectional view of a further conformable wound dressings.
Figure 30B:
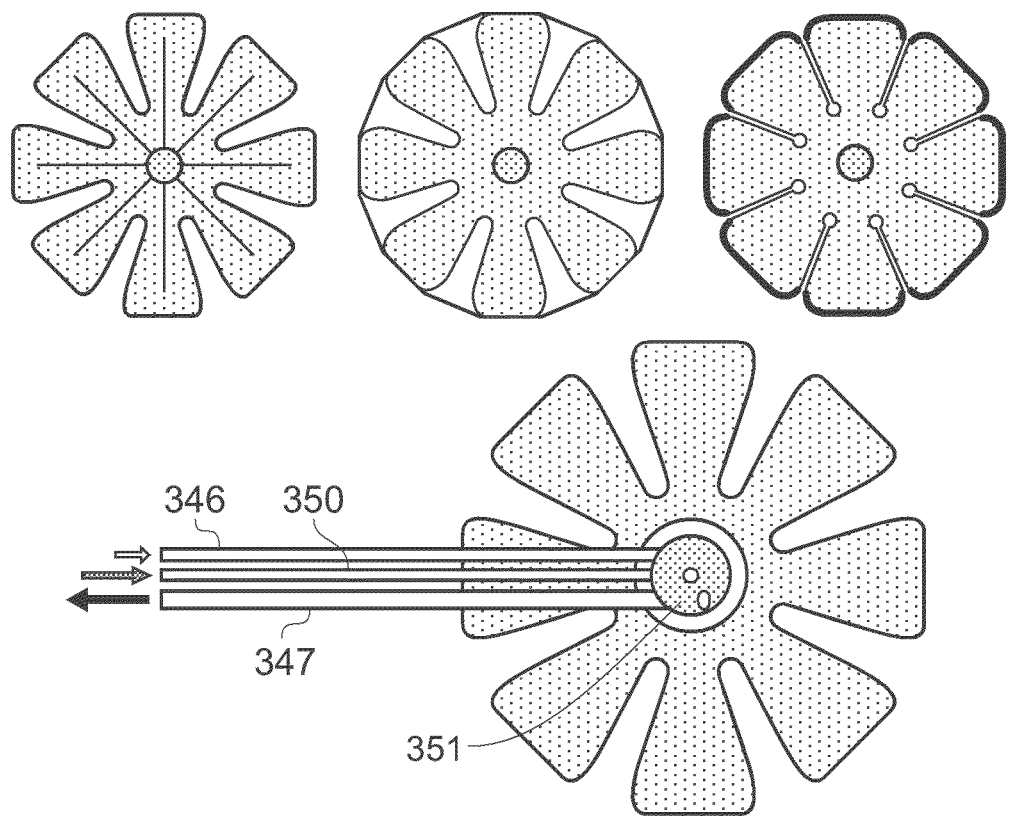

Referring to FIG. 30, another form for deeper wounds is shown. This comprises a circular, or more usually square or rectangular backing layer (342) and a chamber (363) in the form of a deeply indented disc much like a multiple Maltese cross or a stylised rose. This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 30b, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that is filled with a fluid, here air or nitrogen, that urges it to the wound shape.

A moulded hat-shaped boss (351) is mounted centrally on the upper impervious membrane (361) of the chamber (363). It has three internal channels, conduits or passages through it (not shown), each with entry and exit apertures. The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing, and extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Figure 31A:
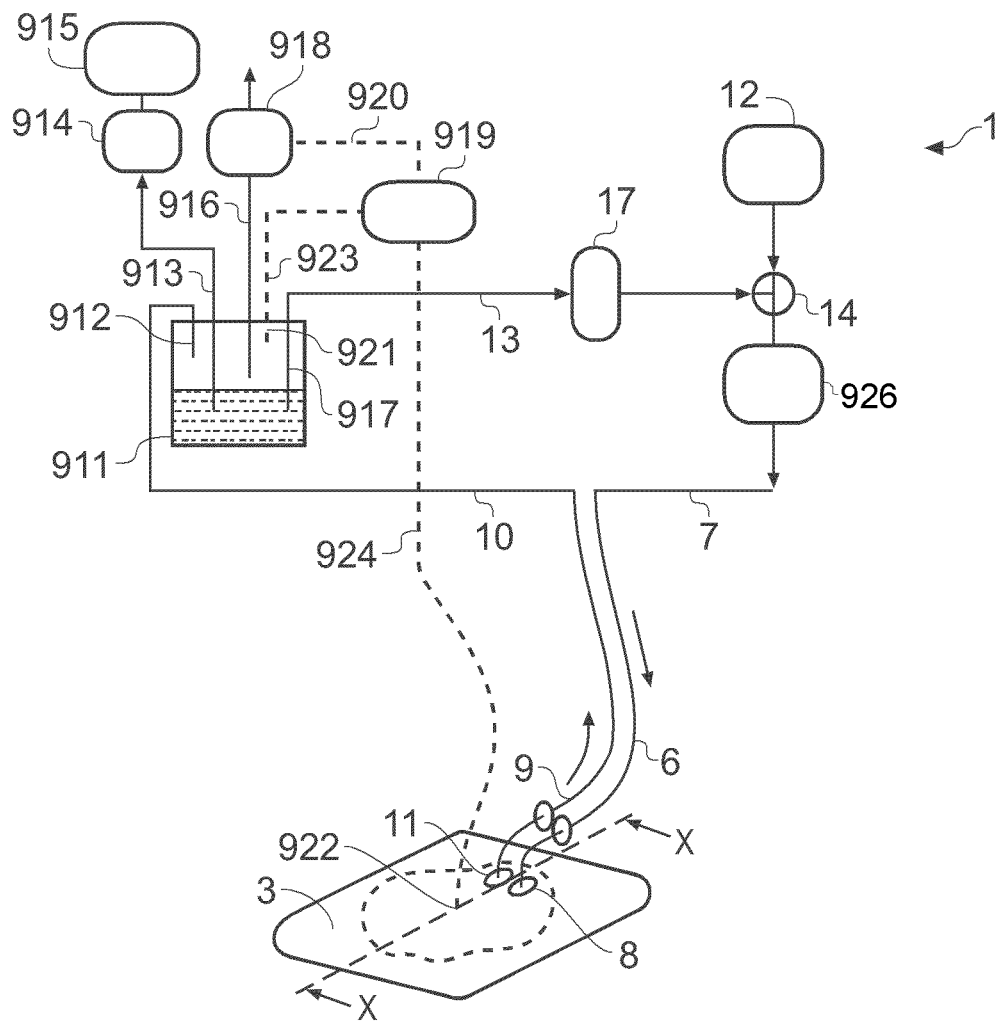
FIGS. 31a and 31b are schematic views of an apparatus for aspirating, irrigating and/or cleansing a wound according to one embodiment of the present invention. It has a single-phase system means for fluid cleansing in the form of an ultrafiltration unit.
Figure 31A:
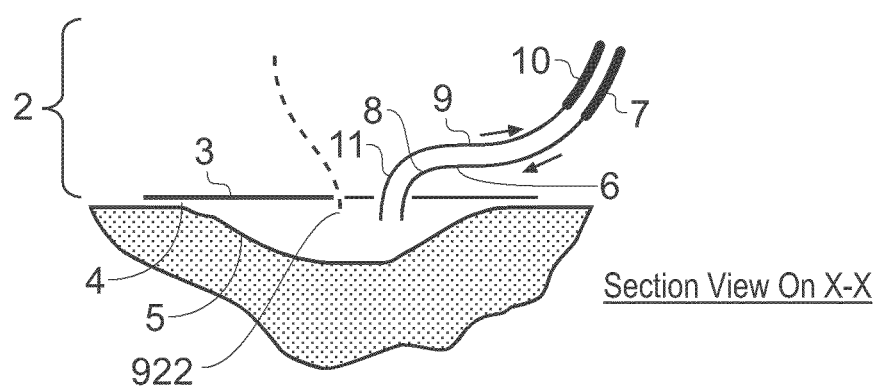

Referring to FIG. 31a, the apparatus (1) for aspirating, irrigating and/or cleansing wounds is a major variant of the apparatus shown in FIG. 1b.

The device for moving fluid through the wound and means for fluid cleansing (17) in FIG. 1b is a peristaltic pump (18), e.g. preferably a small portable peristaltic pump, acting on the fluid circulation tube (13) downstream of the dressing (2) to apply a low negative pressure on the wound.

In the apparatus (1) shown in FIG. 31a, the peristaltic pump (18) is replaced by: (a) a peristaltic pump (926) acting on the fluid supply tube (7) upstream of the dressing (2), and (b) a vacuum pump assembly (918) with pressure regulating means, acting downstream of the dressing (2), to apply an overall low negative pressure in the wound space.

The vacuum pump assembly comprises a tank (911) with an inlet tube (912) connecting to the fluid circulation tube (13) and communicating with the upper part of the tank (911), a waste tube (913) connecting to a waste pump (914) with waste bag (915) and communicating with the lower part of the tank (911), a pump tube (916) connecting to a vacuum pump (918) and communicating with the upper part of the tank (911), and an outlet tube (917) connecting to the fluid circulation tube (13) to the means for cleansing (17) and communicating with the lower part of the tank (911).

The vacuum pump (918) is controlled by a pressure feedback regulator (919) through an electrical line (920), the regulator receiving signals from a tank sensor (921) in the upper part of the tank (911), and a dressing sensor (922) in the wound space respectively via lines (923) and (924).

The pressure feedback regulator (919) regulates the pressure at the wound and/or the tank (911).

If the amount of fluid in circulation becomes excessive, e.g. because the wound continues to exude heavily, the waste pump (914) may be started to transfer fluid from the lower part of the tank (911) to the waste bag (915).

Figure 31B:
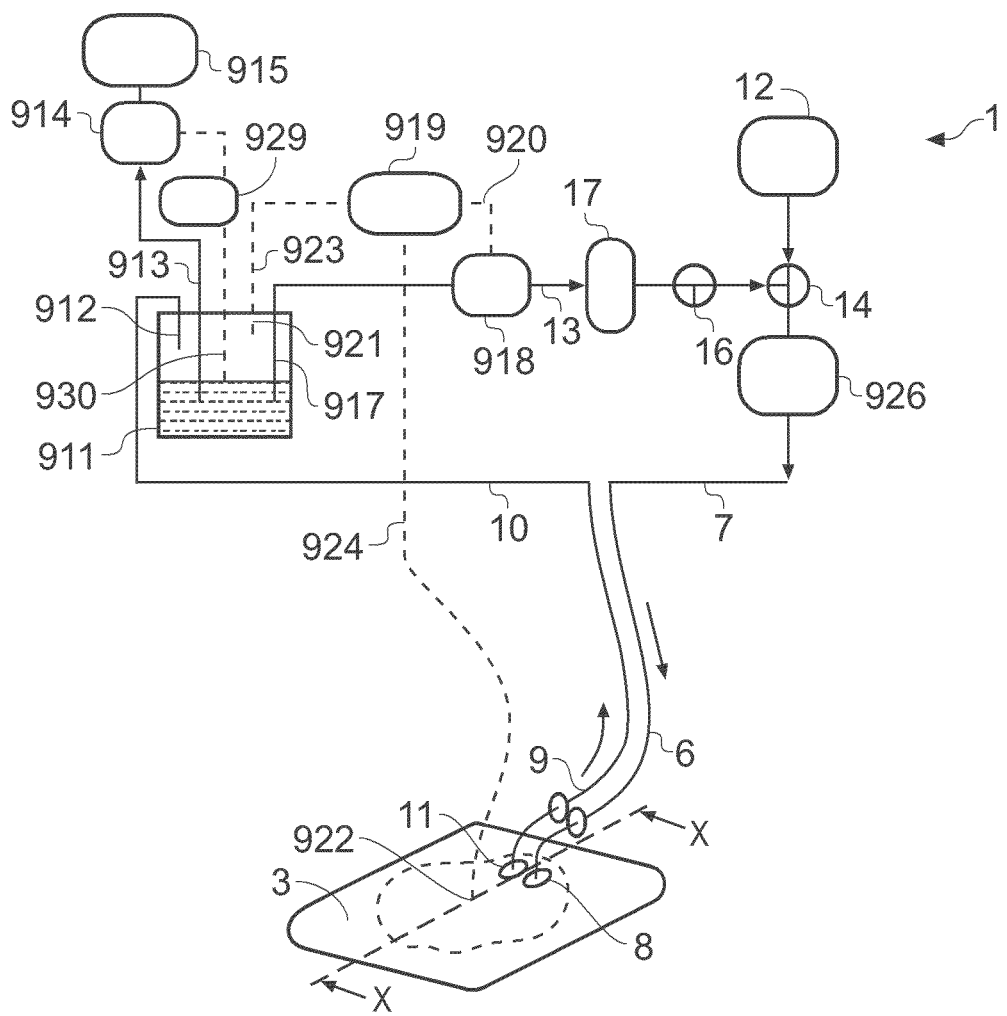
Figure 31B:
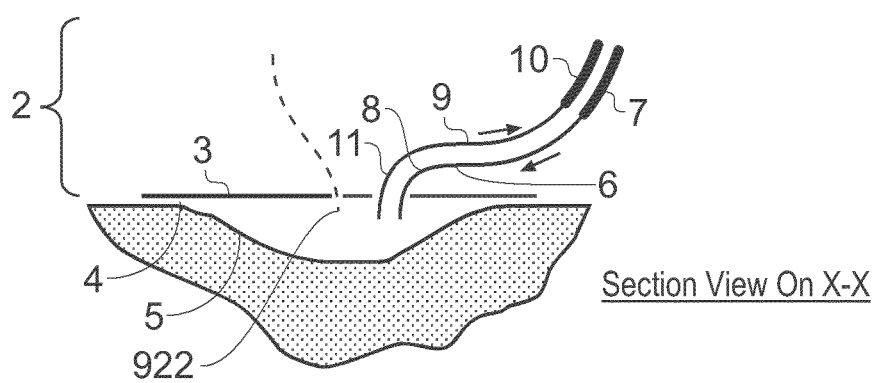

Referring to FIG. 31b, the apparatus is as described in FIG. 31a, except that the vacuum pump assembly comprises a tank (911) with an inlet tube (912) connecting to the fluid circulation tube (13) and communicating with the upper part of the tank (911), a waste tube (913) connecting to a waste pump (914) with waste bag (915) and communicating with the lower part of the tank (911), a pump tube (917) connecting to a vacuum pump (918) and communicating with the upper part of the tank (911), and connecting via the fluid circulation tube (13) to the means for cleansing (17) and communicating with the lower part of the tank (911).

Additionally, the waste pump (914) is controlled by a waste level feedback regulator (929) the regulator receiving signals from a tank sensor with electrical line (930) in the middle part of the tank (911).

The vacuum pump (918) either acts as a valve so that the pump tube 917 connecting to the vacuum pump (918) is normally blocked to prevent passage of air through it from the upper part of the tank (911) when the vacuum pump (918) is at rest, or the pump tube (917) is provided with a manual or motorised, e.g. pressure-activated motorised, valve (930) (not shown), so that the pump tube (917) connecting to the vacuum pump (918) may be blocked to prevent such passage.

The operation of the apparatus (1) is similar to that of the apparatus in FIG. 1b mutatis mutandis.

In use of the apparatus (1), the valve (16) is opened to a collection bag (not shown), and the T-valve (14) is turned to admit fluid from the fluid reservoir (part of the integer (12)) to the wound dressing through the fluid supply tube (7) and inlet pipe (6).

The pump (926) is started to nip the fluid recirculation tube (7) with the peripheral rollers on its rotor (not shown) to apply a low positive pressure on the wound.

The vacuum pump (918) either acts as a valve since it is at rest, or the valve (930) (not shown) is closed, so that the pump tube 917 is blocked to prevent passage of air through it from the upper part of the tank (911).

Irrigant pumped from the wound dressing (2) through the fluid offtake tube (10) is pumped through the lower part of the tank (911) up the outlet tube (917) via the means for cleansing (17) to the bleed T-valve (16) into, e.g. a collection bag (not shown).

The peristaltic pump (926) acting on the fluid supply tube (7) upstream of the dressing (2) is allowed to run until the apparatus is primed throughout the whole length of the apparatus flow path and excess fluid is voided to waste via the bleed T-valve (16) into the collection bag.

The T-valve (14) is then turned to switch from supply to recirculation, i.e. is set to close the wound to the fluid reservoir (part of the integer (12)) but to admit fluid into the wound from the fluid recirculation tube (13), and the bleed T-valve (16) is simultaneously closed.

The vacuum pump (918) is then activated, and, if the vacuum pump (918) does not act as a valve when at rest, the valve (930) in the pump tube 917 is opened, to apply a low negative pressure to the wound.

The circulating fluid from the wound and the fluid reservoir (part of the integer (12)) passes through the cleansing unit (17). Materials deleterious to wound healing are removed and the cleansed fluid, still containing materials that are beneficial in promoting wound healing, is returned via the recirculation tube (13) to the wound bed.

The pressure feedback regulator (919) regulates the pressure at the wound and/or the tank (911).

If the amount of fluid in circulation becomes excessive, e.g. because the wound continues to exude heavily, the waste pump (914) may be started by the waste level feedback regulator (929) on the regulator receiving signals from the tank sensor with electrical line (930), to transfer fluid from the lower part of the tank (911) to the waste bag (915).

The recirculation of fluid may be continued as long as desired.

The vacuum pump (918) is then deactivated, and, if the vacuum pump (918) does not act as a valve when at rest, the valve (930) in the pump tube (917) is closed, and the bleed T-valve (16) is opened to air to relieve the low negative pressure in the tank (911) via the means for cleansing (17) and the outlet tube (917).

Switching between supply and recirculation is then reversed, by turning the T-valve (14) to admit fluid from the fluid reservoir to the wound dressing through the fluid supply tube (7) and inlet pipe (6).

The bleed valve (16) is left open, so that fresh fluid flushes the recirculating system. The running of the pump (918) may be continued until the apparatus is flushed, when it and the fluid recirculation is stopped.

Figure 15A:
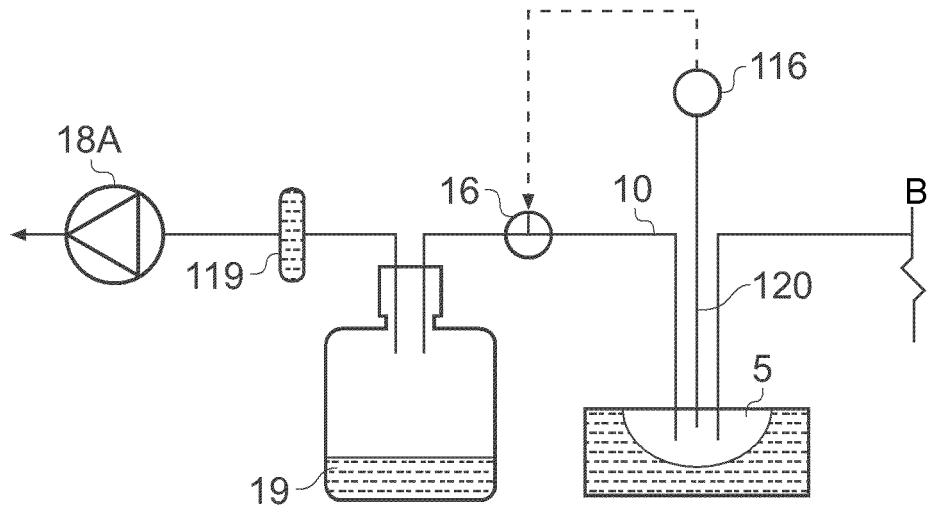
FIGS. 15a to c are variants of a two-pump system with essentially identical, and identically numbered, components as in FIG. 14, except that they have various means for varying the regulation of the positive or negative pressure applied to the wound.
Figure 15B:
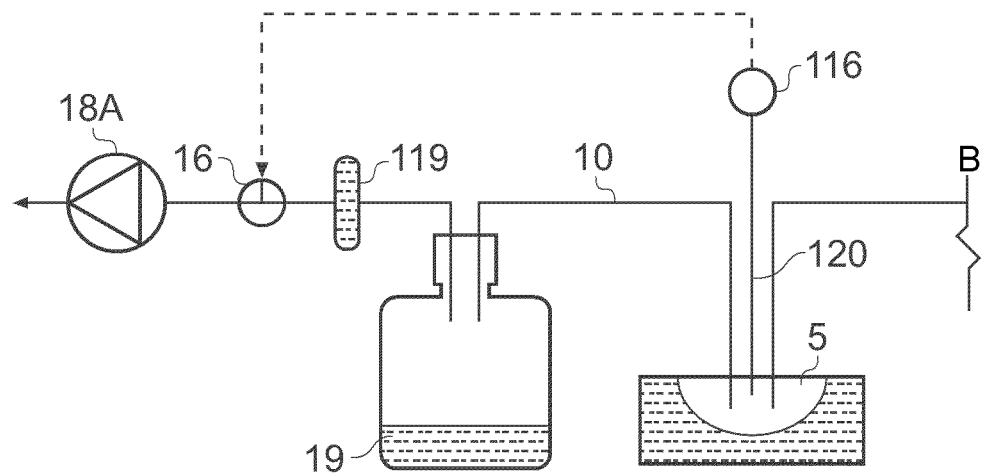
Figure 15C:
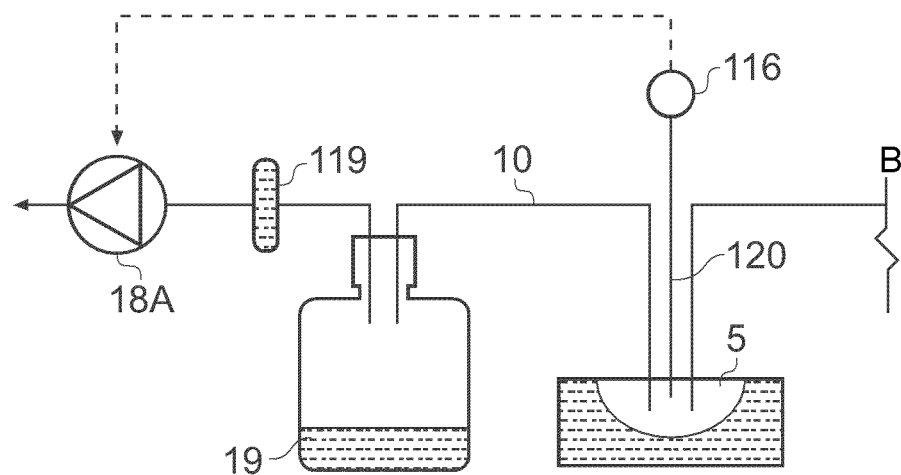
Figure 36A:
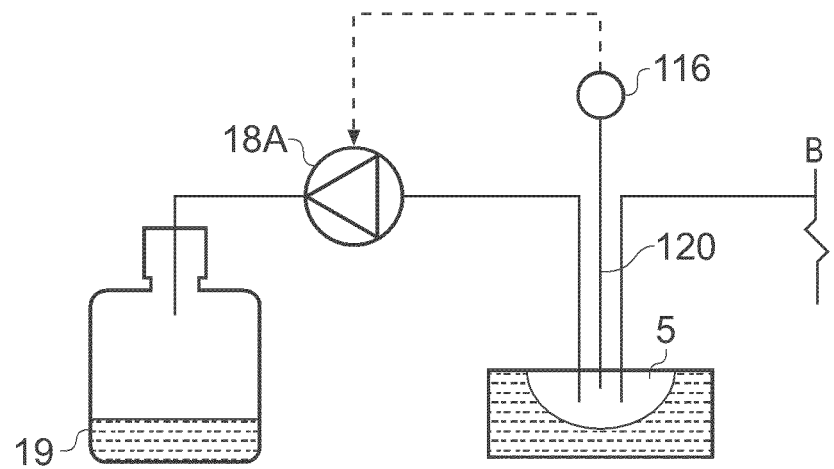
FIGS. 36a and b are variants of a two-pump system with essentially identical, and identically numbered, components as in FIGS. 14a-d. However, they have alternative means for handling the aspirate flow to the aspirate collection vessel under negative or positive pressure to the wound in simultaneous aspiration and irrigation of the wound, including in FIG. 30b a third device for moving fluid into a waste bag.

Referring to FIG. 36a, this shows another alternative layout of the essentially identical, and identically numbered, components in FIG. 15c downstream of point B in FIG. 14a, and alternative means for handling the aspirate flow to the aspirate collection vessel under negative or positive pressure to the wound.

The pressure monitor (116) is connected to a monitor offtake tube (120) and has a feedback connection to a variable-speed first device (18A), here a variable-speed pump, upstream of the aspirate collection vessel (19), and the filter (119) and the air aspiration tube (113) are omitted. This provides means for aspirate flow regulation and for holding the low negative pressure on the wound at a steady level. The operation of the apparatus is as described hereinbefore.

Figure 14B:
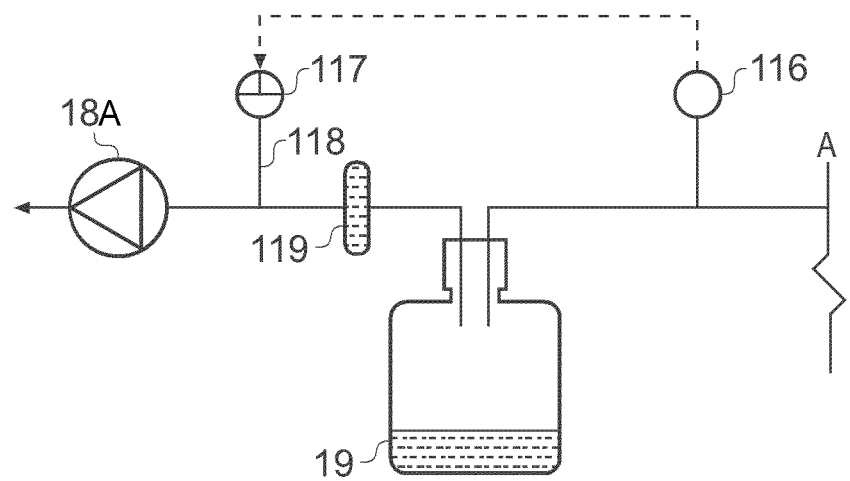
Figure 14C:
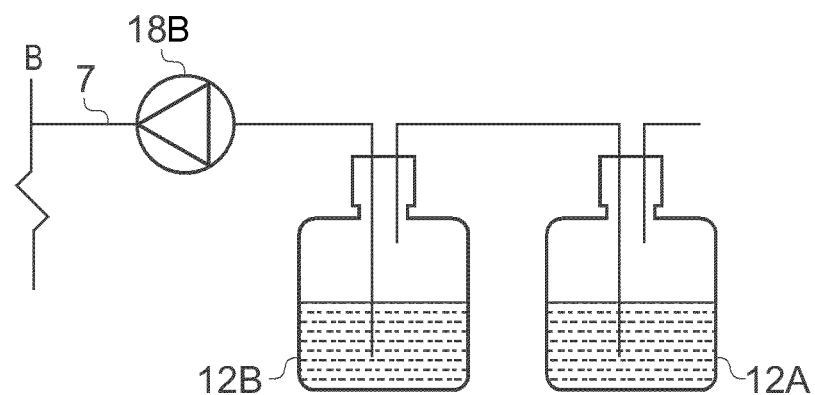
Figure 14D:
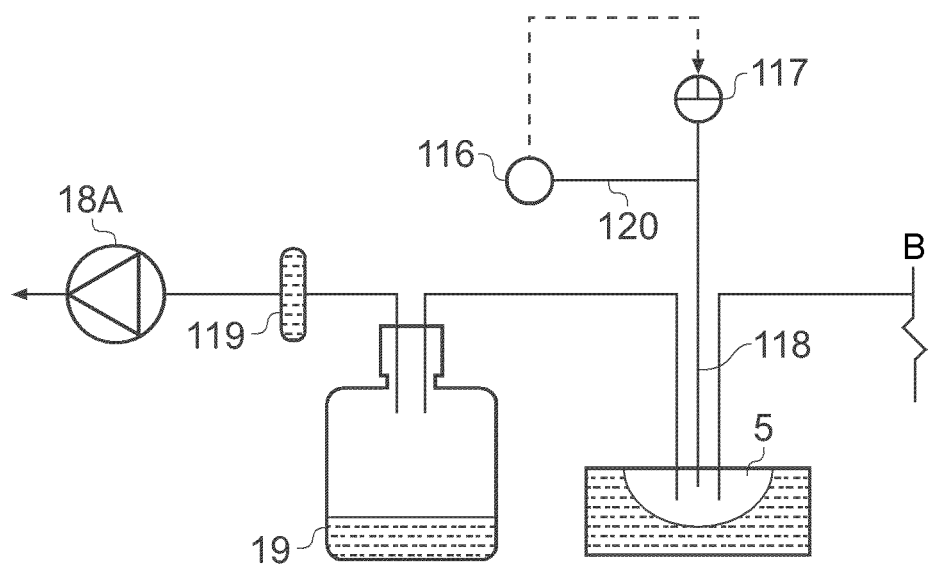
Figure 36B:
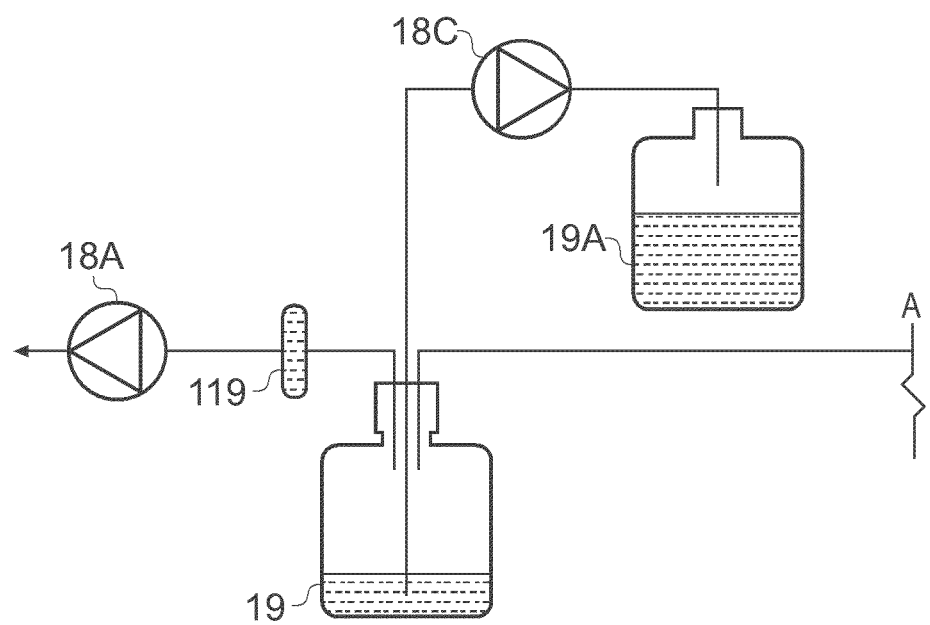

Referring to FIG. 36b, this shows another alternative layout of the essentially identical, and identically numbered, components in FIG. 14b downstream of point A in FIG. 14a, and alternative means for handling the aspirate flow to the aspirate collection vessel under negative or positive pressure to the wound. The pressure monitor (116) is omitted, as is the feedback connection to a variable-speed first device (18A), here a variable-speed pump, downstream of the aspirate collection vessel (19) and the filter (119). A third device (18C), here a fixed-speed pump, provides means for moving fluid from the aspirate collection vessel (19) into a waste bag (19A). The operation of the apparatus is as described hereinbefore.

Figure 37:
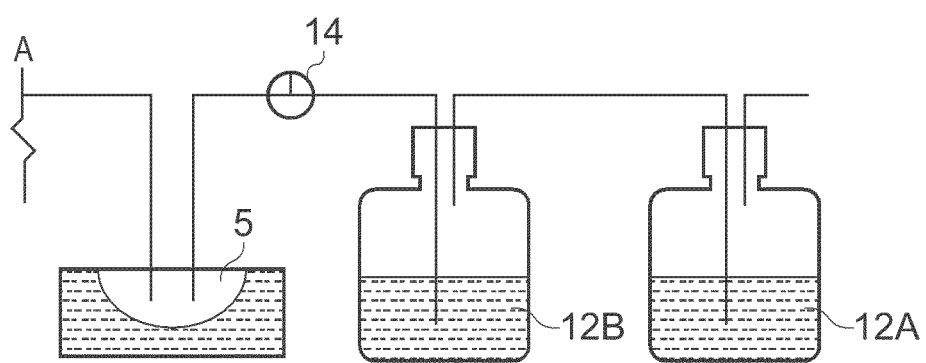
FIG. 37 is a single-pump system essentially with the omission from the apparatus of FIGS. 14a-d of the second device for moving irrigant fluid into the wound dressing.

Referring to FIG. 37, this shows an alternative layout of the essentially identical, and identically numbered, components in FIG. 14a upstream of point.

It is a single-pump system essentially with the omission from the apparatus of FIG. 14a of the second device for moving irrigant fluid into the wound dressing. The operation of the apparatus is as described hereinbefore.

EXAMPLES

The use of the apparatus of the present invention will now be described by way of example only in the following Examples:

Example 1

The removal by dialysis of materials deleterious to wound healing ($H_2O_2$) by an enzyme (catalase) retained in a moving second phase was combined with the addition of an active agent (PDGF) to the moving first phase.

An apparatus was constructed essentially as in FIG. 2, i.e. one in which the means for fluid cleansing is a two-phase system dialysis unit. In such an apparatus, an irrigant and/or wound exudate first phase from the wound recirculates through a first circuit and passes through the dialysis unit in contact across a selectively permeable dialysis membrane with a second fluid (dialysate) phase. The dialysis unit was operated with the two phases flowing counter-current to each other.

Hydrogen peroxide is produced in conditions of oxidative stress following reduced blood flow and or the inflammatory response to bacterial contamination of wounds. It may be removed by the appropriate antagonists and/or degraders, which include enzymic or other inhibitors, such as peroxide degraders, e.g. catalase.

The first circuit comprised a surrogate wound chamber (Minucells perfusion chamber) in which normal diploid human fibroblasts were cultured on 13 mm diameter (Thermanox polymer) cover slips retained in a two part support (Minnucells Minusheets). Tissues present in the healing wound that must survive and proliferate were represented by the cells within the chamber. Nutrient medium (DMEM with 5% FCS with 1% Buffer All) to simulate wound exudate was pumped from a reservoir into the lower aspect of the chamber where it bathed the fibroblasts and was removed from the upper aspect of the chamber and returned to the reservoir.

The first circuit also comprised upstream of the wound chamber, a luer-fitting hollow fibre tangential membrane dialysis unit (Spectrum® MicroKros® X14S-100-04N, 8 cm$^2$ surface area, 400 KD Mol. Wt. cut off,) through which a second cleansing circuit containing nutrient media with between 5,000 and 50,000 units (μmoles $H_2O_2$ degraded per min at pH7, 25° C.) per ml of catalase (in a circuit with a reservoir and total volume of between 5.0 ml and 20 ml) at a flow rate of between 0.5 ml min$^{-1}$ and 5.0 ml min$^{-1}$ could be passed in a counter current direction, The pumps for the two circuits were peristaltic pumps acting on silicone (or equivalent) elastic tubing. The internal diameter of the tubing was 1.0 mm. A total volume for the first circuit including the chamber and the reservoir at a number of values between 25 and 75 ml was used. The flow rates used were at a number of values between 0.5 ml min$^{-1}$ and 5.0 ml min$^{-1}$.

An experiment was conducted that simulated conditions not uncommon for healing wounds whereby the nutrient medium containing a material deleterious to wound healing, namely hydrogen peroxide, was circulated over the cells.

A solution of human recombinant Platelet Derived Growth Factor B was added to the reservoir of the first circuit so that the resulting concentration of PDGF-B lies at a number of values between 20 μg ml$^{-1}$ to 320 μg ml$^{-1}$, the fibroblasts survive and proliferate during.

A control experiment was also conducted where the solution of human recombinant Platelet Derived Growth Factor B is not added to the reservoir of the first circuit.

Results and Conclusions

In controls where either a) the passage of the nutrient flow through the cleansing membrane dialysis unit or b) the solution of human recombinant Platelet Derived Growth Factor B is not added to the reservoir of the first circuit heat, and the concentration of $H_2O_2$ lies between 5 and 20 mM survival and growth of the fibroblasts is inhibited.

However, when the nutrient medium flow in the first circuit is a) connected into the ends of the membrane dialysis unit through which a second cleansing circuit containing catalase (at the concentrations and flow rates noted above) is passing in a counter current direction, and b) the solution of human recombinant Platelet Derived Growth Factor B is added to the nutrient media bathing the cells, the fibroblasts survive and proliferate during a 24 hour period.

The combination of the cleansing dialysis unit and the active growth factor enhances the cell response necessary for wound healing.

Example 2

The removal by dialysis of materials deleterious to wound healing ($H_2O_2$) by an enzyme (catalase) retained in a static second phase was combined with the addition of an active agent (PDGF) to the moving first phase.

An apparatus of the present invention was constructed essentially as in FIG. 2, i.e. one in which the means for fluid cleansing is a two-phase system dialysis unit.

In such an apparatus, an irrigant and/or wound exudate first phase from the wound recirculates through a first circuit and passes in contact, across a selectively permeable dialysis membrane, with a static second fluid (dialysate) phase.

Hydrogen peroxide is produced in conditions of oxidative stress following reduced blood flow and or the inflammatory response to bacterial contamination of wounds. It may be removed by the appropriate antagonists and/or degraders, which include enzymic or other inhibitors, such as peroxide degraders, e.g. catalase.

The first circuit comprises a surrogate wound chamber (Minucells perfusion chamber) in which normal diploid human fibroblasts are cultured on 13 mm diameter (Thermanox polymer) cover slips retained in a two part support (Minnucells Minusheets). Tissues present in the healing wound that must survive and proliferate were represented by the cells within the chamber. Nutrient medium (DMEM with 5% FCS with 1% Buffer All) to simulate wound exudate was pumped from a reservoir into the lower aspect of the chamber where it bathed the fibroblasts and was removed from the upper aspect of the chamber and returned to the reservoir.

The first circuit also includes, upstream of the wound chamber, a static second phase dialysis unit, comprising a length of dialysis tubing (Pierce Snake skin 68100 CG 49358B, 10 KD cut off) placed within the first circuit reservoir in which a static second phase second cleansing circuit containing nutrient media with between 5,000 and 50,000 units (µmoles $H_2O_2$ degraded per min at pH7, 25° C.) per ml of catalase (in a circuit with a reservoir and total volume of between 5.0 ml and 20 ml) at a flow rate of between 0.5 ml min$^{-1}$ and 5.0 ml min$^{-1}$.

The pump was a peristaltic pump acting on silicone (or equivalent) elastic tubing. The internal diameter of the tubing was 1.0 mm. A total volume for the first circuit including the chamber and the reservoir at a number of values between 25 and 75 ml was used. The flow rates used were at a number of values between 0.5 ml min$^{-1}$ and 5.0 ml min$^{-1}$.

An experiment was conducted that simulated conditions not uncommon for healing wounds whereby the nutrient medium containing a material deleterious to wound healing, namely hydrogen peroxide, was circulated over the cells.

A solution of human recombinant Platelet Derived Growth Factor B was added to the reservoir of the first circuit so that the resulting concentration of PDGF-B lies at a number of values between 20 µg ml$^{-1}$ to 320 µg ml$^{-1}$, the fibroblasts survive and proliferate.

A control experiment was also conducted where the solution of human recombinant Platelet Derived Growth Factor B is not added to the reservoir of the first circuit.

Results and Conclusions

The following results were obtained for a first phase circuit comprising a wound chamber as above containing nutrient media (75 ml) with $H_2O_2$ (10 µM) pumped at a flow rate of 1.0 ml min$^{-1}$ in contact with a static second phase (15 ml) containing catalase (7,600 units ml$^{-1}$), where the wound chamber and media were held at 37° C. for 45 hours.

| Conditions | Mean level of cell activity* (n = 3) after 45 hours incubation. |
|---|---|
| Nutrient media only | 0.47 |
| Media with $H_2O_2$ only | 0.00 |
| $H_2O_2$ + catalase $2^{nd}$ phase dialysis unit | 0.64 |
| $H_2O_2$ + catalase $2^{nd}$ phase dialysis unit + 40 ng/ml PDGF | 0.56 |
| $H_2O_2$ + catalase $2^{nd}$ phase dialysis unit + 80 ng/ml PDGF | 0.86 |

*Cell activity measured with a WST (Tetrazolium based mitochondrial dehdrogenase activity assay).

In the controls where either a) the passage of the nutrient flow across the cleansing membrane dialysis unit or b) the solution of human recombinant Platelet Derived Growth Factor B is not added to the reservoir of the first circuit, and the concentration of $H_2O_2$ lies between 5 and 20 mM survival, growth of the fibroblasts is inhibited.

However, when the nutrient medium flow in the first circuit is a) passed over the membrane dialysis unit in which a second cleansing circuit containing catalase (at the concentrations and flow rates noted above) is present, and b) the solution of human recombinant Platelet Derived Growth Factor B (80 ng/ml) is added to the nutrient media bathing the cells, the fibroblasts survive and proliferate to a greater extent than in the control circuits.

The combination of the wound cleansing dialysis unit that removes and degrades $H_2O_2$ and the addition of the active PDGF growth factor at 80 ng/ml enhances the cell response necessary for wound healing.

Example 3

Adherent bacteria and debris was removed with a two-pump apparatus.

In this example, a culture medium sheet containing nutritional supplements with an adherent bacterial culture of *Staphylococcus aureus* on its top surface was laid in a cavity wound model to represent adherent bacteria and debris on a wound bed to be removed by the two-pump apparatus.

The dressing was essentially identical with that in FIG. 21, i.e. it comprised a circular backing layer and a lobed chamber in the form of a deeply indented disc much like a multiple Maltese cross or a stylised rose, defined by an upper impervious membrane and a lower porous film with apertures that deliver the irrigant fluid directly from the wound bed over an extended area.

The irrigant supplied to the wound dressing under a negative pressure on the wound bed contains a therapeutically active amount of an antibacterial agent, selected from chlorhexidine, povidone iodine, triclosan, metronidazole, cetrimide and chlorhexidine acetate.

A two-pump system was set up essentially as in FIG. 3, with an irrigant dispensing bottle—1000 ml Schott Duran, connected to a peristaltic pump (Masterflex) for irrigant delivery, and associated power supply and supply tube, a diaphragm vacuum pump (Schwarz) for aspiration, and associated power supply and offtake tube, connected to a vacuum vessel (aspirant collection jar)—Nalgene 150 ml polystyrene, each pump being connected to a dressing consisting of the following elements: 1) wound-contacting element, comprising a lobed bag with low porosity 'leaky' membrane wound contact layer on the lower surface, impermeable film on the top, and a foam spacer between the two layers to allow free flow of irrigant solution; 2) a space filling element, comprising a reticulated, open-cell foam (black reticulated foam, Foam Techniques) 30 mm thick, 60 mm diameter; 3) an occlusive adhesive coated polyurethane backing layer top film (Smith & Nephew Medical) with acrylic pressure sensitive adhesive; 4) two tubes passing under the occlusive top film, and sealed to prevent leakage of gas or liquid: i) one tube centrally penetrating the top film of the wound-contacting element to deliver irrigant into the chamber formed by this film and the porous element; ii) the other tube of approximately equal length to remove aspirant with the opening positioned just above the top film of the wound contacting element.

Preparation of Agar Culture Medium Sheet with Adherent *Staphylococcus Aureus* Culture.

An aqueous solution of agar culture medium was prepared by weighing agar culture medium containing nutritional supplements into a glass jar and making it up to the required weight with deionized water. The jar was placed in an oven (Heraeus), at a set temperature. After 60 minutes the jar was removed from the oven and shaken, to encourage mixing.

Petri dishes were partially filled with 10 g quantities of the culture medium and placed in a fridge (LEC, set temperature: 4° C.) to set for at least 1 hour.

Final thickness of the culture medium sheet was ~5 mm. Petri dishes containing the culture medium sheet were removed from the fridge at least 2 hours before use. The culture medium sheet in the Petri dishes was then inoculated with *Staphylococcus aureus*.

Each was then placed in an incubator at a set temperature. After the culture had covered more than 50% of the agar surface the dishes were removed from the incubator.

They were placed in a fridge, and removed from the fridge at least 2 hours before use.

Preparation of Test Equipment and Materials

Irrigant solution (deionized water containing a therapeutically effective amount of an antibacterial agent, selected from chlorhexidine, povidone iodine, triclosan, metronidazole, cetrimide and chlorhexidine acetate) and the Perspex wound model were pre-conditioned in an oven (Gallenkamp) at set temperature 37° C., for at least 4 hours before use.

For each test, a freshly prepared culture medium sheet with adherent *Staphylococcus aureus* culture was removed from a Petri dish and weighed. The Perspex wound model was then removed from the oven and the culture medium sheet with adherent *Staphylococcus aureus* culture placed at the bottom of the cavity. Application of the dressing to the wound model was as follows: 1) the wound contacting element was carefully placed over the culture medium sheet with adherent *Staphylococcus aureus* culture; 2) the foam filler was placed on top of this with the irrigant and aspirant tubes running centrally to the top of the cavity (the foam filler was slit to the center to facilitate this); 3) the side entry port, pre-threaded onto the tubes, was adhesively bonded to the upper surface of the wound model block using an acrylic pressure sensitive adhesive; 4) the top adhesive coated film was applied over all of the elements and pressed down to give a seal on all sides, and especially around the tube entry/exit point Application of the dressing to the wound model was the same for all tests performed. All tubing used was the same for each experiment (e.g. material, diameter, length).

Simultaneous Irrigation & Aspiration

For the experiment most of the apparatus (not including the pumps, power supply, and connecting tubing to and from the pumps) was placed in an oven (Gallenkamp, set temperature: 37° C.), on the same shelf.

Before starting the irrigation pump a vacuum was drawn on the system to check that the dressing and tube connections were substantially airtight.

The pumping system was controlled to give a pressure at the vacuum vessel of approximately −75 mmHg before opening the system up to include the dressing). Once system integrity had been confirmed, the irrigation pump was started (nominal flow rate: 50 ml/hr), i.e. both pumps running together. Timing of the experiment was started when the advancing water front within the irrigant tube was observed to have reached the top of the dressing.

After 60 minutes, the irrigation pump was stopped, shortly followed by the vacuum (aspiration) pump. Aspirant liquid collected in the vacuum jar was decanted into a glass jar. The vacuum jar was rinsed with ~100 ml of deionized water and this added to the same glass jar. The aspirant solution was then assayed for the *Staphylococcus aureus* quantity present.

Sequential Irrigation & Aspiration

The experimental set up was as for the simultaneous irrigation/aspiration experiment. Before starting the experiment a vacuum was pulled on the system to check that the dressing and tube connections were substantially airtight. The pumping system was controlled to give a pressure at the vacuum vessel of approximately −75 mmHg before opening the system up to include the dressing. Once system integrity had been confirmed, the irrigation pump was started (nominal rate: 186 ml/hr) and run until the advancing water front in the irrigant tube was observed to have reached the top of the dressing.

The pump was temporarily stopped at this point whilst the vacuum line was sealed (using a tube clamp) and the vacuum pump stopped.

Timing of the experiment was from the point the irrigation pump was restarted. The pump was run until 50 ml of irrigant has entered the wound model (just over 16 minutes at the rate of 186 ml/hr). At this point the irrigant pump was stopped.

It was observed that during the filling phase of sequential filling and flushing, air trapped in the model wound cavity caused the top film of the dressing to inflate substantially, to a point approaching failure.

After a further ~44 minutes (60 minutes from the start of the experiment) the vacuum pump was started and the tube clamp on the aspirant line removed. The wound model was aspirated for 5 minutes. Towards the end of this period a small leak was introduced into the top film of the dressing to maximize the amount of fluid drawn from the wound model (it is observed that as the pressure differential between the wound model cavity and the vacuum jar reduced to zero, the flow of aspirant also tended to slow. Introducing a small leak re-established the pressure differential and the flow of aspirant out of the cavity).

Aspirant liquid collected in the vacuum jar was decanted into a glass jar. The vacuum jar was rinsed with ~100 ml of deionized water and this added to the same glass jar. The aspirant solution was then assayed for the *Staphylococcus aureus* quantity present.

Results and Conclusions

Simultaneously irrigating and aspirating the wound model removes or kills more of the adherent *Staphylococcus aureus* on the culture medium sheet placed at the base of the wound model cavity than sequentially filling and emptying the cavity, even though the amount of liquid entering the wound and the duration of the experiment are the same in both cases. Simultaneously irrigating and aspirating also removes more fluid from the model wound.

Example 4

The combination of simultaneous fluid flow (irrigation) with aspiration (under reduced pressure) and actives (PDGF-bb) on wound bed fibroblasts was compared with the exposure of wound bed fibroblasts to repeated fill-empty cycles of fluid flow and aspiration.

Figure 38:
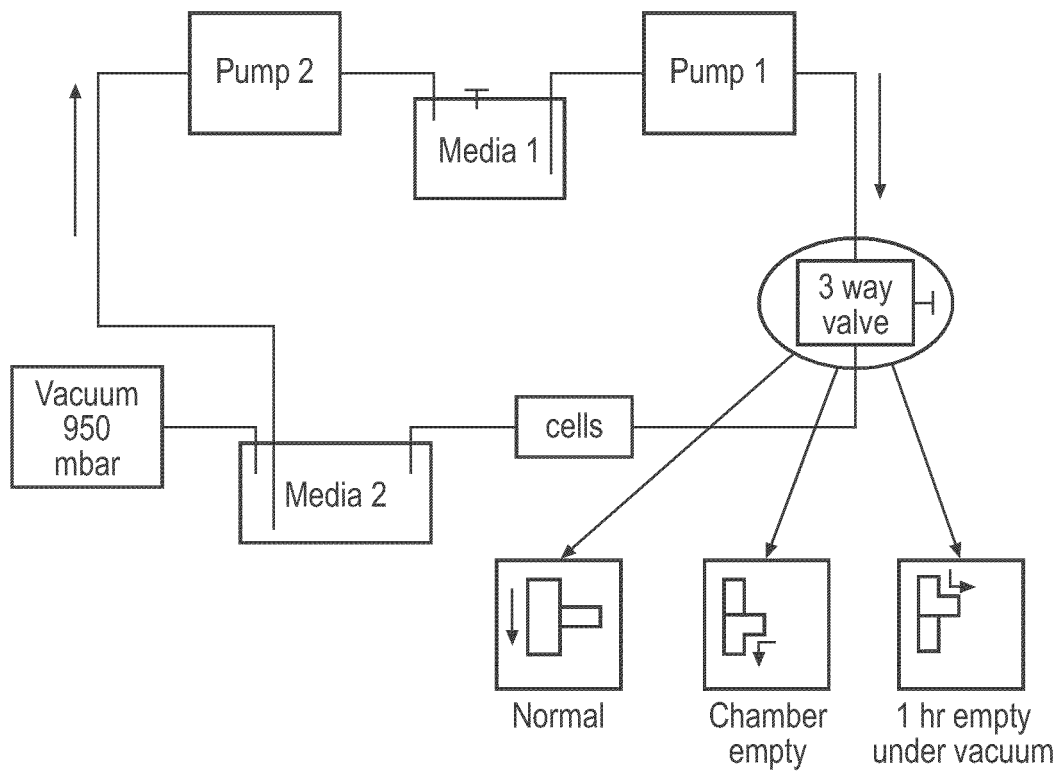
FIG. 38 shows a schematic representation of a simultaneous irrigate/aspirate (SIA) and sequential irrigate/aspirate (SEQ) flow system.

An apparatus of the present invention was constructed essentially as in FIG. 38 which is an apparatus where an irrigant or fluid of some nature is delivered continually to the wound bed and the resultant wound exudate/fluid mixture is at the same time continually aspirated from the wound.

Alternative systems are known where the wound is subjected to repeated iteration of a cycle of fluid delivery followed by a period of aspiration under reduced pressure.

The apparatus comprised a surrogate wound chamber (Minucells perfusion chamber) in which normal diploid human fibroblasts were cultured on 13 mm diameter (Thermanox polymer) cover slips retained in a two part support (Minnucells Minusheets). Tissues present in the healing wound that must survive and proliferate were represented by the cells within the chamber. Nutrient medium (DMEM with 10% FCS with 1% Buffer All) to simulate an irrigant fluid/wound exudate mixture, was pumped from a reservoir into the lower aspect of the chamber where it bathed the fibroblasts and was removed from the upper aspect of the chamber and returned to a second reservoir. The wound chamber was maintained at less than atmospheric pressure by means of a Vacuum pump in line with the circuit.

The pumps for the circuit were peristaltic pumps acting on silicone (or equivalent) elastic tubing. The circuit was exposed to a vacuum of no more than 10% atmospheric pressure, 950 mbar and atmospheric pressure varied up to a maximum value of 1044 mbar. The internal diameter of the tubing was 1.0 mm. A total volume for the circuit including the chamber and the reservoir of between 100 and 220 ml was used. The flow rates used were at a number of values between 0.1 ml min$^{-1}$ and 2.0 ml$^{-1}$ min$^{-1}$.

An experiment was conducted that simulated conditions that are not uncommon for healing wounds whereby a fluid was delivered to the wound bed and the application of a vacuum was used to remove the mixture of fluid and exudate to a waste reservoir. An air bleed fluid control valve was additionally positioned in the circuit so that on opening the air bleed occurred for a time and closed the fluid flow, the simulated irrigant fluid/wound exudate mixture was evacuated from the chamber and the chamber left empty and the fibroblasts were maintained under a negative pressure relative to the atmosphere. This represents an empty/fill system, 6 cycles of empty/fill were performed with each fill or empty phase lasting 1 hour.

An experiment was conducted using the following 2 scenarios:

Apparatus was constructed essentially as in FIG. 38 but where a) continuous flow simultaneous aspirate irrigate system with b) material beneficial to wound healing (PDGF-bb) was present in the nutrient flow bathing the cells.

Apparatus was also constructed essentially as in FIG. 38 but a) it was operated as an empty/fill system with 6× cycles of 1 hour empty/1 hour fill over a total of 25 hours with b) the material beneficial to wound healing (PDGF-bb) was present, in the nutrient flow bathing the cells.

Results and Conclusions

The following results were obtained for a circuit comprising a wound chamber as above containing a total volume of nutrient media (104 ml) pumped at a flow rate of 0.2 ml min$^{-1}$, and where vacuum was set at 950 mbar and where atmospheric pressure was varied up to a maximum value of 1044 mbar. The wound chamber and media were held at 37° C. for 25 hours. In one set of wound chambers continuous flow was maintained. In a second set of chambers 6 cycles of empty/fill were performed with each fill or empty phase lasting 1 hour.

In controls a) operated as empty/fill with 6 cycles of 1 hour empty/1 hour fill, and b) where PDGF-bb is present, the survival and growth of fibroblasts is inhibited compared to the continuous flow systems.

Where flow circuits consists of a) continuous flow (SIA) and b) PDGF-bb is present the survival and growth of fibroblasts is enhanced to a greater level than empty/fill plus PDGF-bb.

| Conditions | Mean of cell activity* after 25 hours. |
|---|---|
| Continuous flow (SIA) plus active (PDGF-bb) | 0.34 |
| Fill empty 6 cycles plus active (PDGF-bb) | 0.22 |

*Cell activity measured with a WST (Tetrazolium based mitochondrial dehdrogenase activity assay).

The combination of actives (PDGF-bb) and continuous fluid flow at 0.2 ml min$^{-1}$ with waste fluid removal under a vacuum of no more than 10% atmospheric pressure, enhances the cell response necessary for wound healing more than the fill empty system (+PDGF-bb).

Example 5

Using simultaneous irrigate/aspirate (SIA) and sequential irrigate/aspirate (SEQ), the effect of cells as a source of 'actives' on fibroblast proliferation was determined.

Method

Cells

Human dermal fibroblasts (HS8/BS04) grown at 37° C./5% CO$_2$, in T175 flasks containing 35 ml DMEM/10% FCS media were washed in PBS and lifted using 1× trypsin/EDTA (37° C. for 5 min). Trypsin inhibition was achieved by adding 10 ml DMEM/10% FCS media and the cells pelleted by centrifugation (Hereus Megafuge 1.0R; 1000 rpm for 5 min). The media was discarded and cells re-suspended in 10 ml DMEM/10% FCS. Cells were counted using haemocytometer (SOP/CB/007) and diluted in DMEM/10% FCS to obtain 100,000 cells per ml.

Cells (100 µl of diluted stock) were transferred to 13 mm Thermanox tissue culture coated cover slips (Fisher, cat. no. 174950, lot no. 591430) in a 24 well plate and incubated at 37° C. in 5% CO$_2$ to allow for cell adherence. After 1 h, 1 ml DMEM/10% FCS media was added per well and the cells incubated for approximately 5 hours in the above conditions. Cells were serum starved overnight by removing the DMEM/10% FCS and washing the coverslips with 2×1 ml PBS prior to the addition of 1 ml DMEM/0% FCS.

Following overnight incubation, cells were assessed visually for cell adherence under the microscope and those with good adherence were inserted into cover slip holders for assembly in the Minucell chamber.

Media

Cells were grown in DMEM media (Sigma, cat. no. D6429) supplemented with 5% foetal calf serum; 1-glutamine, non-essential amino acids and penicillin/streptomycin. Media used in the experimental systems was buffered with 1% (v/v) Buffer-All media (Sigma, cat. no. B8405, lot. no. 51k2311) to ensure stable pH of the media.

Minucell Flow Systems

Media (50 ml) was transferred to each bottle prior to the autoclaved systems being assembled. The Minucell chambers were filled with 4 ml media prior to coverslips being inserted. The systems were set-up as shown in FIG. 38, set to run at 0.2 ml/min; hot plates, set to 45° C.; Discofix 3-way valves; vacuum pump, (Ilmvac VCZ 310), set to 950 mbar).

SEQ Systems

Media was pumped through the systems at 0.2 ml/min continuously when the chambers were full. The Minucell chambers were emptied by disconnecting the tubing from the pump and switching the 3-way valve to allow air through an attached 0.22 µm filter. When fully emptied, the 3-way valve was switched to close the system between the valve and the pump and so allowing the formation of a vacuum in the system. Elevation of the 3-way valve ensured media did not pass through the 0.22 µm filter by gravity flow. After 1 h, the 3-way valve was switched back to the starting position to allow the Minucell chamber to fill and the tube reconnected to the pump. The SEQ systems were treated as per the following table.

Fill/Empty Regime for SEQ Systems:

| Time (h)   | 0 | 1 | 2 | 3 | 4 | 5 | 6 | 7 | 8 | 20 | 21 | 22 | 23 | 24 |
|---|---|---|---|---|---|---|---|---|---|---|---|---|---|---|
| Empty/fill | F | E | F | E | F | E | F | E | F | E | F | E | W | A |

F = full chamber/flowing; E = empty chamber/under vacuum; W = remove coverslips for WST assay; A = read WST assay result.

SIA Systems

Continuous irrigate aspirate systems were run for 24 h with media irrigating the cells and being aspirated under vacuum set to 950 mbar. The atmospheric pressure varied daily, up to a maximum value of 1048 mbar, therefore the difference in pressure between the systems and the atmosphere was always under 10%.

Cells as Actives Component

The 'cells as actives' component of the flow cell system was provided by Dermagraft (a fibroblast seeded Vicryl mesh). Dermagraft stored at −70° C. was defrosted by placing in a 37° C. water-bath for 1 min and washed ×3 with 50 ml 0.9% v/v NaCl. The Dermagraft was cut into 24×1.1 cm² squares using a sterile clicker-press and placed into DMEM/5% FCS. For the flow-cell experiments, a number of Dermagraft squares were placed in Media 1 bottle (FIG. 1) immediately prior to the start of the experiment. The presence of live cells in the Dermagraft squares was determined by WST assay when the experiment was terminated.

WST Assay

A WST assay to measure cell mitochondrial activity was performed on the coverslips. WST reagent (Roche, cat. no. 1 644 807, lot no. 11264000) was diluted to 10% v/v in DMEM/10% FCS. The coverslips (n=6) were removed from each Minucell chamber and washed in 1 ml PBS. PBS was removed and 200 µl WST/DMEM media added. The coverslips were then incubated at 37° C. for 45 min before transferring 150 µl to a 96 well plate. The absorbance at 450 nm with reference at 655 nm was determined using Ascent Multiskan Microtitre plate reader.

Figure 39:
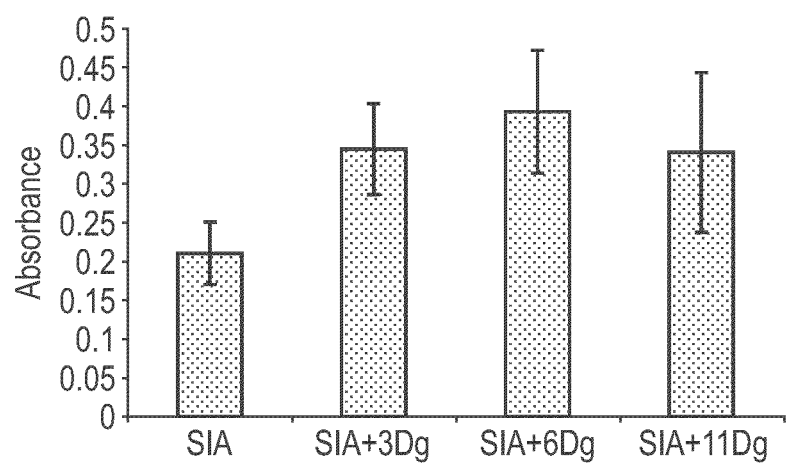
FIG. 39 shows increased WST activity of fibroblasts and thus increased proliferation of cells in a SIA system with actives from cells being added.

The mitochondrial activity of cells grown in SIA and SEQ systems, with or without 'cells as actives' component was determined using the WST assay. The optimal number of Dermagraft squares required was first assessed in a SIA flow cell system. Addition of Dermagraft squares to the media had a beneficial effect, increasing the proliferation rate of seeded fibroblasts (FIG. 39). There was a slight benefit to increasing the number of Dermagraft squares from 3 to 6, although increasing the amount of Dermagraft to 11 squares did not further increase the rate of proliferation. Therefore, for the flow cell experiments, 6 Dermagraft squares were placed in the relevant media bottles. The experiments to show the optimal number of Dermagraft squares also showed that the addition of cells as a source of actives, to the SIA systems, resulted in an increased rate of proliferation (FIG. 39).

Results and Conclusions

Figure 40:
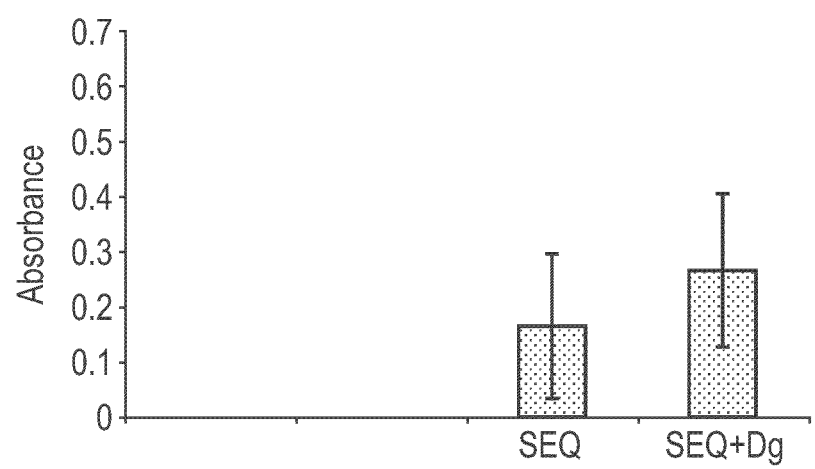
FIG. 40 shows a summary of WST activity of fibroblasts in SEQ systems for 24 h with or with "cells as actives" component (n=3).

Treatment of fibroblasts by the addition of 'cells acting as a source of actives' to the media, increased the rate of proliferation in SIA and the SEQ systems after 24 hours (FIGS. 39 & 40).

This beneficial effect was observed in both SAI and the SEQ flow systems.

Example 6

Method

Cells

Human dermal fibroblasts (HS8/BS04) grown at 37° C./5% $CO_2$, in T175 flasks containing 35 ml DMEM/10% FCS media were washed in PBS and lifted using 1× trypsin/EDTA (37° C. for 5 min). Trypsin inhibition was achieved by adding 10 ml DMEM/10% FCS media and the cells were pelleted by centrifugation (Hereus Megafuge 1.0R; 1000 rpm for 5 min). The media was discarded and cells resuspended in 10 ml DMEM/10% FCS. Cells were counted using a N haemocytometer (SOP/CB/007) and diluted in DMEM/10% FCS to obtain 100,000 cells per ml.

Cells (100 µl of diluted stock) were transferred to each 13 mm Thermanox tissue culture coated cover slip (cat. 174950, lot 591430) in a 24 well plate and incubated for 1 hr at 37° C./5% $CO_2$ to allow cell adherence. After 1 h, 1 ml DMEM/10% FCS media was added per well. After 6 h, the media was removed, cells washed with 2×1 ml PBS and 1 ml DMEM/0% FCS added per well and the cells incubated overnight in the above conditions.

Following overnight incubation, cells were assessed visually for growth under the microscope and those with growth were inserted into cover slip holders (Vertriebs-Gmbh, cat no. 1300) for assembly in the Minucell chamber (Vertriebs-Gmbh, Cat no. 1301).

Media

Cells were grown in DMEM media (Sigma, no. D6429) supplemented with 10% foetal calf serum; 1-glutamine, non-essential amino acids and penicillin/streptomycin. Media used in the experimental systems was supplemented with 5% (v/v) foetal calf serum and buffered with 1% (v/v) Buffer-All media (Sigma, lot 51k2311) to ensure stable pH of the media.

Minucell Flow Systems

Figure 32:
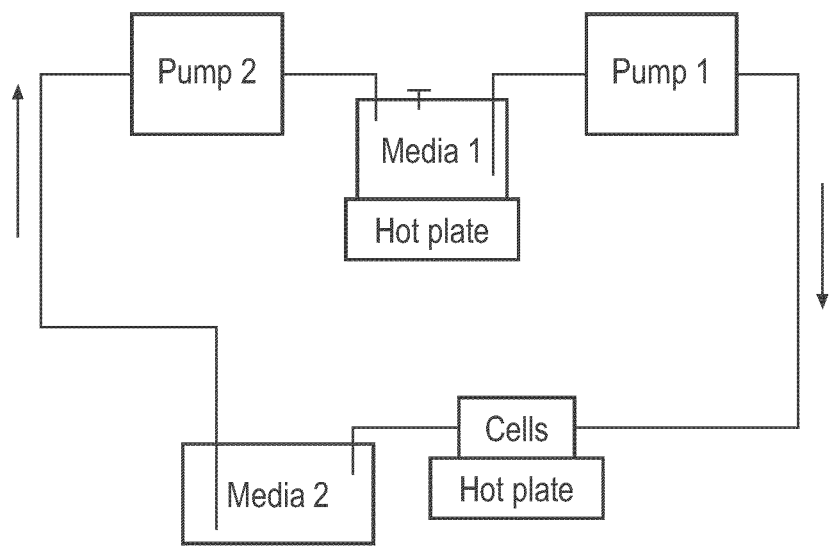
FIG. 32 shows a schematic representation exudialysis flow system according to one embodiment of the present invention.

Systems (5) were made up as per FIG. 32.

|  | Bottle 1 | Bottle 2 |
|---|---|---|
| System 1 | Media | Media |
| System 2 | Media | Media and 6 Dermagraft squares |
| System 3 | Media + catalase | Media |
| System 4 | Media + $H_2O_2$ | Media + Dermagraft |
| System 5 | Media + catalase + $H_2O_2$ | Media + Dermagraft |

Equipment used in the flow system was Ismatec IPC high precision peristaltic pumps with Ismatec pump tubing 1.02 mm ID and high strength silicon tubing (HS-0152-009, Cole Palmer Instruments) and hot plates (asset number 6531 and 6532).

Catalase

Snakeskin pleated dialysis tube (10 kDa MWCO; Pierce, no. 68100, lot EB9446) containing 15 ml catalase (or 86200 units; Sigma, C3155, lot 014K7029). The dialysis tubing was placed in Media 1 bottle.

$H_2O_2$

Hydrogen peroxide (Sigma, lot 074K3641; stock 8.8M, 30% soln) (250 μl) added to 21.75 ml DMEM/5% FCS media. 5.1 ml of the media added to 39.9 ml DMEM/5% FCS media and 5 ml of this was added to bottle 1 of the relevant systems giving a final concentration of 1.1 mM.

Hydrogen peroxide ($H_2O_2$) was used to mimic the chronic wound element, as it is a reactive oxygen species that causes oxidative stress to cells. The enzyme catalase is a natural antioxidant that degrades $H_2O_2$ into water and oxygen protecting cells against oxidative damage to proteins, lipids and nucleic acids. So, it was placed in dialysis tubing to mimic exudialysis. A source of cells as a source of actives was provided by using Vicryl mesh seeded with live fibroblast cells [Dermagraft]. The experiment ran for a total of 48 hours. A WST assay was used to measure fibroblast activity after 48 hours.

Cells as a Source of Actives

The 'cells as a source of actives' was fibroblasts seeded on a Vicryl mesh (Dermagraft, Smith and Nephew). Dermagraft was defrosted in a water bath at 37° C. for 1 minute and the cryoprotectant removed. The Dermagraft was washed with 3×50 ml 0.9% saline and cut into 1.1 cm squares using the clickerpress. 6 squares of Dermagraft were placed in bottle 2 of the systems described above. The final volume of media was made up to 50 ml in bottle 1 and bottle 2.

WST Assay

A WST assay to measure the cells mitochondrial activity was performed on 6 coverslips from each system. WST reagent (Roche, lot 102452000) was diluted to 10% v/v in DMEM/10% FCS/buffer all media. The coverslips were removed from the Minucell chamber and washed in 1 ml PBS. PBS was removed and 200 μl WST/DMEM media added. The coverslips were then incubated at 37° C. for 45 min before transferring 150 μl of reagent to a 96 well plate. The absorbance at 450 nm with reference at 655 nm was determined using Ascent Multiskan Microtitre plate reader.

The mitochondrial activity of cells grown in exudialysis systems, with or without 'cells as actives' component was determined using the WST assay. The WST activity of individual experiments is shown in FIGS. 33 and 34, with the average WST activity represented by the bar and standard deviation by the error bars.

Figure 33:
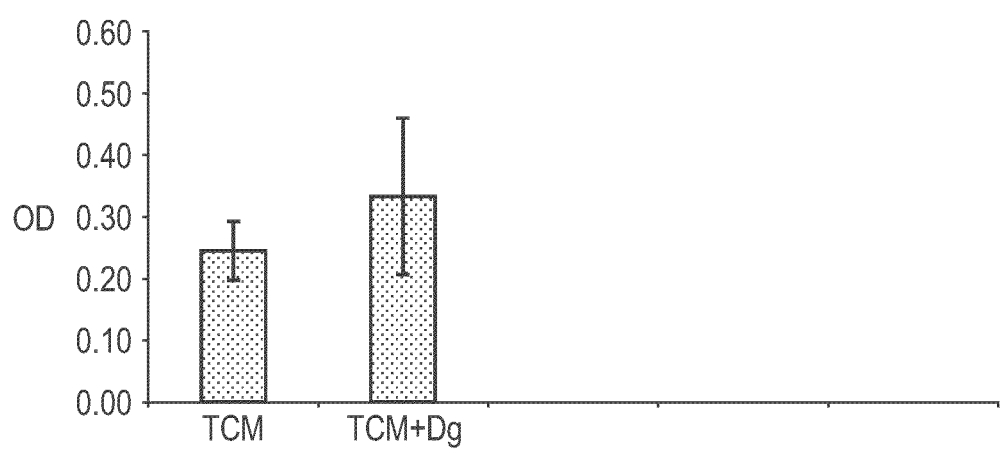
FIG. 33 shows WST activity of fibroblasts with the addition of Dermagraft (the source of actives from live cells) in comparison to a media only control (TCM).

From the data in FIG. 33 it is possible to see that the addition of Dermagraft (Dg) (the source of actives from live cells) resulted in an increased fibroblast activity, as measured by the WST assay.

Fibroblast activity within the Dermagraft squares was shown by assaying a number of Dermagraft squares from the media at the end of the experimental incubation period. Dermagraft activity was in the range 0.17 to 0.95 and was therefore alive.

Figure 34:
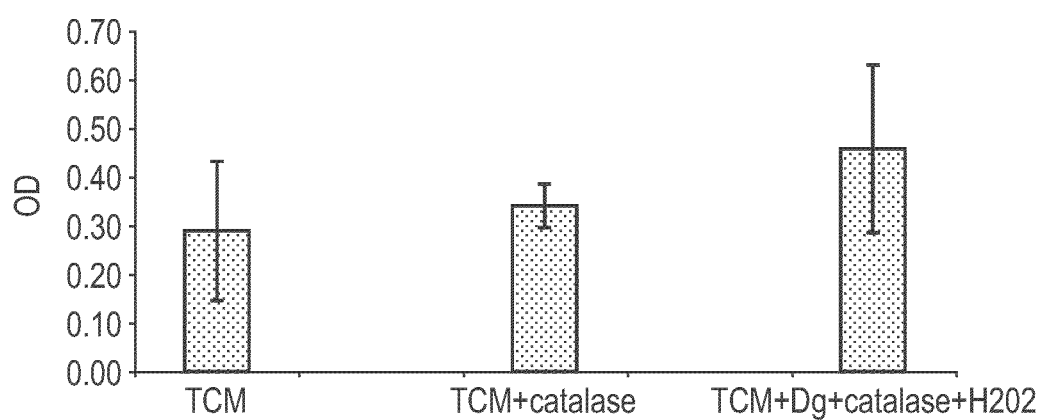
FIG. 34 shows WST activity of fibroblasts (i) with an exudialysis system TCM+catalase, (ii) in a media with the addition of Dermagraft (the source of actives from live cells) Dg and hydrogen peroxide $H_2O_2$, (iii) in a media with the addition of Dermagraft (the source of actives from live cells) Dg, hydrogen peroxide ($H_2O_2$) and with an exudialysis system (+catalase). It has a single-phase system means for fluid cleansing in the form of an ultrafiltration unit.

From the data in FIG. 34 it is possible to see that with the addition of exudialysis (+catalase) resulted in an increased fibroblast activity over the control of media only (TCM).

This graph (FIG. 34) also showed that the presence of $H_2O_2$ Hydrogen Peroxide even with Dermagraft (Dg) had no fibroblast activity. Thus in the absence of a removal system hydrogen peroxide, a source of toxic reactive oxygen species, kills the fibroblasts seeded on the coverslip and in the Dermagraft.

In contrast, the data shows for, the actives from live cells (Dg) with Exudialysis (+catalase) even with Hydrogen Peroxide ($H_2O_2$) a significant increase in fibroblast activity, as measured by the WST assay over the media only control, the hydrogen peroxide control and media and exudialysis result.

This increase was also greater than with media and actives from live cells (FIG. 33).

Results and Conclusions

It is possible to see an increase fibroblast growth activity when the cells are in the flow system in conjunction with the live cells providing a source of actives along with the exudialysis system which removes the 'chrome wound element' from the media.

Example 7

The benefit of using cells as a cleanser in the Exudialysis systems can be demonstrated.

Method

Cells

Human dermal fibroblasts (HS8/BS04) would be prepared for growth on Thermanox coverslips.

Media

Cells to be grown in DMEM media (Sigma, no. D6429) supplemented with 10% foetal calf serum; 1-glutamine, non-essential amino acids and penicillin/streptomycin (various lot numbers). Media to be used in the experimental systems is supplemented with 5% (v/v) foetal calf serum and buffered with 1% (v/v) Buffer-All media (Sigma) to ensure stable pH of the media. Alternatively, cells will be grown in Eagle MEM media supplemented with 2 mM glutamate, 1.5 g/L sodium bicarbonate, 0.1 mM NEAA and 1 mM sodium pyruvate. The Eagle MEM media is the recommended media type for hepatocyte cell line.

Cells as Cleanser Aspect

Hepatocyte cell line (for example HepG2/C3A cell line; ATCC, ATCC-CRL-10741) would be used as the cells to remove factors deleterious to wound healing (e.g. hydrogen peroxide) from the media. The cell line would be grown either on a synthetic matrix (e.g. nylon mesh) or possibly a non-synthetic matrix and placed within the exudialysis system either enclosed in a dialysis type membrane or free floating in the media bottle.

Exudialysis System

A number of systems would be made up to provide the relevant controls and test conditions. These would include:

|  | Bottle 1 | Bottle 2 |
|---|---|---|
| System 1 | Media | Media |
| System 2 | Media | Media and hepatocytes |
| System 3 | Media + catalase | Media |
| System 4 | Media + $H_2O_2$ | Media + hepatocytes |
| System 5 | Media + $H_2O_2$ | Media |

Equipment used in the flow system would include Ismatec IPC high precision peristaltic pumps with Ismatec pump tubing 1.02 mm ID and high strength silicon tubing (HS-0152-009, Cole Palmer Instruments) and hot plates.

$H_2O_2$

Hydrogen peroxide (Sigma, lot 074K3641; stock 8.8M, 30% soln) (250 μl) added to 21.75 ml DMEM/5% FCS media (or Eagle MEM media). 5.1 ml of the media added to 39.9 ml DMEM/5% FCS media and 5 ml of this was added to bottle 1 of the relevant systems giving a final concentration of 1.1 mM.

Catalase

Catalase is to be used as a positive control. Snakeskin pleated dialysis tube (10 kDa MWCO; Pierce, no. 68100, lot EB9446) containing 15 ml catalase (or 86200 units; Sigma, C3155, lot 014K7029). The dialysis tubing was placed in Media bottle.

WST Assay

A WST assay would be used to measure the cells mitochondrial activity was on 6 coverslips from each system. WST reagent (Roche) is diluted to 10% v/v in experimental/Buffer All media. The coverslips are removed from the Minucell chamber and washed in 1 ml PBS. PBS was removed and 200 μl WST/media added. The coverslips would then incubated at 37° C. for 45 min before transferring 150 μl of reagent to a 96 well plate. The absorbance at 450 nm with reference at 655 nm is determined using Ascent Multiskan Microtitre plate reader.

Figure 35:
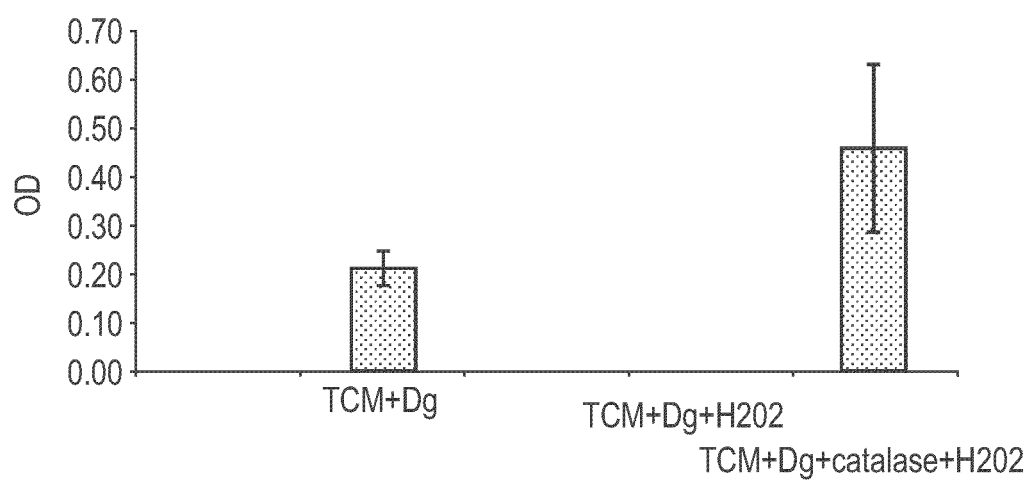
FIG. 35 shows average WST activity of fibroblasts on (a) control (TCM+Dg) of media and cells, (b) media, cell and Hydrogen peroxide (TCM+Dg+$H_2O_2$); and (c) media, cells, Hydrogen peroxide and exudialysis (TCM+Dg+catalase+ $H_2O_2$). It has a single-phase system means for fluid cleansing, in the form of a container, e.g. a canister, cartridge or cassette, with a chamber or compartment that contains a cell or tissue component, through which the wound exudate or a mixture with irrigant passes.

It would be expected that hepatocyte cells would convert and detoxify hydrogen peroxide to oxygen and water through the action of catalase, which is reported to be a protein component of hepatocytes. Through the detoxification action of hepatocytes, the fibroblasts present in the wound bed will survive and proliferate to a greater extent than to those exposed to hydrogen peroxide alone. Previous experiments have shown the presence of hydrogen peroxide kills the seeded fibroblasts (FIG. 35).

Results and Conclusions

Hydrogen peroxide, at a sufficient concentration is toxic to fibroblast cells.

A major role of hepatocytes is to detoxify biological fluids through enzymatic (e.g. catalase) mechanisms.

By placing hepatocyte cells within a flow system it would be expected that the hepatocytes would detoxify the media and remove hydrogen peroxide to a sufficient level to enable the fibroblasts present to survive and proliferate.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure. Many of the embodiments described above include similar components, and as such, these similar components can be interchanged in different embodiments.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. An apparatus for aspirating, irrigating and/or cleansing wounds, comprising:
   a conformable wound dressing having a backing layer configured to form a relatively fluid-tight seal or closure over a wound;
   a physiologically active agent source configured to connect by a fluid supply tube to the wound dressing, wherein the fluid supply tube is configured to deliver a physiologically active agent comprising oxygen from the physiologically active agent source to the wound;
   a negative pressure source configured to apply negative pressure to an interior of the wound dressing and to the wound; and
   wherein the physiologically active agent is configured to be supplied to the wound dressing from the physiologically active agent source via the fluid supply tube while fluid is simultaneously aspirated by the negative pressure source and desired negative pressure is applied to the wound.

2. The apparatus of claim 1, further comprising a wound contact layer.

3. The apparatus of claim 1, wherein the wound contact layer comprises a biodegradable material.

4. The apparatus of claim 3, wherein the biodegradable material comprises a cellulose derivative.

5. The apparatus of claim 1, wherein the physiologically active agent source comprises a reservoir.

6. The apparatus of claim 1, further comprising a controller.

7. The apparatus of claim 6, wherein the controller is configured to control delivery of negative pressure.

8. The apparatus of claim 6, wherein the controller is configured to control delivery of the physiologically active agent.

9. The apparatus of claim 7, wherein negative pressure is delivered continuously.

10. The apparatus of claim 7, wherein negative pressure is delivered intermittently.

11. The apparatus of claim 6, wherein the controller is configured to switch between a first setting where a physiologically active agent is delivered to the wound and a second setting where negative pressure is delivered to the wound.

12. The apparatus of claim 8, wherein the physiologically active agent is delivered in a plurality of supply cycles.

13. The apparatus of claim 6, wherein the controller is configured to control delivery of negative pressure and delivery of the physiologically active agent.

\* \* \* \* \*

UNITED STATES PATENT AND TRADEMARK OFFICE
CERTIFICATE OF CORRECTION

PATENT NO. : 11,298,453 B2  
APPLICATION NO. : 16/142411  
DATED : April 12, 2022  
INVENTOR(S) : Patrick Lewis Blott Page 1 of 3

It is certified that error appears in the above-identified patent and that said Letters Patent is hereby corrected as shown below:

On the Title Page

On Page 6, Column 1, Line 38, under Other Publications, delete "Stei-Greffe" and insert --Steri-Greffe--.

On Page 6, Column 2, Line 5, under Other Publications, delete "Reporton" and insert --Report on--.

On Page 6, Column 2, Line 9, under Other Publications, delete "Reporton" and insert --Report on--.

On Page 6, Column 2, Line 13, under Other Publications, delete "Reporton" and insert --Report on--.

On Page 6, Column 2, Line 24, under Other Publications, delete "Reporton" and insert --Report on--.

On Page 6, Column 2, Line 28, under Other Publications, delete "Reporton" and insert --Report on--.

In the Drawings

On Sheet 33 of 38, Fig. 34, Line 1 (X-axis), delete "H202" and insert --$H_2O_2$--.

On Sheet 34 of 38, Fig. 35, Line 1 (X-axis), delete "H202" and insert --$H_2O_2$--.

On Sheet 34 of 38, Fig. 35, Line 2 (X-axis), delete "H202" and insert --$H_2O_2$--.

In the Specification

In Column 5, Line 4, delete "bed" and insert --bed.--.

In Column 14, Line 6, delete "maybe" and insert --may be--.

Signed and Sealed this  
Sixteenth Day of August, 2022

Katherine Kelly Vidal  
*Director of the United States Patent and Trademark Office*

CERTIFICATE OF CORRECTION (continued)
U.S. Pat. No. 11,298,453 B2

In Column 14, Line 9, delete "maybe" and insert --may be--.

In Column 14, Line 53, delete "bupivicaine," and insert --bupivacaine,--.

In Column 17, Line 39, delete "below.)," and insert --below),--.

In Column 17, Line 58, delete "8 1." and insert --81,--.

In Column 25, Line 3, delete "ulcers." and insert --ulcers).--.

In Column 29, Line 47, after "so", delete "a".

In Column 34, Line 57, delete "phoshpate." and insert --phoshpate--.

In Column 34, Line 59, delete "(adrenoline," and insert --(adrenaline,--.

In Column 39, Line 7, delete "macroglogulin;" and insert --macroglobulin;--.

In Column 39, Line 20, delete "stretoptokinase," and insert --streptokinase,--.

In Column 39, Line 28, delete "gutathione" and insert --glutathione--.

In Column 41, Line 40, delete "materials" and insert --materials.--.

In Column 46, Line 11-12, delete "(adrenoline" and insert --(adrenaline,--.

In Column 46, Line 24, delete "insoluble" and insert --(insoluble--.

In Column 46, Line 34, delete "bed.)," and insert --bed),--.

In Column 47, Line 15, delete "-a]" and insert -- -α]--.

In Column 49, Line 52, delete "equilibrium" and insert --equilibrium.--.

In Column 52, Line 10, delete "glycosoaminoglycans," and insert --glycosaminoglycans,--.

In Column 53, Line 63, delete "is/are is" and insert --is/are--.

In Column 59, Line 56, delete "(7)" and insert --(7).--.

In Column 60, Line 2, delete "removed" and insert --removed.--.

In Column 61, Line 5, delete "(42)," and insert --(42).--.

In Column 61, Line 9 (Approx.), delete "frustroconical," and insert --frustoconical,--.

CERTIFICATE OF CORRECTION (continued)
U.S. Pat. No. 11,298,453 B2

In Column 61, Line 48, delete "frustroconical," and insert --frustoconical,--.

In Column 65, Line 57, delete "hereinbefore" and insert --hereinbefore.--.

In Column 65, Line 65, delete "hereinbefore" and insert --hereinbefore.--.

In Column 66, Line 6, delete "hereinbefore" and insert --hereinbefore.--.

In Column 66, Lines 15-16, delete "hereinbefore" and insert --hereinbefore.--.

In Column 66, Line 26, delete "hereinbefore" and insert --hereinbefore.--.

In Column 66, Line 37, delete "hereinbefore" and insert --hereinbefore.--.

In Column 72, Line 13, delete "and or" and insert --and/or--.

In Column 72, Line 22, delete "(Minnucells" and insert --(Minucells--.

In Column 72, Line 39, delete "direction," and insert --direction.--.

In Column 73, Line 25, delete "and or" and insert --and/or--.

In Column 73, Line 34, delete "(Minnucells" and insert --(Minucells--.

In Column 74, Line 23 (Approx.), delete "dehdrogenase" and insert --dehydrogenase--.

In Column 76, Line 3, delete "point" and insert --point.--.

In Column 77, Line 35 (Approx.), delete "(Minnucells" and insert --(Minucells--.

In Column 78, Line 38 (Approx.), delete "dehdrogenase" and insert --dehydrogenase--.

In Column 78, Line 58, delete "(Hereus" and insert --(Heraeus--.

In Column 79, Line 22, delete "mbar)." and insert --mbar.--.

In Column 80, Line 49, delete "(Hereus" and insert --(Heraeus--.

In Column 81, Line 54, delete "clickerpress." and insert --clicker-press.--.